(12) United States Patent
Hubbard et al.

(10) Patent No.: US 10,434,037 B2
(45) Date of Patent: Oct. 8, 2019

(54) KIT AND METHOD FOR DETECTING POROUS DENTAL HYDROXYAPATITE

(71) Applicant: Incisive Technologies Pty Ltd, Melbourne, Victoria (AU)

(72) Inventors: Michael James Hubbard, Melbourne (AU); Jonathan Edward Mangum, Melbourne (AU)

(73) Assignee: INCISIVE TECHNOLOGIES PTY LTD, Melbourne (AU)

( * ) Notice: Subject to any disclaimer, the term of this patent is extended or adjusted under 35 U.S.C. 154(b) by 203 days.

(21) Appl. No.: 15/422,996

(22) Filed: Feb. 2, 2017

(65) Prior Publication Data

US 2017/0196777 A1 Jul. 13, 2017

Related U.S. Application Data

(62) Division of application No. 13/501,676, filed as application No. PCT/AU2011/000303 on Mar. 18, 2011, now abandoned.

(30) Foreign Application Priority Data

Mar. 19, 2010 (AU) ................ 2010901171

(51) Int. Cl.
| | |
|---|---|
| A61K 6/00 | (2006.01) |
| A61K 49/00 | (2006.01) |
| A61K 49/04 | (2006.01) |
| C07K 14/00 | (2006.01) |
| G01N 33/68 | (2006.01) |
| A61B 5/00 | (2006.01) |

(52) U.S. Cl.
CPC ............ *A61K 6/002* (2013.01); *A61B 5/4547* (2013.01); *A61K 49/001* (2013.01); *A61K 49/006* (2013.01); *A61K 49/0438* (2013.01); *C07K 14/00* (2013.01); *G01N 33/6893* (2013.01)

(58) Field of Classification Search
None
See application file for complete search history.

(56) References Cited

U.S. PATENT DOCUMENTS

| | | | |
|---|---|---|---|
| 3,854,586 A | 12/1974 | Perkins | |
| 3,956,480 A * | 5/1976 | Dichter | A61K 8/416 424/54 |
| 4,175,326 A | 11/1979 | Goodson | |
| 4,208,479 A | 6/1980 | Zuk | |
| 4,278,653 A | 7/1981 | Harris | |
| 4,703,016 A | 10/1987 | Merril | |
| 4,959,306 A | 9/1990 | Kameda | |
| 5,691,453 A | 11/1997 | Wertz | |
| 5,981,720 A | 11/1999 | Azen | |
| 6,346,121 B1 | 2/2002 | Hicks | |
| 2006/0127961 A1 | 6/2006 | Gregory | |
| 2008/0038686 A1 * | 2/2008 | Nagai | A61B 5/0088 433/29 |
| 2008/0308744 A1 | 12/2008 | Frangioni | |
| 2009/0048433 A1 | 2/2009 | Richter | |
| 2009/0098050 A1 | 4/2009 | Yarbrough | |

FOREIGN PATENT DOCUMENTS

| | | |
|---|---|---|
| EP | 245052 | 11/1987 |
| WO | WO 96/35812 | 11/1996 |
| WO | WO 2007002535 | 1/2007 |
| WO | WO 2007/038683 | 4/2007 |

OTHER PUBLICATIONS

Carr, C.W., "Studies on the Binding of Small Ions in Protein Solutions with the Use of Membrane Electrodes. IV. The Binding of Calcium Ions in Solutions of Various Proteins," *Arch. Biochem Biophys*. 46:424-431, Academic Press, New York (Sep. 1953).
Bennick, et al. The Nature of the Hydroxyapatite-Binding Site in Salivary Acidic Proline-Rich Proteins, Biochem. J. 183:115-126, 1979.
Daniel et al., Visualization of lipoprotein receptors by ligand blotting, J. Biol. Chem. 1983, 258:4606-4611.
Teranaka, T., et al., "Protein Content and Amino-Acid Content of Consolidated Carious Lesions in Human Enamel and of Experimental Lesions in Bovine Enamel Exposed to the Human Mouth,", *Archs Oral Biol*., 31:405-410, Pergamon Journals Ltd., Great Britain (1986).
Aoba et al., Selective Adsorption of Porcine-Amelogenins onto Hydroxyapatite and their Inhibitory Activity on Hydroxyapatite Growth in Supersaturated Solutions, Calcif Tissue Int (1987) 41:281-289.
Burnam, Intravenous Fluorescein Vascularity Studies of a New Technique: The Subcutaneous Pedicled Extension Flap, Arch Otolaryngol Head Neck Surg. 1993;119(12):1329-1337 (abstract only).
Hubbard, M.J., Calbindin$_{28kDa}$ and Calmodulin are Hyperabundant in Rat Dental Enamel Cells. Identification of the protein phosphatase calcineurin as a principal calmodulin target and of a secretion-related role for calbindin$_{28kDa}$.European Journal of Biochemistry, 230: 68-79, FEBS (1995).

(Continued)

*Primary Examiner* — Andrea S Grossman
(74) *Attorney, Agent, or Firm* — Barnes & Thornburg LLP; G. Peter Nichols

(57) ABSTRACT

The present invention relates to a kit and a probe for detecting porous dental hydroxyapatite that includes a protein capable of binding porous dental hydroxyapatite or a detector thereof. The invention also relates to a method for detecting a condition involving porous dental hydroxyapatite that includes detecting in or on a tooth or a sample of the tooth of a subject a protein bound to porous dental hydroxyapatite. The invention also relates to methods for detecting a hypomineralization developmental dental defect or detecting intact and/or broken MIH enamel, and to a kit and method for removing a protein bound to porous dental hydroxyapatite.

21 Claims, 22 Drawing Sheets
(7 of 22 Drawing Sheet(s) Filed in Color)
Specification includes a Sequence Listing.

(56) References Cited

OTHER PUBLICATIONS

Wassell et al., Adsorption of bovine serum albumin onto hydroxyapatite, Biomaterials 1995 vol. 16 No. 9, 697-702.
Hubbard, M. J., "Abundant Calcium Homeostasis Machinery in Rat Dental Enamel Cells. Up-regulation of calcium store proteins during enamel mineralization implicates the endoplasmic reticulum in calcium transcytosos." European Journal of Biochemistry, 239: 611-623, FEBS (1996).
Sigma, Albumin From Bovine Serum, pp. 1-4, 2000, retrieved from http://www.sigmaaldrich.com/content/dam/sigma-aldrich/docs/Sigma/Product_Information_Sheet/a1933pis.pdf.
Weerheijm, K.L., et al., Judgement criteria for Molar Incisor Hypomineralisation (MIH) in epidemiologic studies: a summary of the European meeting on MIH held in Athens, 2003, *Eur. J. Paed. Dent.*, 3:110-113, European Academy of Paediatric Dentistry (Sep. 2003).
Parmar et al., Demineralising effect of EDTA at different concentration and pH—A spectrophotometer study, Endodontology, 16, 2004, 54-57.
Simpson, R.J., "Protein Chromatography on Hydroxyapatite," In: Simpson, R.J. (ed). Purifying Proteins for Proteomics: A Laboratory Manual, Cold Spring Harbor Laboratory Press, Cold Spring Harbor, New York, pp. 337-354 (2004).
Phos-Flur® Anticavity Dental Rise Acidulated Phosphate Fluroide Solution product information, 4 pages, retrieved on May 29, 2013 from http://www.colgateprofessional.com/products/Colgate-Phos-Flur.Rinse, available since Apr. 10, 2004 according to New Zealand Intellectual Property Office.
Mangum, J.E., et al., "Towards second-generation proteome analysis of murine enamel-forming cells," *Eur. J. Oral Sci.*, 114(*Suppl. I*) 259-265, Wiley-Blackwell (2006).
Delcroix et al., A Multienzyme Network Functions in Intestinal Protein Digestion by a Platyhelminth Parasite, The Journal of Biological Chemistry, 281 (51), pp. 39316-39329, Dec. 22, 2006.
Ryan et al., Cellular Uptake of Gold Nanoparticles Passivated with BSA-SV50 Large T Antigen Conjugates, Anal. Chem. 2007, 79, 9150-9159.
Zhou, Proteomic Analysis of Hydroxyapatite Interaction Proteins in Bone, Ann. N.Y. Acad. Sci. 1116: 323-326 (2007).
Heiss, A., et al., "Protein Synthesis, Post-Translational Modification, and Degradation: Hierarchical Role of Fetuin-A and Acidic Serum Proteins in the Formation and Stabilization of Calcium Phospate Particles,"*J. Biol. Chem.*, 283:14815-14825, The American Society for Biochemistry and Molecular Biology, Inc., United States (Mar. 2008).
WV-05-01 Mouthwash with NaF and CPC product information, 1 page, retrieved on Jun. 24, 2013 from www.merck-performance-materials.com/merck-ppf/detailRequest?, available since Jun. 30, 2008 according to New Zealand Intellectual Property Office.
Yarbrough, D.K., et al., "Specific Binding and Mineralization of Calcified Surfaces by Small Peptides," *Calcif. Tissue Int.*, 86:58-66, Springer (Dec. 2009 epub).
Designer Biosciences, Peptide Modifications, 2009, retrieved from http://www.designerbioscience.com/doc/Peptide_Modifications.pdf on Jul. 27, 2015, pp. 1-2.
Millipore et al., Fast and Easy Protein Preparation, pp. 1-16, citation on p. 3, 2010, retrieved from http://fscimage.fishersci.com/cmsassets/downloads/segment/Scientific/pdf/Millipore/protein_prep_fast.pdf.
Mangum, J.E., et al., "Surface Integrity Governs the Proteome of Hypomineralized Enamel", *J. Dental Res.*, 89(10):1160-1165, SAGE Publications (Jul. 2010 epub).
Crombie, F.A., et al., "Characterisation of developmentally hypomineralised human enamel,"*J. Dent.*, 41:611-618, Elsevier Ltd., England (May 2013).
Lee, Y.H. et al., Proteomic Evaluation of Acquired Enamel Pellicle during In Vivo Formation, *PLOS One*, 8:e67919, Public Library of Science, United States (Jul. 2013).
Sigma, Indocyanine Green, 2 pages, retrieved from http://uthsc.edu/eye/osha/documents/indocyaninegreenmsds.pdf on Aug. 4, 2016.
International Search Report for International Patent Application No. PCT/AU2011/000303, dated May 12, 2011; 3 pages.
Written Opinion of the International Searching Authority for International Patent Application No. PCT/AU2011/000303, dated May 12, 2011; 6 pages.
International Preliminary Report on Patentability for International Patent Application No. PCT/AU2011/000303, dated May 12, 2011; 17 pages.

\* cited by examiner

MKWVTFISLLFLFSSAYSRGVFRRDAHKSEVAHRFKDLGEENFKALVLIAFAQYLQQCPF
EDHVKLVNEVTEFAKTCVADESAENCDKSLHTLFGDKLCTVATLRETYGEMADCCAKQEP
ERNECFLQHKDDNPNLPRLVRPEVDVMCTAFHDNEETFLKKYLYEIARRHPYFYAPELLF
FAKRYKAAFTECCQAADKAACLLPKLDELRDEGKASSAKQRLKCASLQKFGERAFKAWAV
ARLSQRFPKAEFAEVSKLVTDLTKVHTECCHGDLLECADDRADLAKYICENQDSISSKLK
ECCEKPLLEKSHCIAEVENDEMPADLPSLAADFVESKDVCKNYAEAKDVFLGMFLYEYAR
RHPDYSVVLLLRLAKTYETTLEKCCAAADPHECYAKVFDEFKPLVEEPQNLIKQNCELFE
QLGEYKFQNALLVRYTKKVPQVSTPTLVEVSRNLGKVGSKCCKHPEAKRMPCAEDYLSVV
LNQLCVLHEKTPVSDRVTKCCTESLVNRRPCFSALEVDETYVPKEFNAETFTFHADICTL
SEKERQIKKQTALVELVKHKPKATKEQLKAVMDDFAAFVEKCCKADDKETCFAEEGKKLV
AASQAALGL

Figure 6 (SEQ ID NO: 1; SwissProt accession P02768; ALBU_Human Serum albumin OS=Homo sapiens GN=ALB PE=1 SV=2).

MGPTSGPSLLLLLLTHLPLALGSPMYSIITPNILRLESEETMVLEAHDAQGDVPVTVTVH
DFPGKKLVLSSEKTVLTPATNHMGNVTFTIPANREFKSEKGRNKFVTVQATFGTQVVEKV
VLVSLQSGYLFIQTDKTIYTPGSTVLYRIFTVNHKLLPVGRTVMVNIENPEGIPVKQDSL
SSQNQLGVLPLSWDIPELVNMGQWKIRAYYENSPQQVFSTEFEVKEYVLPSFEVIVEPTE
KFYYIYNEKGLEVTITARFLYGKKVEGTAFVIFGIQDGEQRISLPESLKRIPIEDGSGEV
VLSRKVLLDGVQNPRAEDLVGKSLYVSATVILHSGSDMVQAERSGIPIVTSPYQIHFTKT
PKYFKPGMPFDLMVFVTNPDGSPAYRVPVAVQGEDTVQSLTQGDGVAKLSINTHPSQKPL
SITVRTKKQELSEAEQATRTMQALPYSTVGNSNNYLHLSVLRTELRPGETLNVNFLLRMD
RAHEAKIRYYTYLIMNKGRLLKAGRQVREPGQDLVVLPLSITTDFIPSFRLVAYYTLIGA
SGQREVVADSVWVDVKDSCVGSLVVKSGQSEDRQPVPGQQMTLKIEGDHGARVVLVAVDK
GVFVLNKKNKLTQSKIWDVVEKADIGCTPGSGKDYAGVFSDAGLTFTSSSGQQTAQRAEL
QCPQPAARRRSVQLTEKRMDKVGKYPKELRKCCEDGMRENPMRFSCQRRTRFISLGEAC
KKVFLDCCNYITELRRQHARASHLGLARSNLDEDIIAEENIVSRSEFPESWLWNVEDLKE
PPKNGISTKLMNIFLKDSITTWEILAVSMSDKKGICVADPFEVTVMQDFFIDLRLPYSVV
RNEQVEIRAVLYNYRQNQELKVRVELLHNPAFCSLATTKRRHQQTVTIPPKSSLSVPYVI
VPLKTGLQEVEVKAAVYHHFISDGVRKSLKVVPEGIRMNKTVAVRTLDPERLGREGVQKE
DIPPADLSDQVPDTESETRILLQGTPVAQMTEDAVDAERLKHLIVTPSGCGEQNMIGMTP
TVIAVHYLDETEQWEKFGLEKRQGALELIKKGYTQQLAFRQPSSAFAAFVKRAPSTWLTA
YVVKVFSLAVNLIAIDSQVLCGAVKWLILEKQKPDGVFQEDAPVIHQEMIGGLRNNNEKD
MALTAFVLISLQEAKDICEEQVNSLPGSITKAGDFLEANYMNLQRSYTVAIAGYALAQMG
RLKGPLLNKFLTTAKDKNRWEDPGKQLYNVEATSYALLALLQLKDFDFVPPVVRWLNEQR

YYGGGYGSTQATFMVFQALAQYQKDAPDHQELNLDVSLQLPSRSSKITHRIHWESASLLR
SEETKENEGFTVTAEGKGQGTLSVVTMYHAKAKDQLTCNKFDLKVTIKPAPETEKRPQDA
KNTMILEICTRYRGDQDATMSILDISMMTGFAPDTDDLKQLANGVDRYISKYELDKAFSD
RNTLIIYLDKVSHSEDDCLAFKVHQYFNVELIQPGAVKVYAYYNLEESCTRFYHPEKEDG
KLNKLCRDELCRCAEENCFIQKSDDKVTLEERLDKACEPGVDYVYKTRLVKVQLSNDFDE
YIMAIEQTIKSGSDEVQVGQQRTFISPIKCREALKLEEKKHYLMWGLSSDFWGEKPNLSY
IIGKDTWVEHWPEEDECQDEENQKQCQDLGAFTESMVVFGCPN

Figure 7 (SEQ ID NO: 2; SwissProt accession P01024; CO3_Human Complement C3 OS=Homo sapiens GN=C3 PE=1 SV=2).

MPSSVSWGILLLAGLCCLVPVSLAEDPQGDAAQKTDTSHHDQDHPTFNKITPNLAEFAFS
LYRQLAHQSNSTNIFFSPVSIATAFAMLSLGTKADTHDEILEGLNFNLTEIPEAQIHEGF
QELLRTLNQPDSQLQLTTGNGLFLSEGLKLVDKFLEDVKKLYHSEAFTVNFGDTEEAKKQ
INDYVEKGTQGKIVDLVKELDRDTVFALVNYIFFKGKWERPFEVKDTEEEDFHVDQVTTV
KVPMMKRLGMFNIQHCKKLSSWVLLMKYLGNATAIFFLPDEGKLQHLENELTHDIITKFL
ENEDRRSASLHLPKLSITGTYDLKSVLGQLGITKVFSNGADLSGVTEEAPLKLSKAVHKA
VLTIDEKGTEAAGAMFLEAIPMSIPPEVKFNKPFVFLMIEQNTKSPLFMGKVVNPTQK

Figure 8 (SEQ ID NO: 3; SwissProt accession P01009; A1AT_Human Alpha-1-antitrypsin OS=Homo sapiens GN=SERPINA1 PE=1 SV=3).

MTCKMSQLERNIETIINTFHQYSVKLGHPDTLNQGEFKELVRKDLQNFLKKENKNEKVIE
HIMEDLDTNADKQLSFEEFIMLMARLTWASHEKMHEGDEGPGHHHKPGLGEGTP

Figure 9 (SEQ ID NO: 4; SwissProt accession P06702; S10A9_Human Protein S100-A9 OS=Homo sapiens GN=S100A9 PE=1 SV=1).

MKLVFLVLLFLGALGLCLAGRRRSVQWCAVSQPEATKCFQWQRNMRKVRGPPVSCIKRDS
PIQCIQAIAENRADAVTLDGGFIYEAGLAPYKLRPVAAEVYGTERQPRTHYYAVAVVKKG
GSFQLNELQGLKSCHTGLRRTAGWNVPIGTLRPFLNWTGPPEPIEAAVARFFSASCVPGA
DKGQFPNLCRLCAGTGENKCAFSSQEPYFSYSGAFKCLRDGAGDVAFIRESTVFEDLSDE
AERDEYELLCPDNTRKPVDKFKDCHLARVPSHAVVARSVNGKEDAIWNLLRQAQEKFGKD
KSPKFQLFGSPSGQKDLLFKDSAIGFSRVPPRIDSGLYLGSGYFTAIQNLRKSEEEVAAR

```
RARVVWCAVGEQELRKCNQWSGLSEGSVTCSSASTTEDCIALVLKGEADAMSLDGGYVYT
AGKCGLVPVLAENYKSQQSSDPDPNCVDRPVEGYLAVAVVRRSDTSLTWNSVKGKKSCHT
AVDRTAGWNIPMGLLFNQTGSCKFDEYFSQSCAPGSDPRSNLCALCIGDEQGENKCVPNS
NERYYGYTGAFRCLAENAGDVAFVKDVTVLQNTDGNNNEAWAKDLKLADFALLCLDGKRK
PVTEARSCHLAMAPNHAVVSRMDKVERLKQVLLHQQAKFGRNGSDCPDKFCLFQSETKNL
LFNDNTECLARLHGKTTYEKYLGPQYVAGITNLKKCSTSPLLEACEFLRK
```

Figure 10 (SEQ ID NO: 5; SwissProt accession P02788; TRFL_Human Lactotransferrin OS=Homo sapiens GN=LTF PE=1 SV=6)

```
MEQLSSANTRFALDLFLALSENNPAGNIFISPFSISSAMAMVFLGTRGNTAAQLSKTFHF
NTVEEVHSRFQSLNADINKRGASYILKLANRLYGEKTYNFLPEFLVSTQKTYGADLASVD
FQHASEDARKTINQWVKGQTEGKIPELLASGMVDNMTKLVLVNAIYFKGNWKDKFMKEAT
TNAPFRLNKKDRKTVKMMYQKKKFAYGYIEDLKCRVLELPYQGEELSMVILLPDDIEDES
TGLKKIEEQLTLEKLHEWTKPENLDFIEVNVSLPRFKLEESYTLNSDLARLGVQDLFNSS
KADLSGMSGARDIFISKIVHKSFVEVNEEGTEAAAATAGIATFCMLMPEENFTADHPFLF
FIRHNSSGSILFLGRFSSP
```

Figure 11 (SEQ ID NO: 6; SwissProt accession P30740; ILEU_Human Leukocyte elastase inhibitor OS=Homo sapiens GN=SERPINB1 PE=1 SV=1).

```
MYSNVIGTVTSGKRKVYLLSLLLIGFWDCVTCHGSPVDICTAKPRDIPMNPMCIYRSPEK
KATEDEGSEQKIPEATNRRVWELSKANSRFATTFYQHLADSKNDNDNIFLSPLSISTAFA
MTKLGACNDTLQQLMEVFKFDTISEKTSDQIHFFFAKLNCRLYRKANKSSKLVSANRLFG
DKSLTFNETYQDISELVYGAKLQPLDFKENAEQSRAAINKWVSNKTEGRITDVIPSEAIN
ELTVLVLVNTIYFKGLWKSKFSPENTRKELFYKADGESCSASMMYQEGKFRYRRVAEGTQ
VLELPFKGDDITMVLILPKPEKSLAKVEKELTPEVLQEWLDELEEMMLVVHMPRFRIEDG
FSLKEQLQDMGLVDLFSPEKSKLPGIVAEGRDDLYVSDAFHKAFLEVNEEGSEAAASTAV
VIAGRSLNPNRVTFKANRPFLVFIREVPLNTIIFMGRVANPCVK
```

Figure 12 (SEQ ID NO: 7; SwissProt accession P01008; ANT3_Human Antithrombin-III OS=Homo sapiens GN=SERPINC1 PE=1 SV=1).

MVLSPADKTNVKAAWGKVGAHAGEYGAEALERMFLSFPTTKTYFPHFDLSHGSAQVKGHG
KKVADALTNAVAHVDDMPNALSALSDLHAHKLRVDPVNFKLLSHCLLVTLAAHLPAEFTP
AVHASLDKFLASVSTVLTSKYR

Figure 13 (SEQ ID NO: 8; SwissProt accession P69905; HBA_Human Hemoglobin subunit alpha OS=Homo sapiens GN=HBA1 PE=1 SV=2).

MVHLTPEEKSAVTALWGKVNVDEVGGEALGRLLVVYPWTQRFFESFGDLSTPDAVMGNPK
VKAHGKKVLGAFSDGLAHLDNLKGTFATLSELHCDKLHVDPENFRLLGNVLVCVLAHHFG
KEFTPPVQAAYQKVVAGVANALAHKYH

Figure 14 (SEQ ID NO: 9; SwissProt accession P68871; HBB_Human Hemoglobin subunit beta OS=Homo sapiens GN=HBB PE=1 SV=2).

MVHLTPEEKTAVNALWGKVNVDAVGGEALGRLLVVYPWTQRFFESFGDLSSPDAVMGNPK
VKAHGKKVLGAFSDGLAHLDNLKGTFSQLSELHCDKLHVDPENFRLLGNVLVCVLARNFG
KEFTPQMQAAYQKVVAGVANALAHKYH

Figure 15 (SEQ ID NO: 10; SwissProt accession P02042; HBD_Human Hemoglobin subunit delta OS=Homo sapiens GN=HBD PE=1 SV=2).

MRLLQLLFRASPATLLLVLCLQLGANKAQDNTRKIIIKNFDIPKSVRPNDEVTAVLAVQT
ELKECMVVKTYLISSIPLQGAFNYKYTACLCDDNPKTFYWDFYTNRTVQIAAVVDVIREL
GICPDDAAVIPIKNNRFYTIEILKVE

Figure 16 (SEQ ID NO: 11; SwissProt accession P12273; PIP_Human Prolactin-inducible protein OS=Homo sapiens GN=PIP PE=1 SV=1).

MKLFWLLFTIGFCWAQYSSNTQQGRTSIVHLFEWRWVDIALECERYLAPKGFGGVQVSPP
NENVAIHNPFRPWWERYQPVSYKLCTRSGNEDEFRNMVTRCNNVGVRIYVDAVINHMCGN
AVSAGTSSTCGSYFNPGSRDFPAVPYSGWDFNDGKCKTGSGDIENYNDATQVRDCRLSGL
LDLALGKDYVRSKIAEYMNHLIDIGVAGFRIDASKHMWPGDIKAILDKLHNLNSNWFPEG
SKPFIYQEVIDLGGEPIKSSDYFGNGRVTEFKYGAKLGTVIRKWNGEKMSYLKNWGEGWG

```
FMPSDRALVFVDNHDNQRGHGAGGASILTFWDARLYKMAVGFMLAHPYGFTRVMSSYRWP
RYFENGKDVNDWVGPPNDNGVTKEVTINPDTTCGNDWVCEHRWRQIRNMVNFRNVVDGQP
FTNWYDNGSNQVAFGRGNRGFIVFNNDDWTFSLTLQTGLPAGTYCDVISGDKINGNCTGI
KIYVSDDGKAHFSISNSAEDPFIAIHAESKL
```

Figure 17 (SEQ ID NO: 12; SwissProt accession P04745; AMY1_Human Alpha-amylase 1 OS=Homo sapiens GN=AMY1A PE=1 SV=2).

```
EIVLTQSPGTLSLSPGERATLSCRASQSVSNSYLAWYQQKPGQAPRLLIYGASSRATGIP
DRFSGSGSGTDFTLTISRLEPDDFAVYYCQQYGSSPQTFGQGSKVEIKR
```

Figure 18 (SEQ ID NO: 13; SwissProt accession P01620; KV302_Human Ig kappa chain V-III region SIE OS=Homo sapiens PE=1 SV=1).

```
ASPTSPKVFPLSLDSTPQDGNVVVACLVQGFFPQEPLSVTWSESGQNVTARNFPPSQDAS
GDLYTTSSQLTLPATQCPDGKSVTCHVKHYTNPSQDVTVPCPVPPPPCCHPRLSLHRPA
LEDLLLGSEANLTCTLTGLRDASGATFTWTPSSGKSAVQGPPERDLCGCYSVSSVLPGCA
QPWNHGETFTCTAAHPELKTPLTANITKSGNTFRPEVHLLPPPSEELALNELVTLTCLAR
GFSPKDVLVRWLQGSQELPREKYLTWASRQEPSQGTTTFAVTSILRVAAEDWKKGDTFSC
MVGHEALPLAFTQKTIDRMAGKPTHVNVSVVMAEVDGTCY
```

Figure 19 (SEQ ID NO: 14; SwissProt accession P01877; IGHA2_Human Ig alpha-2 chain C region OS=Homo sapiens GN=IGHA2 PE=1 SV=3).

```
MAFLPSWVCVLVGSFSASLAGTSNLSETEPPLWKESPGQLSDYRVENSMYIINPWVYLER
MGMYKIILNQTARYFAKFAPDNEQNILWGLPLQYGWQYRTGRLADPTRRTNCGYESGDHM
CISVDSWWADLNYFLSSLPFLAAVDSGVMGISSDQVRLLPPPKNERKFCYDVSSCRSSFP
ETMNKWNTFYQYLQSPFSKFDDLLKYLWAAHTSTLADNIKSFEDRYDYYSKAEAHFERSW
VLAVDHLAAVLFPTTLIRSYKFQKGMPPRILLNTDVAPFISDFTAFQNVVLVLLNMLDNV
DKSIGYLCTEKSNVYRDHSESSSRSYGNNS
```

Figure 20 (SEQ ID NO: 15; SwissProt accession Q6P5S2; CF058_Human Uncharacterized protein C6orf58 OS=Homo sapiens GN=C6orf58 PE=1 SV=2).

MNSLSEANTKFMFDLFQQFRKSKENNIFYSPISITSALGMVLLGAKDNTAQQIKKVLHFD
QVTENTTGKAATYHVDRSGNVHHQFQKLLTEFNKSTDAYELKIANKLFGEKTYLFLQEYL
DAIKKFYQTSVESVDFANAPEESRKKINSWVESQTNEKIKNLIPEGNIGSNTTLVLVNAI
YFKGQWEKKFNKEDTKEEKFWPNKNTYKSIQMMRQYTSFHFASLEDVQAKVLEIPYKGKD
LSMIVLLPNEIDGLQKLEEKLTAEKLMEWTSLQNMRETRVDLHLPRFKVEESYDLKDTLR
TMGMVDIFNGDADLSGMTGSRGLVLSGVLHKAFVEVTEEGAEAAAATAVVGFGSSPTSTN
EEFHCNHPFLFFIRQNKTNSILFYGRFSSP

Figure 21 (SEQ ID NO: 16; SwissProt accession P29508; SPB3_Human Serpin B3 OS=Homo sapiens GN=SERPINB3 PE=1 SV=2).

MGTWILFACLLGAAFAMPLPPHPGHPGYINFSYEVLTPLKWYQSIRPPYPSYGYEPMGGW
LHHQIIPVLSQQHPPTHTLQPHHHIPVVPAQQPVIPQQPMMPVPGQHSMTPIQHHQPNLP
PPAQQPYQPQPVQPQPHQPMQPQPPVHPMQPLPPQPPLPPMFPMQPLPPMLPDLTLEAWP
STDKTKREEVD

Figure 22 (SEQ ID NO: 17; SwissProt accession Q99217; AMELX_Human Amelogenin, X isoform OS=Homo sapiens GN=AMELX PE=1 SV=1).

MGTWILFACLVGAAFAMPLPPHPGHPGYINFSYENSHSQAINVDRIALVLTPLKWYQSMI
RPPYSSYGYEPMGGWLHHQIIPVVSQQHPLTHTLQSHHHIPVVPAQQPRVRQQALMPVPG
QQSMTPTQHHQPNLPLPAQQPFQPQPVQPQPHQPMQPQPPVQPMQPLLPQPPLPPMFPLR
PLPPILPDLHLEAWPATDKTKQEEVD

Figure 23 (SEQ ID NO: 18; SwissProt accession Q99218; AMELY_Human Amelogenin, Y isoform OS=Homo sapiens GN=AMELY PE=2 SV=2).

MGTWILFACLLGAAFAMPLPPHPGSPGYINLSYEKSHSQAINTDRTALVLTPLKWYQSMI
RQPYPSYGYEPMGGWLHHQIIPVLSQQHPPSHTLQPHHHLPVVPAQQPVAPQQPMMPVPG
HHSMTPTQHHQPNIPPSAQQPFQQPFQPQAIPPQSHQPMQPQSPLHPMQPLAPQPPLPPL
FSMQPLSPILPELPLEAWPATDKTKREEVD

Figure 24 (SEQ ID NO: 19; SwissProt accession P63277; AMELX_MOUSE Amelogenin, X isoform OS=Mus musculus GN=Amelx PE=2 SV=1).

MVLSAADKGNVKAAWGKVGGHAAEYGAEALERMFLSFPTTKTYFPHFDLSHGSAQVKGHG
AKVAAALTKAVEHLDDLPGALSELSDLHAHKLRVDPVNFKLLSHSLLVTLASHLPSDFTP
AVHASLDKFLANVSTVLTSKYR

Figure 25 (SEQ ID NO: 20; SwissProt accession P01966; HBA_BOVIN Hemoglobin subunit alpha OS=Bos taurus GN=HBA PE=1 SV=2).

MLTAEEKAAVTAFWGKVKVDEVGGEALGRLLVVYPWTQRFFESFGDLSTADAVMNNPKVK
AHGKKVLDSFSNGMKHLDDLKGTFAALSELHCDKLHVDPENFKLLGNVLVVVLARNFGKE
FTPVLQADFQKVVAGVANALAHRYH

Figure 26 (SEQ ID NO: 21; SwissProt accession P02070; HBB_BOVIN Hemoglobin subunit beta OS=Bos taurus GN=HBB PE=1 SV=1).

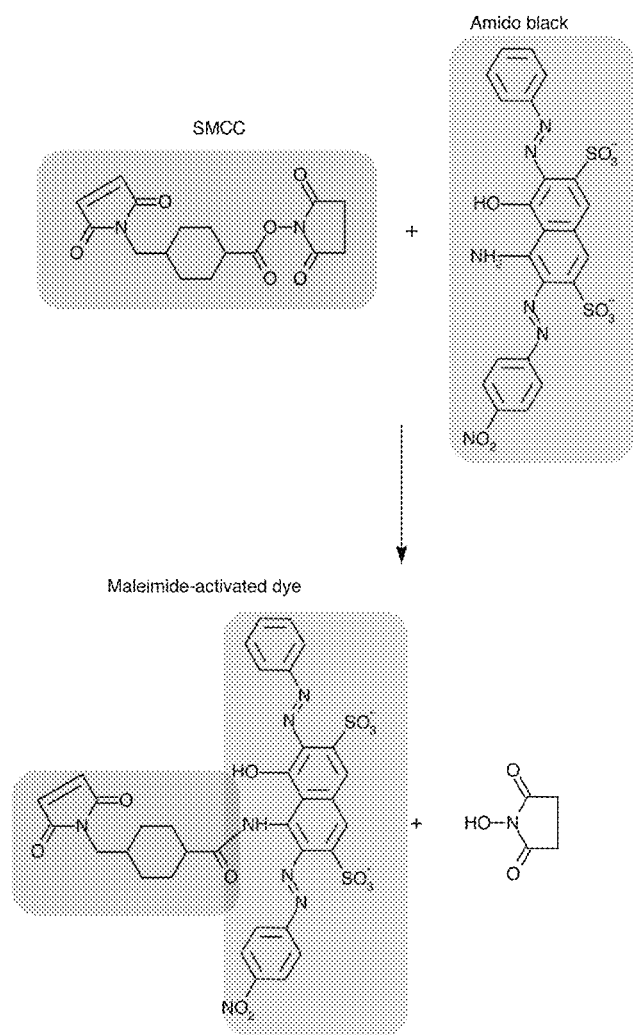
Figure 27. Production of a maleimide-activated coloured reporter.

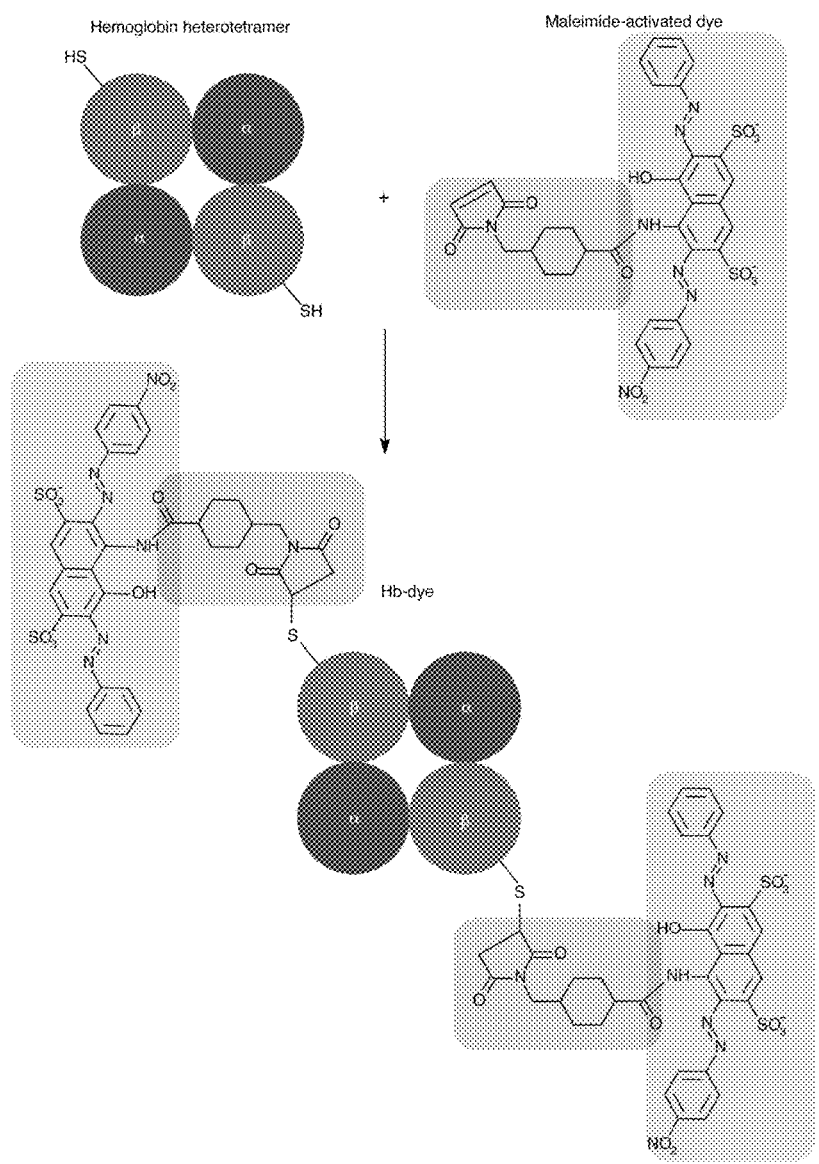
Figure 28. Production of a coloured reporter-conjugated protein.

```
SEQUENCE LISTING

<160> NUMBER OF SEQ ID NOS: 21

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140
```

-continued

```
Asp Val Met Cys Thr Ala Phe His Asp Asn Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
                180                 185                 190

Cys Gln Ala Ala Asp Lys Ala Ala Cys Leu Leu Pro Lys Leu Asp Glu
                195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
                275                 280                 285

Cys Glu Asn Gln Asp Ser Ile Ser Ser Lys Leu Lys Glu Cys Cys Glu
                290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
                355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
                435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
                530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
```

-continued

```
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 2
<211> LENGTH: 1663
<212> TYPE: PRT
<213> ORGANISM: Homo sapiens

<400> SEQUENCE: 2

Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
        35                  40                  45

Ala Gln Gly Asp Val Pro Val Thr Val Thr Val His Asp Phe Pro Gly
    50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
    290                 295                 300

Lys Val Leu Leu Asp Gly Val Gln Asn Pro Arg Ala Glu Asp Leu Val
305                 310                 315                 320

Gly Lys Ser Leu Tyr Val Ser Ala Thr Val Ile Leu His Ser Gly Ser
```

-continued

```
            325                 330                 335
Asp Met Val Gln Ala Glu Arg Ser Gly Ile Pro Ile Val Thr Ser Pro
                340                 345                 350
Tyr Gln Ile His Phe Thr Lys Thr Pro Lys Tyr Phe Lys Pro Gly Met
                355                 360                 365
Pro Phe Asp Leu Met Val Phe Val Thr Asn Pro Asp Gly Ser Pro Ala
                370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                405                 410                 415
Gln Lys Pro Leu Ser Ile Thr Val Arg Thr Lys Lys Gln Glu Leu Ser
                420                 425                 430
Glu Ala Glu Gln Ala Thr Arg Thr Met Gln Ala Leu Pro Tyr Ser Thr
                435                 440                 445
Val Gly Asn Ser Asn Asn Tyr Leu His Leu Ser Val Leu Arg Thr Glu
                450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                485                 490                 495
Lys Gly Arg Leu Leu Lys Ala Gly Arg Gln Val Arg Glu Pro Gly Gln
                500                 505                 510
Asp Leu Val Val Leu Pro Leu Ser Ile Thr Thr Asp Phe Ile Pro Ser
                515                 520                 525
Phe Arg Leu Val Ala Tyr Tyr Thr Leu Ile Gly Ala Ser Gly Gln Arg
                530                 535                 540
Glu Val Val Ala Asp Ser Val Trp Val Asp Val Lys Asp Ser Cys Val
545                 550                 555                 560
Gly Ser Leu Val Val Lys Ser Gly Gln Ser Glu Asp Arg Gln Pro Val
                565                 570                 575
Pro Gly Gln Gln Met Thr Leu Lys Ile Glu Gly Asp His Gly Ala Arg
                580                 585                 590
Val Val Leu Val Ala Val Asp Lys Gly Val Phe Val Leu Asn Lys Lys
                595                 600                 605
Asn Lys Leu Thr Gln Ser Lys Ile Trp Asp Val Glu Lys Ala Asp
                610                 615                 620
Ile Gly Cys Thr Pro Gly Ser Gly Lys Asp Tyr Ala Gly Val Phe Ser
625                 630                 635                 640
Asp Ala Gly Leu Thr Phe Thr Ser Ser Ser Gly Gln Gln Thr Ala Gln
                645                 650                 655
Arg Ala Glu Leu Gln Cys Pro Gln Pro Ala Ala Arg Arg Arg Arg Ser
                660                 665                 670
Val Gln Leu Thr Glu Lys Arg Met Asp Lys Val Gly Lys Tyr Pro Lys
                675                 680                 685
Glu Leu Arg Lys Cys Cys Glu Asp Gly Met Arg Glu Asn Pro Met Arg
                690                 695                 700
Phe Ser Cys Gln Arg Arg Thr Arg Phe Ile Ser Leu Gly Glu Ala Cys
705                 710                 715                 720
Lys Lys Val Phe Leu Asp Cys Cys Asn Tyr Ile Thr Glu Leu Arg Arg
                725                 730                 735
Gln His Ala Arg Ala Ser His Leu Gly Leu Ala Arg Ser Asn Leu Asp
                740                 745                 750
```

```
Glu Asp Ile Ile Ala Glu Glu Asn Ile Val Ser Arg Ser Glu Phe Pro
        755                 760                 765

Glu Ser Trp Leu Trp Asn Val Glu Asp Leu Lys Glu Pro Pro Lys Asn
770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
            805                 810                 815

Val Ala Asp Pro Phe Glu Val Thr Val Met Gln Asp Phe Phe Ile Asp
            820                 825                 830

Leu Arg Leu Pro Tyr Ser Val Val Arg Asn Glu Gln Val Glu Ile Arg
            835                 840                 845

Ala Val Leu Tyr Asn Tyr Arg Gln Asn Gln Glu Leu Lys Val Arg Val
        850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
            900                 905                 910

Lys Ala Ala Val Tyr His His Phe Ile Ser Asp Gly Val Arg Lys Ser
        915                 920                 925

Leu Lys Val Val Pro Glu Gly Ile Arg Met Asn Lys Thr Val Ala Val
        930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
            980                 985                 990

Asp Ala Val Asp Ala Glu Arg Leu Lys His Leu Ile Val Thr Pro Ser
        995                 1000                1005

Gly Cys Gly Glu Gln Asn Met Ile Gly Met Thr Pro Thr Val Ile
    1010                1015                1020

Ala Val His Tyr Leu Asp Glu Thr Glu Gln Trp Glu Lys Phe Gly
    1025                1030                1035

Leu Glu Lys Arg Gln Gly Ala Leu Glu Leu Ile Lys Lys Gly Tyr
    1040                1045                1050

Thr Gln Gln Leu Ala Phe Arg Gln Pro Ser Ser Ala Phe Ala Ala
    1055                1060                1065

Phe Val Lys Arg Ala Pro Ser Thr Trp Leu Thr Ala Tyr Val Val
    1070                1075                1080

Lys Val Phe Ser Leu Ala Val Asn Leu Ile Ala Ile Asp Ser Gln
    1085                1090                1095

Val Leu Cys Gly Ala Val Lys Trp Leu Ile Leu Glu Lys Gln Lys
    1100                1105                1110

Pro Asp Gly Val Phe Gln Glu Asp Ala Pro Val Ile His Gln Glu
    1115                1120                1125

Met Ile Gly Gly Leu Arg Asn Asn Asn Glu Lys Asp Met Ala Leu
    1130                1135                1140

Thr Ala Phe Val Leu Ile Ser Leu Gln Glu Ala Lys Asp Ile Cys
    1145                1150                1155
```

-continued

| | | | | | | | | | | | |
|---|---|---|---|---|---|---|---|---|---|---|---|
| Glu | Glu | Gln | Val | Asn | Ser | Leu | Pro | Gly | Ser | Ile | Thr | Lys | Ala | Gly |
| 1160 | | | | | 1165 | | | | | 1170 | | | | |

Asp Phe Leu Glu Ala Asn Tyr Met Asn Leu Gln Arg Ser Tyr Thr
1175 1180 1185

Val Ala Ile Ala Gly Tyr Ala Leu Ala Gln Met Gly Arg Leu Lys
1190 1195 1200

Gly Pro Leu Leu Asn Lys Phe Leu Thr Thr Ala Lys Asp Lys Asn
1205 1210 1215

Arg Trp Glu Asp Pro Gly Lys Gln Leu Tyr Asn Val Glu Ala Thr
1220 1225 1230

Ser Tyr Ala Leu Leu Ala Leu Leu Gln Leu Lys Asp Phe Asp Phe
1235 1240 1245

Val Pro Pro Val Val Arg Trp Leu Asn Glu Gln Arg Tyr Tyr Gly
1250 1255 1260

Gly Gly Tyr Gly Ser Thr Gln Ala Thr Phe Met Val Phe Gln Ala
1265 1270 1275

Leu Ala Gln Tyr Gln Lys Asp Ala Pro Asp His Gln Glu Leu Asn
1280 1285 1290

Leu Asp Val Ser Leu Gln Leu Pro Ser Arg Ser Ser Lys Ile Thr
1295 1300 1305

His Arg Ile His Trp Glu Ser Ala Ser Leu Leu Arg Ser Glu Glu
1310 1315 1320

Thr Lys Glu Asn Glu Gly Phe Thr Val Thr Ala Glu Gly Lys Gly
1325 1330 1335

Gln Gly Thr Leu Ser Val Val Thr Met Tyr His Ala Lys Ala Lys
1340 1345 1350

Asp Gln Leu Thr Cys Asn Lys Phe Asp Leu Lys Val Thr Ile Lys
1355 1360 1365

Pro Ala Pro Glu Thr Glu Lys Arg Pro Gln Asp Ala Lys Asn Thr
1370 1375 1380

Met Ile Leu Glu Ile Cys Thr Arg Tyr Arg Gly Asp Gln Asp Ala
1385 1390 1395

Thr Met Ser Ile Leu Asp Ile Ser Met Met Thr Gly Phe Ala Pro
1400 1405 1410

Asp Thr Asp Asp Leu Lys Gln Leu Ala Asn Gly Val Asp Arg Tyr
1415 1420 1425

Ile Ser Lys Tyr Glu Leu Asp Lys Ala Phe Ser Asp Arg Asn Thr
1430 1435 1440

Leu Ile Ile Tyr Leu Asp Lys Val Ser His Ser Glu Asp Asp Cys
1445 1450 1455

Leu Ala Phe Lys Val His Gln Tyr Phe Asn Val Glu Leu Ile Gln
1460 1465 1470

Pro Gly Ala Val Lys Val Tyr Ala Tyr Tyr Asn Leu Glu Glu Ser
1475 1480 1485

Cys Thr Arg Phe Tyr His Pro Glu Lys Glu Asp Gly Lys Leu Asn
1490 1495 1500

Lys Leu Cys Arg Asp Glu Leu Cys Arg Cys Ala Glu Glu Asn Cys
1505 1510 1515

Phe Ile Gln Lys Ser Asp Asp Lys Val Thr Leu Glu Glu Arg Leu
1520 1525 1530

Asp Lys Ala Cys Glu Pro Gly Val Asp Tyr Val Tyr Lys Thr Arg
1535 1540 1545

Leu Val Lys Val Gln Leu Ser Asn Asp Phe Asp Glu Tyr Ile Met

```
                1550                1555                1560

Ala Ile Glu Gln Thr Ile Lys Ser Gly Ser Asp Glu Val Gln Val
    1565                1570                1575

Gly Gln Gln Arg Thr Phe Ile Ser Pro Ile Lys Cys Arg Glu Ala
1580                1585                1590

Leu Lys Leu Glu Glu Lys Lys His Tyr Leu Met Trp Gly Leu Ser
    1595                1600                1605

Ser Asp Phe Trp Gly Glu Lys Pro Asn Leu Ser Tyr Ile Ile Gly
    1610                1615                1620

Lys Asp Thr Trp Val Glu His Trp Pro Glu Asp Glu Cys Gln
    1625                1630                1635

Asp Glu Glu Asn Gln Lys Gln Cys Gln Asp Leu Gly Ala Phe Thr
    1640                1645                1650

Glu Ser Met Val Val Phe Gly Cys Pro Asn
    1655                1660

<210> SEQ ID NO 3
<211> LENGTH: 418
<212> TYPE: PRT
<213> ORGANISM: Homo sapiens

<400> SEQUENCE: 3

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255
```

```
Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
            370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 4
<211> LENGTH: 114
<212> TYPE: PRT
<213> ORGANISM: Homo sapiens

<400> SEQUENCE: 4

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro

<210> SEQ ID NO 5
<211> LENGTH: 710
<212> TYPE: PRT
<213> ORGANISM: Homo sapiens

<400> SEQUENCE: 5

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser Gln
            20                  25                  30

Pro Glu Ala Thr Lys Cys Phe Gln Trp Gln Arg Asn Met Arg Lys Val
            35                  40                  45
```

-continued

Arg Gly Pro Pro Val Ser Cys Ile Lys Arg Asp Ser Pro Ile Gln Cys
        50                  55                  60

Ile Gln Ala Ile Ala Glu Asn Arg Ala Asp Ala Val Thr Leu Asp Gly
65                  70                  75                  80

Gly Phe Ile Tyr Glu Ala Gly Leu Ala Pro Tyr Lys Leu Arg Pro Val
                85                  90                  95

Ala Ala Glu Val Tyr Gly Thr Glu Arg Gln Pro Arg Thr His Tyr Tyr
            100                 105                 110

Ala Val Ala Val Val Lys Lys Gly Ser Phe Gln Leu Asn Glu Leu
            115                 120                 125

Gln Gly Leu Lys Ser Cys His Thr Gly Leu Arg Arg Thr Ala Gly Trp
        130                 135                 140

Asn Val Pro Ile Gly Thr Leu Arg Pro Phe Leu Asn Trp Thr Gly Pro
145                 150                 155                 160

Pro Glu Pro Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Ala Gly Thr Gly Glu Asn Lys Cys Ala Phe Ser Ser Gln Glu Pro Tyr
            195                 200                 205

Phe Ser Tyr Ser Gly Ala Phe Lys Cys Leu Arg Asp Gly Ala Gly Asp
    210                 215                 220

Val Ala Phe Ile Arg Glu Ser Thr Val Phe Glu Asp Leu Ser Asp Glu
225                 230                 235                 240

Ala Glu Arg Asp Glu Tyr Glu Leu Leu Cys Pro Asp Asn Thr Arg Lys
                245                 250                 255

Pro Val Asp Lys Phe Lys Asp Cys His Leu Ala Arg Val Pro Ser His
            260                 265                 270

Ala Val Val Ala Arg Ser Val Asn Gly Lys Glu Asp Ala Ile Trp Asn
        275                 280                 285

Leu Leu Arg Gln Ala Gln Glu Lys Phe Gly Lys Asp Lys Ser Pro Lys
        290                 295                 300

Phe Gln Leu Phe Gly Ser Pro Ser Gly Gln Lys Asp Leu Leu Phe Lys
305                 310                 315                 320

Asp Ser Ala Ile Gly Phe Ser Arg Val Pro Pro Arg Ile Asp Ser Gly
                325                 330                 335

Leu Tyr Leu Gly Ser Gly Tyr Phe Thr Ala Ile Gln Asn Leu Arg Lys
            340                 345                 350

Ser Glu Glu Glu Val Ala Ala Arg Ala Arg Val Trp Cys Ala
            355                 360                 365

Val Gly Glu Gln Glu Leu Arg Lys Cys Asn Gln Trp Ser Gly Leu Ser
        370                 375                 380

Glu Gly Ser Val Thr Cys Ser Ser Ala Ser Thr Thr Glu Asp Cys Ile
385                 390                 395                 400

Ala Leu Val Leu Lys Gly Glu Ala Asp Ala Met Ser Leu Asp Gly Gly
                405                 410                 415

Tyr Val Tyr Thr Ala Gly Lys Cys Gly Leu Val Pro Val Leu Ala Glu
            420                 425                 430

Asn Tyr Lys Ser Gln Gln Ser Ser Asp Pro Asp Pro Asn Cys Val Asp
        435                 440                 445

Arg Pro Val Glu Gly Tyr Leu Ala Val Ala Val Val Arg Arg Ser Asp
        450                 455                 460

```
Thr Ser Leu Thr Trp Asn Ser Val Lys Gly Lys Ser Cys His Thr
465                 470                 475                 480

Ala Val Asp Arg Thr Ala Gly Trp Asn Ile Pro Met Gly Leu Leu Phe
            485                 490                 495

Asn Gln Thr Gly Ser Cys Lys Phe Asp Glu Tyr Phe Ser Gln Ser Cys
        500                 505                 510

Ala Pro Gly Ser Asp Pro Arg Ser Asn Leu Cys Ala Leu Cys Ile Gly
    515                 520                 525

Asp Glu Gln Gly Glu Asn Lys Cys Val Pro Asn Ser Asn Glu Arg Tyr
530                 535                 540

Tyr Gly Tyr Thr Gly Ala Phe Arg Cys Leu Ala Glu Asn Ala Gly Asp
545                 550                 555                 560

Val Ala Phe Val Lys Asp Val Thr Val Leu Gln Asn Thr Asp Gly Asn
                565                 570                 575

Asn Asn Glu Ala Trp Ala Lys Asp Leu Lys Leu Ala Asp Phe Ala Leu
            580                 585                 590

Leu Cys Leu Asp Gly Lys Arg Lys Pro Val Thr Glu Ala Arg Ser Cys
        595                 600                 605

His Leu Ala Met Ala Pro Asn His Ala Val Val Ser Arg Met Asp Lys
    610                 615                 620

Val Glu Arg Leu Lys Gln Val Leu Leu His Gln Gln Ala Lys Phe Gly
625                 630                 635                 640

Arg Asn Gly Ser Asp Cys Pro Asp Lys Phe Cys Leu Phe Gln Ser Glu
                645                 650                 655

Thr Lys Asn Leu Leu Phe Asn Asp Asn Thr Glu Cys Leu Ala Arg Leu
            660                 665                 670

His Gly Lys Thr Thr Tyr Glu Lys Tyr Leu Gly Pro Gln Tyr Val Ala
        675                 680                 685

Gly Ile Thr Asn Leu Lys Lys Cys Ser Thr Ser Pro Leu Leu Glu Ala
    690                 695                 700

Cys Glu Phe Leu Arg Lys
705                 710

<210> SEQ ID NO 6
<211> LENGTH: 379
<212> TYPE: PRT
<213> ORGANISM: Homo sapiens

<400> SEQUENCE: 6

Met Glu Gln Leu Ser Ser Ala Asn Thr Arg Phe Ala Leu Asp Leu Phe
1               5                   10                  15

Leu Ala Leu Ser Glu Asn Asn Pro Ala Gly Asn Ile Phe Ile Ser Pro
            20                  25                  30

Phe Ser Ile Ser Ser Ala Met Ala Met Val Phe Leu Gly Thr Arg Gly
        35                  40                  45

Asn Thr Ala Ala Gln Leu Ser Lys Thr Phe His Phe Asn Thr Val Glu
    50                  55                  60

Glu Val His Ser Arg Phe Gln Ser Leu Asn Ala Asp Ile Asn Lys Arg
65                  70                  75                  80

Gly Ala Ser Tyr Ile Leu Lys Leu Ala Asn Arg Leu Tyr Gly Glu Lys
                85                  90                  95

Thr Tyr Asn Phe Leu Pro Glu Phe Leu Val Ser Thr Gln Lys Thr Tyr
            100                 105                 110

Gly Ala Asp Leu Ala Ser Val Asp Phe Gln His Ala Ser Glu Asp Ala
        115                 120                 125
```

-continued

Arg Lys Thr Ile Asn Gln Trp Val Lys Gly Gln Thr Glu Gly Lys Ile
130                 135                 140

Pro Glu Leu Leu Ala Ser Gly Met Val Asp Asn Met Thr Lys Leu Val
145                 150                 155                 160

Leu Val Asn Ala Ile Tyr Phe Lys Gly Asn Trp Lys Asp Lys Phe Met
                165                 170                 175

Lys Glu Ala Thr Thr Asn Ala Pro Phe Arg Leu Asn Lys Lys Asp Arg
            180                 185                 190

Lys Thr Val Lys Met Met Tyr Gln Lys Lys Phe Ala Tyr Gly Tyr
        195                 200                 205

Ile Glu Asp Leu Lys Cys Arg Val Leu Glu Leu Pro Tyr Gln Gly Glu
210                 215                 220

Glu Leu Ser Met Val Ile Leu Leu Pro Asp Asp Ile Glu Asp Glu Ser
225                 230                 235                 240

Thr Gly Leu Lys Lys Ile Glu Glu Gln Leu Thr Leu Glu Lys Leu His
                245                 250                 255

Glu Trp Thr Lys Pro Glu Asn Leu Asp Phe Ile Glu Val Asn Val Ser
            260                 265                 270

Leu Pro Arg Phe Lys Leu Glu Glu Ser Tyr Thr Leu Asn Ser Asp Leu
        275                 280                 285

Ala Arg Leu Gly Val Gln Asp Leu Phe Asn Ser Ser Lys Ala Asp Leu
290                 295                 300

Ser Gly Met Ser Gly Ala Arg Asp Ile Phe Ile Ser Lys Ile Val His
305                 310                 315                 320

Lys Ser Phe Val Glu Val Asn Glu Glu Gly Thr Glu Ala Ala Ala Ala
                325                 330                 335

Thr Ala Gly Ile Ala Thr Phe Cys Met Leu Met Pro Glu Glu Asn Phe
            340                 345                 350

Thr Ala Asp His Pro Phe Leu Phe Phe Ile Arg His Asn Ser Ser Gly
        355                 360                 365

Ser Ile Leu Phe Leu Gly Arg Phe Ser Ser Pro
370                 375

<210> SEQ ID NO 7
<211> LENGTH: 464
<212> TYPE: PRT
<213> ORGANISM: Homo sapiens

<400> SEQUENCE: 7

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
                20                  25                  30

His Gly Ser Pro Val Asp Ile Cys Thr Ala Lys Pro Arg Asp Ile Pro
            35                  40                  45

Met Asn Pro Met Cys Ile Tyr Arg Ser Pro Glu Lys Lys Ala Thr Glu
        50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn

```
            115                 120                 125
Asp Thr Leu Gln Gln Leu Met Glu Val Phe Lys Phe Asp Thr Ile Ser
        130                 135                 140

Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Ser Leu Asn Pro Asn Arg Val
            420                 425                 430

Thr Phe Lys Ala Asn Arg Pro Phe Leu Val Phe Ile Arg Glu Val Pro
        435                 440                 445

Leu Asn Thr Ile Ile Phe Met Gly Arg Val Ala Asn Pro Cys Val Lys
    450                 455                 460

<210> SEQ ID NO 8
<211> LENGTH: 142
<212> TYPE: PRT
<213> ORGANISM: Homo sapiens

<400> SEQUENCE: 8

Met Val Leu Ser Pro Ala Asp Lys Thr Asn Val Lys Ala Ala Trp Gly
1               5                   10                  15

Lys Val Gly Ala His Ala Gly Glu Tyr Gly Ala Glu Ala Leu Glu Arg
            20                  25                  30
```

```
Met Phe Leu Ser Phe Pro Thr Thr Lys Thr Tyr Phe Pro His Phe Asp
         35                  40                  45

Leu Ser His Gly Ser Ala Gln Val Lys Gly His Gly Lys Lys Val Ala
     50                  55                  60

Asp Ala Leu Thr Asn Ala Val Ala His Val Asp Asp Met Pro Asn Ala
 65                  70                  75                  80

Leu Ser Ala Leu Ser Asp Leu His Ala His Lys Leu Arg Val Asp Pro
                 85                  90                  95

Val Asn Phe Lys Leu Leu Ser His Cys Leu Leu Val Thr Leu Ala Ala
             100                 105                 110

His Leu Pro Ala Glu Phe Thr Pro Ala Val His Ala Ser Leu Asp Lys
         115                 120                 125

Phe Leu Ala Ser Val Ser Thr Val Leu Thr Ser Lys Tyr Arg
     130                 135                 140

<210> SEQ ID NO 9
<211> LENGTH: 147
<212> TYPE: PRT
<213> ORGANISM: Homo sapiens

<400> SEQUENCE: 9

Met Val His Leu Thr Pro Glu Glu Lys Ser Ala Val Thr Ala Leu Trp
 1               5                  10                  15

Gly Lys Val Asn Val Asp Glu Val Gly Gly Glu Ala Leu Gly Arg Leu
             20                  25                  30

Leu Val Val Tyr Pro Trp Thr Gln Arg Phe Phe Glu Ser Phe Gly Asp
         35                  40                  45

Leu Ser Thr Pro Asp Ala Val Met Gly Asn Pro Lys Val Lys Ala His
     50                  55                  60

Gly Lys Lys Val Leu Gly Ala Phe Ser Asp Gly Leu Ala His Leu Asp
 65                  70                  75                  80

Asn Leu Lys Gly Thr Phe Ala Thr Leu Ser Glu Leu His Cys Asp Lys
                 85                  90                  95

Leu His Val Asp Pro Glu Asn Phe Arg Leu Leu Gly Asn Val Leu Val
             100                 105                 110

Cys Val Leu Ala His His Phe Gly Lys Glu Phe Thr Pro Pro Val Gln
         115                 120                 125

Ala Ala Tyr Gln Lys Val Val Ala Gly Val Ala Asn Ala Leu Ala His
     130                 135                 140

Lys Tyr His
145

<210> SEQ ID NO 10
<211> LENGTH: 147
<212> TYPE: PRT
<213> ORGANISM: Homo sapiens

<400> SEQUENCE: 10

Met Val His Leu Thr Pro Glu Glu Lys Thr Ala Val Asn Ala Leu Trp
 1               5                  10                  15

Gly Lys Val Asn Val Asp Ala Val Gly Gly Glu Ala Leu Gly Arg Leu
             20                  25                  30

Leu Val Val Tyr Pro Trp Thr Gln Arg Phe Phe Glu Ser Phe Gly Asp
         35                  40                  45

Leu Ser Ser Pro Asp Ala Val Met Gly Asn Pro Lys Val Lys Ala His
     50                  55                  60
```

```
Gly Lys Lys Val Leu Gly Ala Phe Ser Asp Gly Leu Ala His Leu Asp
 65                  70                  75                  80

Asn Leu Lys Gly Thr Phe Ser Gln Leu Ser Glu Leu His Cys Asp Lys
                 85                  90                  95

Leu His Val Asp Pro Glu Asn Phe Arg Leu Leu Gly Asn Val Leu Val
             100                 105                 110

Cys Val Leu Ala Arg Asn Phe Gly Lys Glu Phe Thr Pro Gln Met Gln
         115                 120                 125

Ala Ala Tyr Gln Lys Val Val Ala Gly Val Ala Asn Ala Leu Ala His
     130                 135                 140

Lys Tyr His
145

<210> SEQ ID NO 11
<211> LENGTH: 146
<212> TYPE: PRT
<213> ORGANISM: Homo sapiens

<400> SEQUENCE: 11

Met Arg Leu Leu Gln Leu Leu Phe Arg Ala Ser Pro Ala Thr Leu Leu
 1               5                  10                  15

Leu Val Leu Cys Leu Gln Leu Gly Ala Asn Lys Ala Gln Asp Asn Thr
                 20                  25                  30

Arg Lys Ile Ile Ile Lys Asn Phe Asp Ile Pro Lys Ser Val Arg Pro
             35                  40                  45

Asn Asp Glu Val Thr Ala Val Leu Ala Val Gln Thr Glu Leu Lys Glu
         50                  55                  60

Cys Met Val Val Lys Thr Tyr Leu Ile Ser Ser Ile Pro Leu Gln Gly
 65                  70                  75                  80

Ala Phe Asn Tyr Lys Tyr Thr Ala Cys Leu Cys Asp Asp Asn Pro Lys
                 85                  90                  95

Thr Phe Tyr Trp Asp Phe Tyr Thr Asn Arg Thr Val Gln Ile Ala Ala
             100                 105                 110

Val Val Asp Val Ile Arg Glu Leu Gly Ile Cys Pro Asp Asp Ala Ala
         115                 120                 125

Val Ile Pro Ile Lys Asn Asn Arg Phe Tyr Thr Ile Glu Ile Leu Lys
     130                 135                 140

Val Glu
145

<210> SEQ ID NO 12
<211> LENGTH: 511
<212> TYPE: PRT
<213> ORGANISM: Homo sapiens

<400> SEQUENCE: 12

Met Lys Leu Phe Trp Leu Leu Phe Thr Ile Gly Phe Cys Trp Ala Gln
 1               5                  10                  15

Tyr Ser Ser Asn Thr Gln Gln Gly Arg Thr Ser Ile Val His Leu Phe
                 20                  25                  30

Glu Trp Arg Trp Val Asp Ile Ala Leu Glu Cys Glu Arg Tyr Leu Ala
             35                  40                  45

Pro Lys Gly Phe Gly Gly Val Gln Val Ser Pro Asn Glu Asn Val
         50                  55                  60

Ala Ile His Asn Pro Phe Arg Pro Trp Trp Glu Arg Tyr Gln Pro Val
 65                  70                  75                  80
```

```
Ser Tyr Lys Leu Cys Thr Arg Ser Gly Asn Glu Asp Glu Phe Arg Asn
                85                  90                  95

Met Val Thr Arg Cys Asn Asn Val Gly Val Arg Ile Tyr Val Asp Ala
            100                 105                 110

Val Ile Asn His Met Cys Gly Asn Ala Val Ser Ala Gly Thr Ser Ser
        115                 120                 125

Thr Cys Gly Ser Tyr Phe Asn Pro Gly Ser Arg Asp Phe Pro Ala Val
    130                 135                 140

Pro Tyr Ser Gly Trp Asp Phe Asn Asp Gly Lys Cys Lys Thr Gly Ser
145                 150                 155                 160

Gly Asp Ile Glu Asn Tyr Asn Asp Ala Thr Gln Val Arg Asp Cys Arg
                165                 170                 175

Leu Ser Gly Leu Leu Asp Leu Ala Leu Gly Lys Asp Tyr Val Arg Ser
            180                 185                 190

Lys Ile Ala Glu Tyr Met Asn His Leu Ile Asp Ile Gly Val Ala Gly
        195                 200                 205

Phe Arg Ile Asp Ala Ser Lys His Met Trp Pro Gly Asp Ile Lys Ala
    210                 215                 220

Ile Leu Asp Lys Leu His Asn Leu Asn Ser Asn Trp Phe Pro Glu Gly
225                 230                 235                 240

Ser Lys Pro Phe Ile Tyr Gln Glu Val Ile Asp Leu Gly Gly Glu Pro
                245                 250                 255

Ile Lys Ser Ser Asp Tyr Phe Gly Asn Gly Arg Val Thr Glu Phe Lys
            260                 265                 270

Tyr Gly Ala Lys Leu Gly Thr Val Ile Arg Lys Trp Asn Gly Glu Lys
        275                 280                 285

Met Ser Tyr Leu Lys Asn Trp Gly Glu Gly Trp Gly Phe Met Pro Ser
    290                 295                 300

Asp Arg Ala Leu Val Phe Val Asp Asn His Asp Asn Gln Arg Gly His
305                 310                 315                 320

Gly Ala Gly Gly Ala Ser Ile Leu Thr Phe Trp Asp Ala Arg Leu Tyr
                325                 330                 335

Lys Met Ala Val Gly Phe Met Leu Ala His Pro Tyr Gly Phe Thr Arg
            340                 345                 350

Val Met Ser Ser Tyr Arg Trp Pro Arg Tyr Phe Glu Asn Gly Lys Asp
        355                 360                 365

Val Asn Asp Trp Val Gly Pro Pro Asn Asp Asn Gly Val Thr Lys Glu
    370                 375                 380

Val Thr Ile Asn Pro Asp Thr Thr Cys Gly Asn Asp Trp Val Cys Glu
385                 390                 395                 400

His Arg Trp Arg Gln Ile Arg Asn Met Val Asn Phe Arg Asn Val Val
                405                 410                 415

Asp Gly Gln Pro Phe Thr Asn Trp Tyr Asp Asn Gly Ser Asn Gln Val
            420                 425                 430

Ala Phe Gly Arg Gly Asn Arg Gly Phe Ile Val Phe Asn Asn Asp Asp
        435                 440                 445

Trp Thr Phe Ser Leu Thr Leu Gln Thr Gly Leu Pro Ala Gly Thr Tyr
    450                 455                 460

Cys Asp Val Ile Ser Gly Asp Lys Ile Asn Gly Asn Cys Thr Gly Ile
465                 470                 475                 480

Lys Ile Tyr Val Ser Asp Asp Gly Lys Ala His Phe Ser Ile Ser Asn
                485                 490                 495

Ser Ala Glu Asp Pro Phe Ile Ala Ile His Ala Glu Ser Lys Leu
```

<210> SEQ ID NO 13
<211> LENGTH: 109
<212> TYPE: PRT
<213> ORGANISM: Homo sapiens

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Asp Asp Phe Ala Val Tyr Tyr Cys Gln Gln Tyr Gly Ser Ser Pro
                85                  90                  95

Gln Thr Phe Gly Gln Gly Ser Lys Val Glu Ile Lys Arg
            100                 105

<210> SEQ ID NO 14
<211> LENGTH: 340
<212> TYPE: PRT
<213> ORGANISM: Homo sapiens

<400> SEQUENCE: 14

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser

```
            210                 215                 220
Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 15
<211> LENGTH: 330
<212> TYPE: PRT
<213> ORGANISM: Homo sapiens

<400> SEQUENCE: 15

Met Ala Phe Leu Pro Ser Trp Val Cys Val Leu Val Gly Ser Phe Ser
1               5                   10                  15

Ala Ser Leu Ala Gly Thr Ser Asn Leu Ser Glu Thr Glu Pro Pro Leu
            20                  25                  30

Trp Lys Glu Ser Pro Gly Gln Leu Ser Asp Tyr Arg Val Glu Asn Ser
        35                  40                  45

Met Tyr Ile Ile Asn Pro Trp Val Tyr Leu Glu Arg Met Gly Met Tyr
    50                  55                  60

Lys Ile Ile Leu Asn Gln Thr Ala Arg Tyr Phe Ala Lys Phe Ala Pro
65                  70                  75                  80

Asp Asn Glu Gln Asn Ile Leu Trp Gly Leu Pro Leu Gln Tyr Gly Trp
                85                  90                  95

Gln Tyr Arg Thr Gly Arg Leu Ala Asp Pro Thr Arg Arg Thr Asn Cys
            100                 105                 110

Gly Tyr Glu Ser Gly Asp His Met Cys Ile Ser Val Asp Ser Trp Trp
        115                 120                 125

Ala Asp Leu Asn Tyr Phe Leu Ser Ser Leu Pro Phe Leu Ala Ala Val
    130                 135                 140

Asp Ser Gly Val Met Gly Ile Ser Ser Asp Gln Val Arg Leu Leu Pro
145                 150                 155                 160

Pro Pro Lys Asn Glu Arg Lys Phe Cys Tyr Asp Val Ser Ser Cys Arg
                165                 170                 175

Ser Ser Phe Pro Glu Thr Met Asn Lys Trp Asn Thr Phe Tyr Gln Tyr
            180                 185                 190

Leu Gln Ser Pro Phe Ser Lys Phe Asp Asp Leu Leu Lys Tyr Leu Trp
        195                 200                 205

Ala Ala His Thr Ser Thr Leu Ala Asp Asn Ile Lys Ser Phe Glu Asp
    210                 215                 220

Arg Tyr Asp Tyr Tyr Ser Lys Ala Glu Ala His Phe Glu Arg Ser Trp
225                 230                 235                 240
```

```
Val Leu Ala Val Asp His Leu Ala Ala Val Leu Phe Pro Thr Thr Leu
                245                 250                 255

Ile Arg Ser Tyr Lys Phe Gln Lys Gly Met Pro Pro Arg Ile Leu Leu
            260                 265                 270

Asn Thr Asp Val Ala Pro Phe Ile Ser Asp Phe Thr Ala Phe Gln Asn
            275                 280                 285

Val Val Leu Val Leu Leu Asn Met Leu Asp Asn Val Asp Lys Ser Ile
        290                 295                 300

Gly Tyr Leu Cys Thr Glu Lys Ser Asn Val Tyr Arg Asp His Ser Glu
305                 310                 315                 320

Ser Ser Ser Arg Ser Tyr Gly Asn Asn Ser
            325                 330
```

<210> SEQ ID NO 16
<211> LENGTH: 390
<212> TYPE: PRT
<213> ORGANISM: Homo sapiens

<400> SEQUENCE: 16

```
Met Asn Ser Leu Ser Glu Ala Asn Thr Lys Phe Met Phe Asp Leu Phe
1               5                   10                  15

Gln Gln Phe Arg Lys Ser Lys Glu Asn Asn Ile Phe Tyr Ser Pro Ile
            20                  25                  30

Ser Ile Thr Ser Ala Leu Gly Met Val Leu Leu Gly Ala Lys Asp Asn
            35                  40                  45

Thr Ala Gln Gln Ile Lys Lys Val Leu His Phe Asp Gln Val Thr Glu
    50                  55                  60

Asn Thr Thr Gly Lys Ala Ala Thr Tyr His Val Asp Arg Ser Gly Asn
65                  70                  75                  80

Val His His Gln Phe Gln Lys Leu Leu Thr Glu Phe Asn Lys Ser Thr
                85                  90                  95

Asp Ala Tyr Glu Leu Lys Ile Ala Asn Lys Leu Phe Gly Glu Lys Thr
            100                 105                 110

Tyr Leu Phe Leu Gln Glu Tyr Leu Asp Ala Ile Lys Lys Phe Tyr Gln
        115                 120                 125

Thr Ser Val Glu Ser Val Asp Phe Ala Asn Ala Pro Glu Glu Ser Arg
    130                 135                 140

Lys Lys Ile Asn Ser Trp Val Glu Ser Gln Thr Asn Glu Lys Ile Lys
145                 150                 155                 160

Asn Leu Ile Pro Glu Gly Asn Ile Gly Ser Asn Thr Thr Leu Val Leu
                165                 170                 175

Val Asn Ala Ile Tyr Phe Lys Gly Gln Trp Glu Lys Lys Phe Asn Lys
            180                 185                 190

Glu Asp Thr Lys Glu Lys Phe Trp Pro Asn Lys Asn Thr Tyr Lys
        195                 200                 205

Ser Ile Gln Met Met Arg Gln Tyr Thr Ser Phe His Phe Ala Ser Leu
    210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Lys
                245                 250                 255

Leu Glu Glu Lys Leu Thr Ala Glu Lys Leu Met Glu Trp Thr Ser Leu
            260                 265                 270

Gln Asn Met Arg Glu Thr Arg Val Asp Leu His Leu Pro Arg Phe Lys
        275                 280                 285
```

```
Val Glu Glu Ser Tyr Asp Leu Lys Asp Thr Leu Arg Thr Met Gly Met
        290                 295                 300

Val Asp Ile Phe Asn Gly Asp Ala Asp Leu Ser Gly Met Thr Gly Ser
305                 310                 315                 320

Arg Gly Leu Val Leu Ser Gly Val Leu His Lys Ala Phe Val Glu Val
                325                 330                 335

Thr Glu Glu Gly Ala Glu Ala Ala Ala Thr Ala Val Val Gly Phe
        340                 345                 350

Gly Ser Ser Pro Thr Ser Thr Asn Glu Glu Phe His Cys Asn His Pro
        355                 360                 365

Phe Leu Phe Phe Ile Arg Gln Asn Lys Thr Asn Ser Ile Leu Phe Tyr
370                 375                 380

Gly Arg Phe Ser Ser Pro
385                 390
```

<210> SEQ ID NO 17
<211> LENGTH: 191
<212> TYPE: PRT
<213> ORGANISM: Homo sapiens

<400> SEQUENCE: 17

```
Met Gly Thr Trp Ile Leu Phe Ala Cys Leu Leu Gly Ala Ala Phe Ala
1               5                   10                  15

Met Pro Leu Pro Pro His Pro Gly His Pro Gly Tyr Ile Asn Phe Ser
                20                  25                  30

Tyr Glu Val Leu Thr Pro Leu Lys Trp Tyr Gln Ser Ile Arg Pro Pro
            35                  40                  45

Tyr Pro Ser Tyr Gly Tyr Glu Pro Met Gly Gly Trp Leu His His Gln
50                  55                  60

Ile Ile Pro Val Leu Ser Gln Gln His Pro Thr His Thr Leu Gln
65                  70                  75                  80

Pro His His His Ile Pro Val Val Pro Ala Gln Gln Pro Val Ile Pro
                85                  90                  95

Gln Gln Pro Met Met Pro Val Pro Gly Gln His Ser Met Thr Pro Ile
            100                 105                 110

Gln His His Gln Pro Asn Leu Pro Pro Ala Gln Gln Pro Tyr Gln
        115                 120                 125

Pro Gln Pro Val Gln Pro Gln Pro His Gln Pro Met Gln Pro Gln Pro
130                 135                 140

Pro Val His Pro Met Gln Pro Leu Pro Pro Gln Pro Pro Leu Pro Pro
145                 150                 155                 160

Met Phe Pro Met Gln Pro Leu Pro Pro Met Leu Pro Asp Leu Thr Leu
                165                 170                 175

Glu Ala Trp Pro Ser Thr Asp Lys Thr Lys Arg Glu Glu Val Asp
            180                 185                 190
```

<210> SEQ ID NO 18
<211> LENGTH: 206
<212> TYPE: PRT
<213> ORGANISM: Homo sapiens

<400> SEQUENCE: 18

```
Met Gly Thr Trp Ile Leu Phe Ala Cys Leu Leu Gly Ala Ala Phe Ala
1               5                   10                  15

Met Pro Leu Pro Pro His Pro Gly His Pro Gly Tyr Ile Asn Phe Ser
                20                  25                  30
```

```
Tyr Glu Asn Ser His Ser Gln Ala Ile Asn Val Asp Arg Ile Ala Leu
            35                  40                  45

Val Leu Thr Pro Leu Lys Trp Tyr Gln Ser Met Ile Arg Pro Pro Tyr
 50                  55                  60

Ser Ser Tyr Gly Tyr Glu Pro Met Gly Gly Trp Leu His His Gln Ile
 65                  70                  75                  80

Ile Pro Val Val Ser Gln Gln His Pro Leu Thr His Thr Leu Gln Ser
                85                  90                  95

His His His Ile Pro Val Val Pro Ala Gln Gln Pro Arg Val Arg Gln
            100                 105                 110

Gln Ala Leu Met Pro Val Pro Gly Gln Gln Ser Met Thr Pro Thr Gln
            115                 120                 125

His His Gln Pro Asn Leu Pro Leu Pro Ala Gln Gln Pro Phe Gln Pro
            130                 135                 140

Gln Pro Val Gln Pro Gln Pro His Gln Pro Met Gln Pro Gln Pro Pro
145                 150                 155                 160

Val Gln Pro Met Gln Pro Leu Leu Pro Gln Pro Pro Leu Pro Pro Met
                165                 170                 175

Phe Pro Leu Arg Pro Leu Pro Pro Ile Leu Pro Asp Leu His Leu Glu
                180                 185                 190

Ala Trp Pro Ala Thr Asp Lys Thr Lys Gln Glu Glu Val Asp
            195                 200                 205

<210> SEQ ID NO 19
<211> LENGTH: 210
<212> TYPE: PRT
<213> ORGANISM: Mus musculus

<400> SEQUENCE: 19

Met Gly Thr Trp Ile Leu Phe Ala Cys Leu Leu Gly Ala Ala Phe Ala
 1                   5                  10                  15

Met Pro Leu Pro Pro His Pro Gly Ser Pro Gly Tyr Ile Asn Leu Ser
                20                  25                  30

Tyr Glu Lys Ser His Ser Gln Ala Ile Asn Thr Asp Arg Thr Ala Leu
            35                  40                  45

Val Leu Thr Pro Leu Lys Trp Tyr Gln Ser Met Ile Arg Gln Pro Tyr
 50                  55                  60

Pro Ser Tyr Gly Tyr Glu Pro Met Gly Gly Trp Leu His His Gln Ile
 65                  70                  75                  80

Ile Pro Val Leu Ser Gln Gln His Pro Ser His Thr Leu Gln Pro
                85                  90                  95

His His His Leu Pro Val Val Pro Ala Gln Gln Pro Val Ala Pro Gln
            100                 105                 110

Gln Pro Met Met Pro Val Pro Gly His His Ser Met Thr Pro Thr Gln
            115                 120                 125

His His Gln Pro Asn Ile Pro Pro Ser Ala Gln Gln Pro Phe Gln Gln
            130                 135                 140

Pro Phe Gln Pro Gln Ala Ile Pro Pro Gln Ser His Gln Pro Met Gln
145                 150                 155                 160

Pro Gln Ser Pro Leu His Pro Met Gln Pro Leu Ala Pro Gln Pro Pro
                165                 170                 175

Leu Pro Pro Leu Phe Ser Met Gln Pro Leu Ser Pro Ile Leu Pro Glu
                180                 185                 190
```

Leu Pro Leu Glu Ala Trp Pro Ala Thr Asp Lys Thr Lys Arg Glu Glu
            195                 200                 205

Val Asp
    210

<210> SEQ ID NO 20
<211> LENGTH: 142
<212> TYPE: PRT
<213> ORGANISM: Bos Taurus

<400> SEQUENCE: 20

Met Val Leu Ser Ala Ala Asp Lys Gly Asn Val Lys Ala Ala Trp Gly
1               5                   10                  15

Lys Val Gly Gly His Ala Ala Glu Tyr Gly Ala Glu Ala Leu Glu Arg
            20                  25                  30

Met Phe Leu Ser Phe Pro Thr Thr Lys Thr Tyr Phe Pro His Phe Asp
        35                  40                  45

Leu Ser His Gly Ser Ala Gln Val Lys Gly His Gly Ala Lys Val Ala
    50                  55                  60

Ala Ala Leu Thr Lys Ala Val Glu His Leu Asp Asp Leu Pro Gly Ala
65                  70                  75                  80

Leu Ser Glu Leu Ser Asp Leu His Ala His Lys Leu Arg Val Asp Pro
                85                  90                  95

Val Asn Phe Lys Leu Leu Ser His Ser Leu Leu Val Thr Leu Ala Ser
            100                 105                 110

His Leu Pro Ser Asp Phe Thr Pro Ala Val His Ala Ser Leu Asp Lys
        115                 120                 125

Phe Leu Ala Asn Val Ser Thr Val Leu Thr Ser Lys Tyr Arg
    130                 135                 140

<210> SEQ ID NO 21
<211> LENGTH: 145
<212> TYPE: PRT
<213> ORGANISM: Bos Taurus

<400> SEQUENCE: 21

Met Leu Thr Ala Glu Glu Lys Ala Ala Val Thr Ala Phe Trp Gly Lys
1               5                   10                  15

Val Lys Val Asp Glu Val Gly Gly Glu Ala Leu Gly Arg Leu Leu Val
            20                  25                  30

Val Tyr Pro Trp Thr Gln Arg Phe Phe Glu Ser Phe Gly Asp Leu Ser
        35                  40                  45

Thr Ala Asp Ala Val Met Asn Asn Pro Lys Val Lys Ala His Gly Lys
    50                  55                  60

Lys Val Leu Asp Ser Phe Ser Asn Gly Met Lys His Leu Asp Asp Leu
65                  70                  75                  80

Lys Gly Thr Phe Ala Ala Leu Ser Glu Leu His Cys Asp Lys Leu His
                85                  90                  95

Val Asp Pro Glu Asn Phe Lys Leu Leu Gly Asn Val Leu Val Val Val
            100                 105                 110

Leu Ala Arg Asn Phe Gly Lys Glu Phe Thr Pro Val Leu Gln Ala Asp
        115                 120                 125

```
Phe Gln Lys Val Val Ala Gly Val Ala Asn Ala Leu Ala His Arg Tyr
    130                 135                 140
His
145
```

KIT AND METHOD FOR DETECTING POROUS DENTAL HYDROXYAPATITE

This application is a divisional of and claims priority to U.S. application Ser. No. 13/501,676 filed Oct. 4, 2012; International Application No. PCT/AU2011/000303 filed Mar. 18, 2011; and Australian Application No. 2010901171 filed Mar. 19, 2010; the entire contents of each are incorporated herein by reference.

FIELD

The invention relates to a kit and a probe for detecting porous dental hydroxyapatite and a method for detecting a condition involving porous dental hydroxyapatite.

BACKGROUND

The resilience of teeth depends on a complex interplay between mineral (termed hydroxyapatite) and organic components (proteins, cells and tissues). Under normal conditions the hydroxyapatite in enamel and dentine is organised into an extraordinarily dense structure that confers the hardness and toughness required for maintenance of the tooth's integrity. Loss of mineral-density in enamel and dentine results in abnormally porous hydroxyapatite, which compromises the tooth's physical resilience and can lead to structural failure. Porous hydroxyapatite is caused by several prevalent conditions, including dental caries and developmental dental defects (DDD).

Dental caries (tooth decay) is a disease caused by bacteria that secrete acid. The acid produced by cariogenic bacteria can dissolve hydroxyapatite in a process termed demineralisation. The initial process of demineralisation (termed incipient caries) leads to discrete regions of porous hydroxyapatite termed white spot lesions. Over time, a white-spot lesion may progress to a cavity (i.e. loss of tooth material) or it may stall (termed inactive caries) and re-form a dense hydroxyapatite shell in a process called remineralisation. Before a cavity forms, the process is reversible (i.e. remineralisation), but once enamel is lost it cannot be regenerated.

Caries is diagnosed by a combination of visual inspection, physical challenge (e.g. scratching with dental probe), and X-ray radiography (to detect caries between teeth or beneath the gum line). Worryingly, these diagnostic approaches miss approximately half of early caries, and up to 13% of teeth diagnosed as carious with these methods are in fact caries-free. Recent attempts at improving diagnosis include use of equipment that measures electrical impedance, quantitative light-induced fluorescence (QLF) and infrared laser fluorescence (DIAGNOdent®), but none have found widespread use because of the cost and size of apparatus, and problems with inter-individual variation. Another approach has been the use of dyes to detect dental caries in dentine. However, these dyes are not selective for porous hydroxyapatite: they bind to proteins (presumed to be associated with infecting bacteria in dentine) or they occupy interstitial space, which reduces specificity and sensitivity. Moreover, these dyes cause the oral cavity to become discoloured, bind to healthy teeth, or require visualisation with an irradiator.

There are two main treatments for caries, the selection of which is dictated by the extent of disease. White spot lesions may be treated with remineralisation approaches (e.g. fluoride therapy or amorphous calcium phosphate stabilised with bioactive molecules). Cavities require conventional restorative dentistry (i.e. fillings).

DDD are another common cause of porous hydroxyapatite. They are disturbingly prevalent and costly, potentially afflicting over 50% of the population with multiple burdens including dental pain, disfigurement and increased caries risk. The two most prevalent DDD are dental fluorosis (characterised by diffuse opacities) and Molar/Incisor Hypomineralisation (MIH; characterised by demarcated opacities); both are caused by environmental agents (i.e. acquired defects). Another serious but rare DDD that can result in porous hydroxyapatite is the genetic disease amelogenesis imperfecta.

MIH typically affects 10-20% of children and is a major risk factor for caries, a risk factor for orthodontics, and is costly to society. MIH is thought to result from a multifactorial systemic disturbance of the enamel-forming cells. However, other than being dissociated from fluoride and linked to illness during infancy, the cause of MIH remains a mystery.

There are currently no products available that are designed to diagnose and repair MIH or other DDD. Differential diagnosis of caries and various DDD can be difficult and is largely dependent upon the experience and skill of individual dental health professionals. Current procedures and/or products developed for remineralisation of caries do not work well on MIH. Restorative treatment is frequently compromised because MIH enamel is soft, porous and poorly delineated from normal tooth tissue.

Accordingly, a need exists for new tools to diagnose, delineate and repair porous dental hydroxyapatite caused by caries and DDD. Here we address this need by detailing new technologies based on our recent discoveries of pathogenic mechanisms in conditions involving porous hydroxyapatite.

SUMMARY

A first aspect provides a kit, when used for detecting porous dental hydroxyapatite, comprising: a protein capable of binding porous dental hydroxyapatite; or a detector that detects said protein bound to porous dental hydroxyapatite.

A second aspect provides a probe, when used for detecting porous dental hydroxyapatite, comprising: a protein capable of binding to porous dental hydroxyapatite; and a reporter.

A third aspect provides a method for producing the probe of the second aspect comprising linking (i) a protein capable of binding to porous dental hydroxyapatite and (ii) a reporter.

A fourth aspect provides a method for detecting a condition involving porous dental hydroxyapatite comprising detecting in or on a tooth or a sample of the tooth of a subject a protein bound to porous dental hydroxyapatite.

A fifth aspect provides a method for detecting a hypomineralisation DDD comprising detecting a protein whose concentration bound to test hydroxyapatite of a tooth or of a sample of the tooth is increased relative to its concentration bound to control hydroxyapatite of a control tooth or of a control sample of a tooth, and detecting amelogenin whose concentration bound to the test hydroxyapatite is near that bound to the control hydroxyapatite.

A sixth aspect provides a method for detecting intact and/or broken MIH enamel comprising detecting albumin and hemoglobin bound to MIH hydroxyapatite, wherein detection of albumin but not hemoglobin is indicative of intact MIH enamel, and wherein detection of hemoglobin is indicative of broken MIH enamel.

A seventh aspect provides a kit for removing a protein bound to porous dental hydroxyapatite comprising: (a)(i) one or more washing solutions or (ii) dry components to prepare one or more washing solutions upon admixture with water, wherein the one or more washing solutions are adapted to remove a protein bound to porous dental hydroxyapatite; and (b) a remineralisation agent or remedial mineralisation agent.

An eighth aspect provides a method for removing a protein bound to porous dental hydroxyapatite comprising washing a tooth or a sample of the tooth with one or more washing solutions.

A ninth aspect provides a kit for removing a protein bound to porous dental hydroxyapatite comprising: one or more washing solutions; or one or more dry components to prepare one or more washing solutions upon admixture with water, wherein the one or more washing solutions are adapted to remove a protein in or on a tooth or a sample of the tooth detected as having porous dental hydroxyapatite by the method of the fourth aspect.

The kit, probe or methods of the first to sixth aspects allow detection in situ or diagnosis ex situ.

The kit, probe or methods of the first to sixth aspects are useful in detecting dental caries and/or MIH/DDD and delineating carious and/or MIH/DDD boundaries in preparation for restoration of a tooth. The clinician may then specifically remove the carious or MIH tissue thus revealed, ensuring clean border preparation and improving the likelihood of restoration success.

The kit of the first aspect or the probe of the second aspect provides key tools and the method of the fourth aspect allows for routine screening for porous dental hydroxyapatite. Moreover, the kit, probe or methods of the first to sixth aspects may be used for early detection of exposed dental hydroxyapatite. In this manner, the kit, probe or methods of the first to sixth aspects may be used for routine screening of dental changes that, without detection, may ultimately lead to dental caries (a precursor to caries), enabling accurate and timely targeting of restoration and/or remineralisation to prevent caries progression and/or promote remineralisation. In some embodiments, the kit, probe or methods of the first to sixth aspects are particularly suited to routine screening of children after eruption of the first permanent molar. It follows that the kit, probe or methods of the first to sixth aspects are also suited to routine screening of teeth for early detection of porous hydroxyapatite. Routine regular screening provides an excellent opportunity to detect at the earliest practical moment dental changes that may lead to dental caries.

Furthermore, the kit, probes and methods of the first to sixth aspects also allow monitoring of any treatment, such as known remineralisation therapies including fluoride or amorphous calcium phosphate that may be stabilised with bioactive molecules, which may be undertaken.

The method of the eighth aspect and the kits of the seventh and ninth aspects enable gentle and/or specific removal of excess proteins that are strongly retained on porous hydroxyapatite, for example in MIH lesions, to be used prior to or during remineralisation treatments.

The protein of any one of the first to fifth or seventh to ninth aspects may be selected from the group: Serum albumin; Complement C3 beta chain; Alpha-1-antitrypsin; Protein S100-A9; Lactotransferrin; Leukocyte elastase inhibitor; Antithrombin-III; Hemoglobin subunit alpha; Hemoglobin subunit beta; Hemoglobin subunit delta; Prolactin-inducible protein; Alpha amylase 1; Ig kappa chain V-III region SIE; Ig alpha-2 chain C region; Uncharacterized protein c6orf58; and Serpin B3. Furthermore, the protein of any one of the first to fourth or seventh to ninth aspects may be Amelogenin.

The kits of the first, seventh and ninth aspects, or the probe of the second aspect, may be in alternative forms. One form designates either suitability for or restriction to a specific use and is indicated by the word "for". Another form is restricted to a specific use only and is indicated by the words "when used for".

The methods of the third to sixth or eighth aspects may be presented in alternative forms, for example in European form ("agent for use") or second medical use (Swiss) form ("use of an agent in the manufacture of a medicament").

BRIEF DESCRIPTION OF THE FIGURES

The patent or application file contains at least one drawing executed as a photograph and in color. Copies of this patent or patent application with photographs and color drawings will be provided by the Office upon request and payment of the necessary fee.

FIG. 6 provides an amino acid sequence for Human Serum albumin (SEQ ID NO: 1; SwissProt accession P02768).

FIG. 7 provides an amino acid sequence for Human Complement C3 (SEQ ID NO: 2; SwissProt accession P01024).

FIG. 8 provides an amino acid sequence for Human Alpha-1-antitrypsin (SEQ ID NO: 3; SwissProt accession P01009).

FIG. 9 provides an amino acid sequence for Human Protein S100-A9 (SEQ ID NO: 4; SwissProt accession P06702).

FIG. 10 provides an amino acid sequence for Human Lactotransferrin (SEQ ID NO: 5; SwissProt accession P02788)

FIG. 11 provides an amino acid sequence for Human Leukocyte elastase inhibitor (SEQ ID NO: 6; SwissProt accession P30740).

FIG. 12 provides an amino acid sequence for Human Antithrombin-III (SEQ ID NO: 7; SwissProt accession P01008).

FIG. 13 provides an amino acid sequence for Human Hemoglobin subunit alpha (SEQ ID NO: 8; SwissProt accession P69905).

FIG. 14 provides an amino acid sequence for Human Hemoglobin subunit beta (SEQ ID NO: 9; SwissProt accession P68871).

FIG. 15 provides an amino acid sequence for Human Hemoglobin subunit delta (SEQ ID NO: 10; SwissProt accession P02042).

FIG. 16 provides an amino acid sequence for (Human Prolactin-inducible protein SEQ ID NO: 11; SwissProt accession P12273).

FIG. 17 provides an amino acid sequence for Human Alpha-amylase 1 (SEQ ID NO: 12; SwissProt accession P04745).

FIG. 18 provides an amino acid sequence for Human Ig kappa chain V-III region SIE (SEQ ID NO: 13; SwissProt accession P01620).

FIG. 19 provides an amino acid sequence for Human Ig alpha-2 chain C region (SEQ ID NO: 14; SwissProt accession P01877).

FIG. 20 provides an amino acid sequence for Human Uncharacterized protein C6orf58 (SEQ ID NO: IS; SwissProt accession Q6P5S2).

FIG. 21 provides an amino acid sequence for Human Serpin B3 (SEQ ID NO: 16; SwissProt accession P29508).

FIG. 22 provides an amino acid sequence for Human Amelogenin, X isoform (SEQ ID NO: 17; SwissProt accession Q99217).

FIG. 23 provides an amino acid sequence for Human Amelogenin, Y isoform (SEQ ID NO: 18; SwissProt accession Q99218).

FIG. 24 provides an amino acid sequence for Mouse Amelogenin (SEQ ID NO: 19; SwissProt accession P63277) also corresponding to recombinant Mouse Amelogenin.

FIG. 25 provides an amino acid sequence for Bovine Hemoglobin subunit alpha (SEQ ID NO: 20; SwissProt accession P01966).

FIG. 26 provides an amino acid sequence for Bovine Hemoglobin subunit beta (SEQ ID NO: 21; SwissProt accession P02070).

FIG. 27 depicts the chemical reaction for production of a maleimide-activated coloured reporter through reaction of N-hydroxysuccinimide ester (SMCC) with amido black (primary amine). Maleimide-activated coloured reporter is sulfhydryl-reactive, ready for conjugation with cysteine-thiols of hemoglobin β subunits.

FIG. 28 depicts the chemical reaction for production of a probe, in this example a coloured reporter-conjugated protein, via reaction of a maleimide-activated coloured reporter according to FIG. 28 with cysteine thiol groups (SH) of hemoglobin β subunits. Each hemoglobin tetramer binds two coloured reporter molecules, and leaves two subunits unmodified, which is likely important for preserving hemoglobin's hydroxyapatite-binding function.

DETAILED DESCRIPTION

Figure 1:
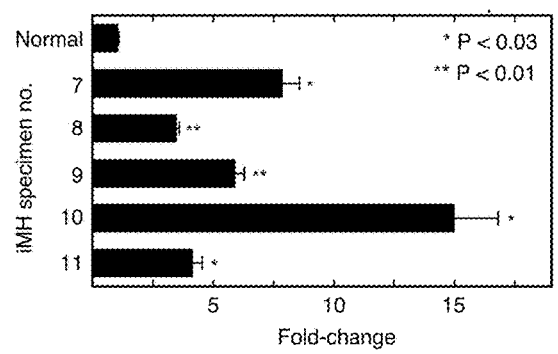
FIG. 1 plots the protein content of MIH enamel, which is abnormally high relative to normal enamel. Acid-insoluble proteins were extracted from normal enamel (normal) and a group of severe lesions exhibiting post-eruptive breakdown (specimens 7-11) then quantified by densitometric dot-blot analysis. Mean values (±SD) are shown for duplicate assays, each done at varied loads to ensure quantitative linearity ($r^2$>0.95). As indicated, all MIH specimens differed significantly from normal when compared pairwise using Student's t-test (homoscedastic, two-tailed). An albumin standard was used to derive absolute protein levels from these data.

Disclosed herein are kits, probes and methods for detecting a protein capable of binding to porous hydroxyapatite. The hydroxyapatite may be comprised in enamel or dentine. Moreover, whereas existing products stain dentine (but do not detect porous dental hydroxyapatite), for the first time disclosed herein is a product that detects defects in enamel, specifically by detecting porous dental hydroxyapatite.

The protein capable of binding to porous hydroxyapatite may be a human protein. For example, the protein may be selected from the group: Serum albumin (P02768); Complement C3 beta chain (P01024); Alpha-1-antitrypsin (P01009); Protein S100-A9 (P06702); Lactotransferrin (P02788); Leukocyte elastase inhibitor (P30740); Antithrombin-III (P01008); Hemoglobin subunit alpha (P69905); Hemoglobin subunit beta (P68871); Hemoglobin subunit delta (P02042); Prolactin-inducible protein (P12273); Alpha amylase 1 (P04745); Ig kappa chain V-III region SIE (P01620); Ig alpha-2 chain C region (P01877); Uncharacterized protein c6orf58 (Q6P5S2); Serpin B3 (P29508), where the term in parentheses indicates the unique SwissProt accession identifier (as listed in Table 1, SEQ ID NOs: 1 to 16 and FIGS. 6 to 21, respectively). In some embodiments, the protein may be an Amelogenin. The Amelogenin may be human. For example, amelogenin may be the X isoform of Human Amelogenin, (SEQ ID NO: 17, FIG. 22; SwissProt accession Q99217) or amelogenin may be the Y isoform of Human Amelogenin, (SEQ ID NO: 18, FIG. 23; SwissProt accession Q99218). Alternatively, the protein may be from a subject other than a human, for example, an animal such as a primate, a horse, cow, sheep, goat, dog or cat.

In some embodiments of the first to fourth and seventh to ninth aspects, the protein may be albumin, hemoglobin or a subunit thereof, or amelogenin.

In one embodiment of the fourth aspect, the method comprises detecting the protein which is other than amelogenin and detecting amelogenin, wherein presence of the protein and absence of amelogenin is indicative of MIH, and presence of amelogenin is indicative of hypomaturation defects including types of** amelogenesis imperfecta or dental fluorosis. The protein which is "other than amelogenin" is any one selected from: Serum albumin; Complement C3 beta chain; Alpha-1-antitrypsin; Protein S100-A9; Lactotransferrin; Leukocyte elastase inhibitor; Antithrombin-III; Hemoglobin subunit alpha; Hemoglobin subunit beta; Hemoglobin subunit delta; Prolactin-inducible protein; Alpha amylase 1; Ig kappa chain V-III region SIE; Ig alpha-2 chain C region; Uncharacterized protein c6orf58; and Serpin B3.

As used herein, "porous" or "porosity" refers to dental hydroxyapatite that is either hypomineralised or demineralised. Increased "porosity" is due to reduction in extent of mineral density, leading to increased space between mineral crystals.

"Hypomineralisation" as used herein, refers to incomplete development of dental enamel, resulting in decreased mineral density (increased enamel porosity) and mechanical strength. "Hypomineralisation" is caused by a genetic (e.g. amelogenesis imperfecta) or acquired (e.g. MIH, fluorosis) disruption of dental development. "Hypomineralisation" is distinct from "demineralisation", which occurs in caries for example. In caries, developmentally normal (or abnormal) enamel is subsequently demineralised. "Demineralisation" is distinct from "hypomineralisation", which refers to enamel that never achieved normal mineral content due to disrupted development.

As used herein, "remineralisation" refers to the return of minerals to the molecular structure of the tooth. The predominant mineral of teeth is hydroxyapatite. In some remineralisation processes, the hydroxyl group is substituted for a fluoro group to produce fluoroapatite, which is more acid-resistant than hydroxyapatite.

As used herein, "remedial mineralisation" refers to the use of remineralisation therapies on DDD (i.e. porous hydroxyapatite caused by incomplete mineralisation). Use of the term "remineralisation" is inappropriate in the DDD context because the porous hydroxyapatite was not caused by demineralisation.

As used herein, "caries" or "tooth decay" refers to reduction or loss of tooth enamel and dentine due to acid, particularly acid produced by infecting bacteria. "Caries" is defined by the process of demineralisation, and may be corrected using remineralisation methods if caught early.

As used herein, a "condition involving porous dental hydroxyapatite" includes dental caries, Molar/Incisor Hypomineralisation (MIH), amelogenesis imperfecta, dental fluorosis and other DDD manifesting as hypomineralised enamel (i.e. diffuse or demarcated opacities).

As used herein, "Molar/Incisor Hypomineralisation" or "MIH" refers to a DDD that results in incompletely hardened (hypomineralised) enamel, usually on the occlusal or incisal third of first permanent molars and incisors, respectively.

MIH and fluorosis are both characterised by subsurface porosity, whereas active caries can have a porous surface (inactive caries can form a sealed surface due to remineralisation).

As used herein, "exposed" enamel refers to sub-surface tissue that has been revealed due to loss of its protective surface layer. "Exposed" enamel may be normal or porous; there are many instances of surface breakdown on teeth that are not affected by MIH, or any other condition for that matter (e.g. otherwise normal teeth can fracture upon biting a hard object).

As used herein, "binds", "binding" or "bound" refers to a chemical interaction between a protein and hydroxyapatite that arrests the protein in relation to the hydroxyapatite. The interaction may be ionic, covalent, non-covalent, polar or non-polar.

As used herein, the term "detector" refers to any chemical, biochemical or biological substance that interacts specifically with a protein disclosed herein and generates an effect in response to the interaction. For example, the response may be visualisation of a coloured reporter, and thus visualisation of the protein. A "detector" may comprise a "reporter" or an antibody.

The term "detect" or "detecting" refers to identifying the response from the detector.

In one embodiment of the kit of the first aspect, the detector comprises a coloured reporter. In the probe of the second aspect, the detector is a reporter. In one embodiment of the probe, the reporter comprises a coloured reporter. When the detector comprises a coloured reporter, detecting the coloured reporter would involve visualising the coloured reporter and therefore the protein of interest. Alternatively, a reporter may be radio-opaque.

As used herein, the term "probe" refers to an agent such as a protein disclosed herein that can infiltrate porous enamel and that can specifically and tightly bind to hydroxyapatite and upon binding enable such binding to be detected. In other words, the probe comprises a specific "hydroxyapatite-targeting" molecule. A "probe" comprises a protein as disclosed herein and a reporter. According to this disclosure, a "probe" may not be an antibody.

Similarly, the term "specific" or "specifically" refers to binding where one substance binds to a particular second substance without substantially binding to any other substance. Such binding is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. As used herein, "specific" or "specifically" binding may refer to (i) the protein binding specifically to hydroxyapatite, (ii) the detector specifically binding to the protein, or (iii) the reporter specifically binding to the detector or protein.

In particular, specific binding refers to a substance having a $K_d$ at least 2-fold less than that of a non-specific target, for example, a substance having a $K_d$ at least 4-fold, 6-fold, 8-fold, 10-fold, or more than 10-fold less than that of a non-specific target. Alternatively, specific binding can be expressed as a molecule having a $K_d$ for the target of at most about $10^{-4}$ M, for example, about $10^{-5}$ M, about $10^{-6}$ M, about $10^{-7}$ M, about $10^{-8}$ M, about $10^{-9}$ M, about $10^{-10}$ M, about $10^{-11}$ M, about $10^{-12}$ M, or less.

In one embodiment of the kit of the first aspect, the detector comprises a reporter.

When used in situ, the detector or probe is non-toxic to the subject.

As used herein, a "reporter" refers to any chemical, biochemical or biological substance that generates a detectable effect. The "reporter" may specifically bind to or be linked to the detector or protein. The reporter may comprise biotin or streptavidin for use in a high affinity, non-covalent biotin-streptavidin bond. The reporter may exploit another high affinity, non-covalent bond.

In one embodiment of the kit of the first aspect or the probe of the second aspect, the reporter may be a coloured reporter. In other embodiments of the first or second aspect, the reporter may be a pigment, or a luminescent (including fluorescent or phosphorescent), radioactive, chemiluminescent substance, enzyme, or x-ray contrast molecule. A reporter comprising an X-ray contrast molecule (e.g. 5-amino-2,4,6-triiodoisophthalic acid; $^3$I) may be of use for sensitively detecting early-stage interproximal caries (a major challenge for current methods) using existing clinical radiographic equipment.

As used herein, the term "coloured reporter" refers to any coloured substance that absorbs some wavelengths of visible light preferentially.

Thus, when the reporter is a coloured reporter, the detectable effect is visualisation of a colour.

The coloured reporter may be any coloured substance that is amenable to linking, coupling or conjugating to the protein, whilst maintaining its characteristic as a coloured reporter. In one embodiment of the kit of the first aspect or probe of the second aspect, the coloured reporter is amido black. In one example, the probe comprises the protein (i.e. a hydroxyapatite-binding-protein) linked or coupled to a coloured reporter. Any protein from Table 1 may be linked or coupled to a coloured reporter and function to target the coloured reporter to porous hydroxyapatite. In one example, the protein is hemoglobin. Thus, in one example, the probe comprises hemoglobin linked to amido black.

A probe comprising a protein as disclosed herein, e.g. haemoglobin, is adsorbed cumulatively to porous dental hydroxyapatite. The probe will competitively bind to hydroxyapatite in the presence of other proteins because it is able to displace any species possessing lower affinity for hydroxyapatite. Such a probe may comprise amido black or $^3$I.

The coloured reporter may be selected, based on desired features that would be known to a person skilled in the art, from the group: Acetyl yellow (Fast yellow); Acid black 1 (Amido black 10B); Acid blue 22 (Water blue 1); Acid blue 93 (Methyl blue); Acid fuchsin (Acid fuchsin); Acid green (Light green SF yellowish); Acid green 1 (Naphthol green B); Acid green 5 (Light green SF yellowish); Acid magenta (Acid fuchsin); Acid orange 10 (Orange G); Acid red 4 (Azo-eosin); Acid red 26 (Xylidine ponceau); Acid red 29 (Chromotrope 2R); Acid red 44 (Ponceau 6R); Acid red 51 (Erythrosin B); Acid red 52 (Lissamine rhodamine B); Acid red 66 (Biebrich scarlet); Acid red 73 (Woodstain scarlet); Acid red 87 (Eosin Y ws); Acid red 91 (Eosin B); Acid red 92 (Phloxine B); Acid red 94 (Rose bengal); Acid red 101 (Azocarmine G); Acid red 103 (Azocarmine B); Acid roseine (Acid fuchsin); Acid rubin (Acid fuchsin); Acid violet 19 (Acid fuchsin); Acid yellow 1 (Naphthol yellow S); Acid yellow 7 (Lissamine flavine FF); Acid yellow 9 (Fast yellow); Acid yellow 23 (Tartrazine); Acid yellow 24 (Martius yellow); Acid yellow 36 (Metanil yellow); Acid yellow 73 (Fluorescein); Acid yellow 85 (Coomassie fast yellow G); Acid yellow S (Naphthol yellow S); Acid yellow T (Tartrazine); Acridine orange (Acridine orange); Acridine red (Acridine red); Acriflavine (Acriflavine); Alcian blue (Alcian blue 8GX); Alcian yellow (Alcian yellow); Alcohol soluble eosin (Ethyl eosin); Alizarin (Alizarin); Alizarin blue (Alizarin blue); Alizarin blue 2RC (Anthracene blue SWR); Alizarin carmine (Alizarin red S); Alizarin cyanin BBS (Alizarin cyanin BBS); Alizarol cyanin R (Chromoxane cyanin R); Alizarin red S (Alizarin red S); Alizarin purpurin (Purpurin); Alkali blue 4B, 5B (Alkali blue 5B); Aluminon (Chrome violet CG); Amido black 10B (Amido black 10B); Amidonaphthol red (Azophloxine); Amidoschwarz (Amido black 10B); Aniline blue WS (Aniline blue WS); Aniline purple (Mauveine); Anthracene blue SWR (Anthracene blue SWR); Anthracene blue SWX (Alizarin cyanin BBS); Auramine O (Auramine O); Azo-eosin (Azo-eosin); Azocarmine B (Azocarmine B); Azocarmine G (Azocarmine B); Azoeosin G (Azo-eosin); Azoic diazo 5 (Fast red B); Azoic diazo 48 (Fast blue B); Azophloxine (Azophloxine); Azovan blue (Evans blue); Azure A (Azure A); Azure B (Azure B); Azure C (Azure C); Basic blue 8 (Victoria blue 4R); Basic blue 9 (Methylene blue); Basic blue 12 (Nile blue A); Basic blue 15 (Night blue); Basic blue 17 (Toluidine blue O); Basic blue 20 (Methyl green); Basic blue 26 (Victoria blue B); Basic brown 1 (Bismarck brown Y); Basic fuchsin (Basic fuchsin); Basic green 4 (Malachite green); Basic green 5 (Methylene green); Basic orange 14 (Acridine orange); Basic red 2 (Safranin O); Basic red 5 (Neutral red); Basic red 9 (Pararosanilin); Basic violet 2 (New fuchsin); Basic violet 3 (Crystal violet); Basic violet 4 (Ethyl violet); Basic violet 10 (Rhodamine B); Basic violet 14 (Rosanilin); Basic yellow 1 (Thioflavine T); Basic yellow 2 (Auramine O); Biebrich scarlet (Biebrich scarlet); Biebrich scarlet R (Sudan IV); Bismarck brown Y (Bismarck brown Y); Blauschwarz (Naphalene blue black CS); Brazilein (Brazilein); Brazilin (Brazilin); Brilliant crocein (Woodstain scarlet); Brilliant crystal scarlet 6R (Ponceau 6R); Brilliant green (Brilliant green); Calcium red (Nuclear fast red); Carmine (Carmine); Carminic acid (Carmine); Carmoisine 6R (Chromotrope 2R); Celestine blue B (Celestine blue B); China blue (Aniline blue); Chlorantine fast red 5B (Sirius red 4B); Chicago blue 4B (Pontamine sky blue 5B); Chrome fast yellow 8GL (Chrome fast yellow 8GL); Chrome luxine yellow 8G (Chrome fast yellow 8GL); Chrome violet CG (Chrome violet CG); Chromotrope 2R (Chromotrope 2R); Chromoxane cyanin R (Chromoxane cyanin R); Cochineal (Carmine); Coelestine blue (Celestine blue B); Congo corinth (Congo corinth); Congo red (Congo red); Coomassie fast yellow G (Coomassie fast yellow G); Cotton blue (Methyl blue); Cotton red (Congo red); Croceine scarlet (Biebrich scarlet); Crocein scarlet 3B (Woodstain scarlet); Crocein scarlet MOO (Woodstain scarlet); Crocin (Saffron); Crystal ponceau 6R (Ponceau 6R); Crystal scarlet (Ponceau 6R); Crystal violet (Crystal violet); Dahlia (Hoffman's violet); Diamond green B (Malachite green); Direct blue 14 (Trypan blue); Direct blue 58 (Evans blue); Direct red (Congo red); Direct red 10 (Congo corinth); Direct red 28 (Congo red); Direct red 80 (Sirius red F3B); Direct red 81 (Sirius red 4B); Direct yellow 7 (Thioflavine S); Direct yellow 11 (Sun yellow); Durazol blue 4R (Durazol blue 4R); Durazol blue 8G (Durazol blue 8G); Eosin B (Eosin B); Eosin Bluish (Eosin B); Eosin (Eosin Y ws); Eosin Y (Eosin Y ws); Eosin yellowish (Eosin Y ws); Eosinol (Eosinol); Erie garnet B (Congo corinth); Eriochrome cyanin R (Chromoxane cyanin R); Erythrosin B (Erythrosin B); Ethyl eosin (Ethyl eosin); Ethyl green (Ethyl green); Ethyl violet (Ethyl violet); Evans blue (Evans blue); Fast blue B (Fast blue B); Fast green FCF (Fast green FCF); Fast red B (Fast red B); Fast yellow (Fast yellow); Fast yellow extra (Fast yellow); Fast yellow G (Fast yellow); Fat black HB (Sudan black B); Fluorescein (Fluorescein); Food green 3 (Fast green FCF); Gallein (Gallein); Gallamine blue (Gallamine blue); Gallocyanin (Gallocyanin); Gentian violet (Methyl violet 2B); Guinee green (Guinee green B); Haematein (Hematein); Haematine (Hematein); Haematoxylin (Hematoxylin); Helio fast rubin BBL (Nuclear fast red); Helvetia blue (Methyl blue); Hematein (Hematein); Hematine (Hematein); Hematoxylin (Hematoxylin); Hoffman's violet (Hoffman's violet); Hydrazine yellow (Tartrazine); Indigo carmine (Indigo carmine); Imperial red (Eosin B); Ingrain blue 1 (Alcian blue 8GX); Ingrain yellow 1 (Alcian yellow); INT (Iodonitrotetrazolium); Iodine green (Iodine green); Kermes (Kermes); Kermesic acid (Kermes); Kernechtrot (Nuclear fast red); Kiton rhodamine B (Lissamine rhodamine B); Lac (Laccaic acid); Laccaic acid (Laccaic acid); Lauth's violet (Thionin); Light green (Light green SF yellowish); Lissamine fast yellow (Lissamine fast yellow); Lissamine flavine FF (Lissamine flavine FF); Lissamine green SF (Light green SF yellowish); Lissamine rhodamine B (Lissamine rhodamine B); Luxine pure yellow 6G (Chrome fast yellow 8GL); Luxol fast blue (Luxol fast blue MBS); Magenta 0 (Pararosanilin); Magenta I (Rosanilin); Magenta II (Magenta II); Magenta III (New fuchsin); Malachite green (Malachite green); Manchester brown (Bismarck brown Y); Martius yellow (Martius yellow); Mauve (Mauveine); Mauveine (Mauveine); Merbromin (Mercurochrome 220); Mercurochrome (Mercurochrome 220); Metanil yellow (Metanil yellow); Methyl blue (Methyl blue); Methyl green (Methyl green); Methyl violet (Methyl violet 2B); Methyl violet 2B (Methyl violet 2B); Methyl violet 10B (Crystal violet); Methylene azure A (Azure A); Methylene azure B (Azure B); Methylene azure C (Azure C); Methylene blue (Methylene blue); Methylene green (Methylene green); Milling yellow 3G (Milling yellow 3G); Mordant blue 3 (Chromoxane cyanin R); Mordant blue 10 (Gallocyanin); Mordant blue 14 (Celestine blue B); Mordant blue 23 (Alizarin cyanin BBS); Mordant blue 32 (Anthracene blue SWR); Mordant blue 45 (Gallamine blue); Mordant red 3 (Alizarin red S); Mordant red 11 (Alizarin); Mordant violet 25 (Gallein); Mordant violet 39 (Chrome violet CG); Mordant yellow 33 (Chrome fast yellow 8GL); Naphthalene blue black (Naphalene blue black CS); Naphthol blue black (Amido black 10B); Naphthol green B (Naphthol green B); Naphthol yellow S (Naphthol yellow S); Natural black 1 (Hematein); Natural red (Purpurin); Natural red 3 (Kermes); Natural red 4 (Carmine); Natural red 8 (Purpurin); Natural red 16 (Purpurin); Natural red 24 (Brazilin); Natural red 25 (Laccaic acid); Natural red 28 (Orcein); Natural yellow 6 (Saffron); NBT (Nitro blue tetrazolium); Neutral red (Neutral red); New fuchsin (New fuchsin); Niagara blue 3B (Trypan blue); Night blue (Night blue); Nile blue (Nile blue A); Nile blue A (Nile blue A); Nile blue sulphate (Nile blue A); Nile red (Nile red); Nitro BT (Nitro blue tetrazolium); Nitro blue tetrazolium (Nitro blue tetrazolium); Nuclear fast red (Nuclear fast red); Oil red O (Oil red O); Orange G (Orange G); Orcein (Orcein); Pararosanilin (Pararosanilin); Perkin's violet (Mauveine); Phloxine B (Phloxine B); Picric acid (Picric acid); Ponceau 2R (Xylidine ponceau); Ponceau 6R (Ponceau 6R); Ponceau B (Biebrich scarlet); Ponceau de Xylidine (Xylidine ponceau); Ponceau S (Ponceau S); Pontamine sky blue 5B (Pontamine sky blue 5B); Primula (Hoffman's violet); Primuline (Primuline); Purpurin (Purpurin); Pyronin B (Pyronin B); Pyronin G (Pyronin Y); Pyronin Y (Pyronin Y); Rhodamine B (Rhodamine B); Rosanilin (Rosanilin); Rose bengal (Rose bengal); Saffron (Saffron); Safranin O (Safranin O); Scarlet R (Sudan IV); Scarlet red (Sudan IV); Scharlach R (Sudan IV); Shellac (Laccaic acid); Sirius red F3B (Sirius red F3B); Sirius red 4B (Sirius red 4B); Sirius supra blue F3R (Durazol blue 4R); Solochrome cyanin R (Chromoxane cyanin R); Soluble blue (Aniline blue); Solvent black 3 (Sudan black B); Solvent blue 38 (Luxol fast blue MBS); Solvent red 23 (Sudan III); Solvent red 24 (Sudan IV); Solvent red 27 (Oil red O); Solvent red 45 (Ethyl eosin); Solvent yellow 94 (Fluorescein); Spirit soluble eosin (Ethyl eosin); Sudan III (Sudan III); Sudan IV (Sudan IV); Sudan black B (Sudan black B); Sudan red BK (Sudan III); Sulfur yellow S (Naphthol yellow S); Sulpho rhodamine B (Lissamine rhodamine B); Sun yellow (Sun yellow); Swiss blue (Methylene blue); Tartrazine (Tartrazine); Thioflavine S (Thioflavine S); Thioflavine T (Thioflavine T); Thionin (Thionin); Toluidine blue (Toluidine blue O); Toluyline red (Neutral red); Tropaeolin G (Metanil yellow); Trypaflavine (Acriflavine); Trypan blue (Trypan blue); Uranin (Fluorescein); Victoria blue 4R (Victoria blue 4R); Victoria blue B (Victoria blue B); Victoria blue R (Victoria blue R); Victoria green B (Malachite green); Water blue 1 (Water blue 1); Water soluble eosin (Eosin Y ws); Woodstain scarlet (Woodstain scarlet); Xylene red B (Lissamine rhodamine B); Xylidine ponceau (Xylidine ponceau); and Yellowish eosin (Eosin Y ws). The desired features to be considered by the skilled addressee include compatibility with a protein and/or a linker to be used according to this disclosure, non-toxicity, and maintenance of protein binding to porous dental hydroxyapatite, for example.

In alternative embodiments of the first to fifth or seventh to ninth aspects, the protein is not listed in the examples of Table 1, but is known to the skilled addressee to bind to hydroxyapatite, for example osteocalcin or decorin. Use of the leucine-rich repeat domains 4-5 from decorin may provide a specific targeting mechanism for porous hydroxyapatite in dentine.

Alternatively, in embodiments of the first to fifth or seventh to ninth aspects, the protein may be a peptide or protein fragment, provided that the peptide or protein fragment retains its ability to bind to porous dental hydroxyapatite.

Alternatively, the skilled addressee will be aware of small molecules (or polymers thereof), for example tetracycline or amino bisphosphonate, that can bind to hydroxyapatite, which may be of more use in terms of ability to penetrate micro-porous regions, and in terms of stability (e.g. product shelf-life). Amino-bisphosphonate may produce a compound with qualities suited to detecting and delineating caries (small, high-affinity probe for penetrating porous enamel surface and strongly binding to demineralised enamel).

In some embodiments of the kit of the first aspect or probe of the second aspect, the detector or probe further comprises a linker linking the reporter and the detector or protein. The linker may be a heterobifunctional cross-linker. For example, the heterobifunctional linker may be succinimidyl 4-[N-maleimidomethyl]cyclohexanecarboxylic acid N-hydroxysuccinimide ester (SMCC). Other examples of linking agents that may be used in accordance with this disclosure include succinimidyl-6-[β-maleimidopropionamido] hexanoate (SMPH), N-hydroxysuccinimidyl-4-azidosalicylic acid (NHS-ASA), and N,N-dicyclohexylcarbodiimide (DCC).

Other types of molecules may be used as a linker. For example, high affinity, non-covalent bonds such as biotin-streptavidin are also contemplated herein.

The skilled addressee will be aware of many cross-linking agents that are available with various reactive chemistries and spacer-arm lengths, further increasing the flexibility of this approach.

In one embodiment of the kit of the first aspect or probe of the second aspect, the reporter and the protein may be provided already linked. Alternatively, the reporter and protein may be provided separately for subsequent linkage. The kit or probe may comprise a linker. The protein, reporter and linker of the kit or probe may be presented in any possible combination. For example, when the reporter and protein are linked via a linker, the probe may be "ready-to-use", i.e. the three components may be linked. Alternatively, the protein and the linker may be linked and provided separately to the reporter. Alternatively, the linker and the reporter may be linked and provided separately to the protein. Alternatively, the protein, the reporter, and the linker may be provided as separate components. In one embodiment of the first aspect, the kit will comprise the reporter and the linker, but not the protein.

In some embodiments of the kit of the first aspect, the detector comprises an antibody that specifically binds the protein. In another embodiment, the detector may comprise biotin or streptavidin for use in a high affinity, non-covalent biotin-streptavidin bond. The detector may exploit another high affinity, non-covalent bond. For example, the detector may comprise an antibody alternative, such as a peptide-based protein ligand. A peptide-based protein ligand known in the art is a synbody.

The term "antibody" is used in the broadest sense and specifically covers, for example, polyclonal antibodies, monoclonal antibodies (including antagonist and neutralizing antibodies), antibody compositions with polyepitopic specificity, single chain antibodies, and fragments of antibodies, provided that they exhibit the desired biological or immunological activity. The antibody may be a conjugated antibody or any other type of antibody known to the person skilled in the art.

The antibody may be detected by any method known to the person skilled in the art. The primary antibody may comprise a reporter. Alternatively, a secondary antibody targeting the primary antibody may comprise a reporter.

The antibody may be any antibody known by the skilled addressee to specifically bind to a protein selected from the group: Serum albumin; Complement C3 beta chain; Alpha-1-antitrypsin; Protein S100-A9; Lactotransferrin; Leukocyte elastase inhibitor; Antithrombin-III; Hemoglobin subunit alpha; Hemoglobin subunit beta; Hemoglobin subunit delta; Prolactin-inducible protein; Alpha amylase 1; Ig kappa chain V-III region SIE; Ig alpha-2 chain C region; Uncharacterized protein c6orf58; and Serpin B3. In one embodiment, the antibody may specifically bind to an amelogenin.

In one embodiment of the kit of the first aspect, an anti-serum albumin monoclonal antibody may be selected from the group: AL-01; 1.6.731; 1A9; 6B11; OCH1E5; 1C8; 1G2; 2B2; 2B3; 2B6; 14E7; 15C7; Alb1; and a mouse monoclonal IgG$_1$ antibody with product code sc-70340 (Santa Cruz Biotechnology Inc). In one embodiment, an anti Complement C3 beta chain monoclonal antibody may be clone 755. In another embodiment, an anti-human C3 monoclonal antibody that cross-reacts with Complement C3 beta chain may be used and may be clone 11H9. In one embodiment, an anti-Alpha-1-antitrypsin monoclonal antibody may be selected from the group: 5B12; 703; 704; 8A0; B9; and G11. In one embodiment, an anti-Protein S100-A9 monoclonal antibody may be selected from the group: 0.N.390A; 47-8D3; NO. 134; NO. 19; and S32.2. In one embodiment, an anti-Lactotransferrin monoclonal antibody may be selected from the group: 1C6; 2B8; B97; CLB-13.17; and 1A1. In one embodiment, an anti-Antithrombin-III monoclonal antibody may be 4B3 or BD1205. In one embodiment, an anti-Hemoglobin subunit alpha antibody may be a goat polyclonal IgG antibody with product code sc-70340 (Santa Cruz Biotechnology Inc). In one embodiment, an anti-Hemoglobin subunit beta antibody may be a mouse monoclonal $IgG_1$ antibody with product code sc-21757 (Santa Cruz Biotechnology Inc). In one embodiment, an anti-Ig alpha-2 chain C region monoclonal antibody may be clone 14AS (also referred to as anti-human IgA2). In one embodiment, an anti-Amelogenin X antibody may be a rabbit polyclonal IgG antibody with product code sc-32892 (Santa Cruz Biotechnology Inc). The skilled addressee will appreciate that other suitable antibodies are available.

In one embodiment of the kit, probe or method of the first, second or fourth aspects, a first protein is selected from the group: Serum albumin; Complement C3 beta chain; Alpha-1-antitrypsin; Protein S100-A9; Lactotransferrin; Leukocyte elastase inhibitor; Antithrombin-III; Hemoglobin subunit alpha; Hemoglobin subunit beta; Hemoglobin subunit delta; Prolactin-inducible protein; Alpha amylase 1; Ig kappa chain V-III region SIE; Ig alpha-2 chain C region; Uncharacterized protein c6orf58; and Serpin B3 may be detected, and a second protein may be detected, wherein the second protein is amelogenin. It follows that a kit of the first aspect may also comprise a second detector that detects amelogenin. The second detector may be an anti-amelogenin antibody.

Alternatively, detecting may comprise immunodetection, chromatography, electrophoresis, mass spectrometry, or microscopy. Immunodetection may comprise enzyme-linked immunosorbent assay (ELISA), Western Blot, dot blot, slot blot, or flow cytometry, for example. Microscopy may comprise confocal laser, fluorescence or electron microscopy, for example.

The detector or probe may be applied in different ways, for example in a liquid, gel, capsule, tablet, aqueous solution, aqueous or oily suspension, lozenge, troche, powder, granule, emulsion, syrup or elixir.

In one embodiment of the kit of the first aspect or probe of the second aspect, the detector or probe comprises a solvent in which the detector or probe is dissolved, suspended or emulsified. The solvent may be one that is used generally in medicine or industry or similar. Examples include water, ethanol, n-propanol, 2-butyl alcohol, isobutyl alcohol, n-amyl alcohol, isoamyl alcohol, ethylene glycol, 2-methoxyethanol, diethylene glycol, triethylene glycol, tetraethylene glycol, polyethylene glycol, propylene glycol, dipropylene glycol, polypropylene glycol, trimethylene glycol, 1,2-butanediol, 1,3-butanediol, 2,3-butanediol, 1,4-butanediol, 1,5-pentanediol, ethylene glycol monomethyl ether, ethylene glycol monomethyl ether acetate, ethylene glycol monoethyl ether, ethylene glycol diethylether, ethyleneglycolmonoethyletheracetate, ethylene glycol isopropyl ether, ethylene glycol monobutyl ether, ethylene glycol dibutyl ether, ethylene glycol monoacetate, ethylene glycol diacetate, diethylene glycol monomethyl ether, diethylene glycol monoethyl ether, diethylene glycol monoethyl ether acetate, diethylene glycol monobutyl ether, diethylene glycolmonobutyl ether acetate, diethylene glycol dimethyl ether, diethylene glycol methylethyl ether, diethylene glycol diethyl ether, diethylene glycol acetate, triethylene glycol monomethyl ether, triethylene glycol monoethyl ether, propylene glycol monomethyl ether, propylene glycol monoethyl ether, dipropylene glycol monomethyl ether, dipropylene glycol monoethyl ether, ee tripropylene glycol monomethyl ether, glycerin, tetrahydrofuran, dimethylformamide, dioxane, acetone, and dimethoxyethane.

In some embodiments, the solvent comprises water, ethanol, glycerin, isobutyl alcohol, ethylene glycol, diethylene glycol, triethylene glycol, acetone, or propylene glycol, which are compatible with humans.

One solvent may be used singly or two or more solvents may be used in admixture.

The detector may be compounded with a thickener to increase its viscosity to about 50 to about 2 000 mPa·s, for example 100, 200, 300, 400, 500, 750, 1000, 1250, 1500, or 1750 mPa·s (at 25° C.), thereby forming a gel. In gel form, applying the detector with a toothbrush enables simultaneous cleaning of the tooth and application of the detector.

Examples of thickeners that may be used include: synthetic additives such as sodium alginate, propylene glycol alginate, sodium carboxymethyl cellulose, calcium carboxymethyl cellulose, sodium carboxymethyl starch, sodium starch phosphate, sodium polyacrylate, methyl cellulose, hydroxypropyl cellulose, and polyvinylpyrrolidone; natural thickeners such as cyamoposis gum, Carob bean gum, Tara gum, Tamarind seed gum, gum arabic, tragacanth gum, Karaya gum, alginic acid, carrageenan, xanthan gum, gellan gum, curdlan, chitin, chitosan, and chitosamine; and inorganic thickeners such as calcium carbonate, calcium silicate, silica powder, amorphous hydrous silicate, and hydrophobic silica.

In order to obtain viscosity in the range of about 50 to about 2 000 mPa·s, the compounding amount of the thickener varies depending on the kind of the thickener. For example, when sodium carboxymethyl cellulose having a large thickening effect, the compounding amount may be about 0.5 to 4% by weight, and when methyl cellulose, the compounding amount may be about 10 to 30% by weight.

Furthermore, the detector or probe may comprise additives such as sweeteners, flavours, and preservatives. Suitable sweeteners include sucrose, lactose, glucose, aspartame or saccharin. Suitable flavouring agents include peppermint oil, oil of wintergreen, cherry, orange or raspberry flavouring. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable disintegrating agents include corn starch, methylcellulose, polyvinylpyrrolidone, xanthan gum, bentonite, alginic acid or agar. A tablet may contain the detector in admixture with non-toxic pharmaceutically acceptable excipients which are suitable for the manufacture of tablets.

In another embodiment, the kit of the first aspect further comprises one or more washing solutions.

The kit of the seventh or ninth aspect comprises one or more washing solutions.

A washing solution of the kit of the first, seventh or ninth aspect may comprise a solution to remove any protein not specifically bound to porous hydroxyapatite, i.e. non-desorbing. For example, a washing solution that does not desorb a protein bound to hydroxyapatite may be water, saline, Tris buffer, or mild detergent etc. As the oral cavity contains abundant proteins including many of the proteins that bind hydroxyapatite, a washing solution allows protein not specifically bound to hydroxyapatite to be removed from the tooth or sample thereof prior to application of the detector.

In other embodiments of the kit of the first, seventh or ninth aspect, the washing solution comprises magnesium ions ($Mg^{2+}$), dihydrogenphosphate ions ($H_2PO_4^-$), hydrogenphosphate ions ($HPO_4^{2-}$), or phosphate ions ($PO_4^{3-}$) (collectively "$PO_4$"), or may comprise a plurality of washing solutions that may each comprise magnesium ions ($Mg^{2+}$), dihydrogenphosphate ions ($H_2PO_4^-$), hydrogenphosphate ions ($HPO_4^{2-}$), or phosphate ions ($PO_4^{3-}$), administrable sequentially. Any soluble magnesium salt may be used and any soluble dihydrogenphosphate, hydrogenphosphate ions ($HPO_4^{2-}$), or phosphate salt may be used, provided that it is non-toxic if applied in situ. In one embodiment, the washing solution comprises magnesium chloride or sodium dihydrogenphosphate. The skilled addressee will appreciate that other washing solutions capable of desorbing protein from hydroxyapatite are available.

A washing solution may comprise hypochlorous acid (HOCl), hypochlorite (NaOCl) or calcium hypochlorite (Ca(OCl)$_2$) (collectively "bleach").

A washing solution may be provided ready to use. Alternatively, the washing solution may be provided as a concentrate to prepare the washing solution upon dilution with water. Alternatively, the washing solution may be provided as one or more dry components to prepare the washing solution upon admixture with water.

The washing solution may comprise less than 1 mM, about 1 mM, about 2 mM, about 3 mM, about 4 mM, about 5 mM, about 6 mM, about 7 mM, about 8 mM, about 9 mM, about 10 mM or more than 10 mM magnesium ions. The washing solution may comprise less than 0.1 M, about 0.1 M, about 0.5 M, about 0.6 M, about 0.7 M, about 0.8 M, about 0.9 M, about 1 M, about 1.1 M, about 1.2 M, about 1.3 M, about 1.4 M, about 1.5 M, about 2 M, about 10 M or more than 10 M magnesium ions. The washing solution may comprise less than 0.04 M, about 0.04 M, about 0.08 M, about 0.09 M, about 0.1 M, about 0.2 M, about 0.3 M, about 0.4 M, about 0.5 M, about 0.6 M, about 0.7 M, about 0.8 M, about 0.9 M, about 1 M, about 1.5 M, about 2 M, about 4 M, or more than 4 M dihydrogenphosphate, hydrogenphosphate or phosphate ions.

The washing solution may comprise about 10% bleach (about 0.4% $^-$OCl), neat or undiluted bleach (about 4% $^-$OCl), or may comprise about 20% (about 0.8% $^-$OCl), about 30% (about 1.2% $^-$OCl), about 40% (about 1.6% $^-$OCl), about 50% (about 2.0% $^-$OCl), about 60% (about 2.4% $^-$OCl), about 70% (about 2.8% $^-$OCl), about 80% (about 3.2% $^-$OCl), about 90% (about 3.6% $^-$OCl) or about 95% bleach (about 3.8% $^-$OCl).

While not wishing to be bound to any particular theory, it is thought that providing a plurality of washing solutions with a step-wise concentration gradient of magnesium and/or phosphate removes more proteins than a single concentration magnesium solution. It is thought that bleach ($^-$OCl) non-specifically strips bound proteins from hydroxyapatite.

Thus, in one embodiment of the kit of the first, seventh or ninth aspect, the one or more washing solutions, or plurality of washing solutions, may comprise a solution of about 5 mM magnesium chloride, a solution of about 1 M magnesium chloride, and/or a solution of about 0.4 M sodium dihydrogenphosphate.

Where one or more (a plurality) of washing solutions is applied, the washing solutions may be applied in any order. Alternatively, where one or more (a plurality) of washing solutions is applied, the washing solutions may be applied sequentially in the order of low magnesium concentration (e.g. 5 mM), high magnesium concentration (e.g. 1 M), dihydrogenphosphate (e.g. 0.4 M; or hydrogenphosphate or phosphate). Alternatively, a washing solution may comprise in combination magnesium and phosphate, for example, about 1 M magnesium concentration and about 0.4 M dihydrogenphosphate, hydrogenphosphate or phosphate.

Washing may occur before detecting, or after detecting, or before and after detecting.

As used herein, "removes" or "removing" refers to a reduction in the concentration of protein bound to hydroxyapatite.

As used herein, a "sample" is a portion or part of the tooth to be used for detection or diagnosis of porous hydroxyapatite. A "control sample" is a portion or part of the tooth known to be healthy and free of porous hydroxyapatite and is used for reference purposes when detecting or diagnosing porosity in test hydroxyapatite. A "sample" may be obtained by wiping, swabbing, scraping, chipping, drilling or similar. A sampler may be adapted for obtaining a sample by swabbing, wiping or any other method of collection known to the skilled addressee.

In one embodiment of the method of the fourth to sixth aspect, the tooth is first cleaned by brushing or other means. The tooth may be dried.

In one embodiment of the kit of the first aspect, probe of the second aspect, or method of the fourth to sixth aspect, the detector is applied using a brush, toothbrush, a cotton swab, a cotton ball or by dropping from a nozzle-equipped container.

As used herein, "applied", "applying" or "application" has its ordinary meaning of bringing into contact the detector or probe or washing solution and the tooth or sample thereof, or bringing into contact the reporter and the detector or protein.

After application of the detector or probe, the detector or probe is incubated on the tooth for a period of time sufficient for binding of the detector to the protein or for binding of the probe to the hydroxyapatite. The incubation period may be 1, 2, 3, 4, 5, 6, 7, 8, 9, 10, 15, 20, 25, 30, 35, 40, 45, 50, 55 or 60 s. Alternatively, the incubation time may be 1, 1.5, 2, 2.5, 3, 3.5, 4, 4.5, or 5 min. Alternatively, the incubation time may be more than 5 min, such as 10, 15 or 20 min. After incubation, excess detector or probe may be disgorged from the mouth with or without washing using water or a washing solution.

The method or use may be performed in or on the tooth in situ in a subject. Alternatively, the method or use may be performed in or on the tooth or a sample of the tooth after removal from a subject.

The subject includes a mammal. The mammal may be a human. The human may be any age. The human may be under about 12 years of age. The human may be about 2 to about 12 years of age, about 4 to about 10 years of age, or about 6 to about 10 years of age. Alternatively, the subject may be 12 to 20, 20 to 30, 30 to 40, 40 to 50, 50 to 60, 60 to 70, 70 to 80, 80 to 90, or 90 to 100 years of age.

The subject may develop porous hydroxyapatite after normal hydroxyapatite and normal enamel has developed, or the subject may have porous hydroxyapatite throughout development.

Alternatively, the subject may be a domestic, zoo, or companion animal. While it is particularly contemplated that the methods and uses herein are suitable for humans, they are also applicable to primates, companion animals such as dogs and cats, domestic animals such as horses, cattle, sheep and goats, zoo animals such as felids, canids, bovids, and ungulates, or laboratory animals such as lagomorphs and rodents. A subject may be afflicted with a dental disorder, or may not be afflicted with a dental disorder (i.e., free of detectable disease).

The diagnostic power of the kits or methods disclosed herein is based on conditions of porous hydroxyapatite (DDD and caries) having distinguishable protein profiles (e.g. MIH: abundant proteins from Table 1, little or no amelogenin; mature fluorosis: trace amounts of albumin and amelogenin; hypomaturation amelogenesis imperfecta: abundant amelogenin). Different defects may require different wash procedures before remedial mineralisation, or different restoration methods and materials (or influence the choice thereof). Protein concentration in test enamel of a tooth or sample thereof may be assessed by various means, and the condition involving porous hydroxyapatite can be diagnosed based on the identity of proteins with elevated abundance relative to control.

A further application of the present disclosure is to categorise the MIH lesion sub-type (e.g. as intact or broken), which may impact the type of treatment required (e.g. different protein compositions may need different wash procedures before remedial mineralisation).

As used herein, "intact" has its ordinary meaning of undisrupted, uninjured or unaltered and is used in relation to the surface of tooth enamel. "Intact" here refers to a lesion covered with a shell of harder enamel at the tooth surface, and is referred to as a subsurface lesion, indicating a stratified structure.

In contrast, "broken" here refers to an MIH lesion whose hard enamel shell either has become disrupted due to mechanical forces, or was not present initially (perhaps lost during tooth eruption, or not produced during development).

As used herein, "permeable surface" refers to intact or broken enamel that allows access of oral fluid or any other solution (and associated components including proteins) into subsurface regions. Conversely, an "impermeable surface" refers to intact or broken enamel that blocks such access.

MIH lesions comprising intact enamel, despite comprising porous hydroxyapatite, may or may not present porous dental hydroxyapatite amenable to detection (i.e. may have a permeable or impermeable surface). Therefore, in some embodiments of the first, seventh or ninth aspects, a kit may comprise a permeabilising agent, or a method of the fourth to sixth aspects (e.g. mechanical permeabilisation) may comprise permeabilising the tooth or a sample of the tooth. Such an agent or method will be used in pre-treating a lesion that has an impermeable surface. Alternatively, such an agent may be used to access a lesion previously subject to remineralisation or remedial mineralisation.

As used herein, "permeabilise" or "permeabilising" refers to opening pores in impermeable enamel of sufficient dimension to enable the detector and/or the washing solution access to the porous hydroxyapatite, and/or to enable protein removal.

The permeabilisation agent is a formulation capable of permeabilising the surface layer of enamel (e.g. it may comprise an acid or some other agent known by the skilled addressee to permeabilise enamel). The permeabilisation agent may be in the form of a solution or a gel, for example.

In some embodiments of the first, seventh or ninth aspect, a kit may comprise a remineralisation agent, or the method may comprise remineralising the tooth or sample thereof. A remineralisation agent may comprise fluoride, soluble calcium phosphate or amorphous calcium phosphate, which may be stabilised with bioactive molecules.

EXAMPLES

Example 1—the Protein Composition of MIH Enamel Depends on Surface Integrity

Materials and Methods
Specimens

Human and Sprague-Dawley rat specimens were obtained with appropriate ethical approvals, and stored at −80° C. MIH was diagnosed according to standard criteria (Weerheijm, 2003). After extraction, MIH teeth were water-rinsed to remove visible blood, then blotted dry and stored frozen immediately. Whole saliva, stimulated by chewing on wax, was clarified by centrifugation (20,000 g, 5 min) before storage. Serum and erythrocytes were prepared conventionally from blood of 6-day-old rats. Secretory enamel matrix was isolated from developing rat teeth as before (Hubbard, 1996) except using 5-day-old first molars.

Profiling of Enamel Proteins

Overt MIH lesions were collected from freshly thawed specimens by scraping with a scalpel, taking care to avoid carious enamel and dentine. Normal enamel was sampled using a slowly rotating dental bur (No. 6). Immediately afterwards, enamel samples (2-5 μl packed vol) were suspended in 10% trifluoroacetic acid (10 volumes, 10 min at room temperature with vortexing and bath sonication), then centrifuged (20,000 g, 4° C., 5 min) to sediment acid-insoluble protein. Pellets were solubilized in gel-loading buffer containing 2% SDS and 100 mmol/L dithiothreitol (Hubbard, 1996), with additional protease inhibitors (1 mmol/L phenylmethylsulfonyl fluoride, 1 mmol/L benzamidine, 5 μg/mL pepstatin, 5 μg/mL leupeptin) where indicated. SDS extracts were quantified by dot blotting with Amido Black and subjected to mini SDS-PAGE with Coomassie Blue staining or immunoblotting (Hubbard, 1995). Amelogenin antiserum was raised conventionally in rabbits, using recombinant mouse amelogenin (SEQ ID NO: 19) as immunogen.

Proteomics Analysis

Gel bands were subjected to trypsinolysis and tandem mass spectrometry as before (Mangum et al., 2006) except using an ion-trap instrument with chip-based nanospray (Chip-LC/MSD XCT, from Agilent Technologies, Santa Clara, Calif., USA). Proteins were identified using the MASCOT search engine and SwissProt human database with strict acceptance criteria (minimally two sequence tags (Mangum et al., 2006)).

Mineral-Binding Assays

Figure 4:
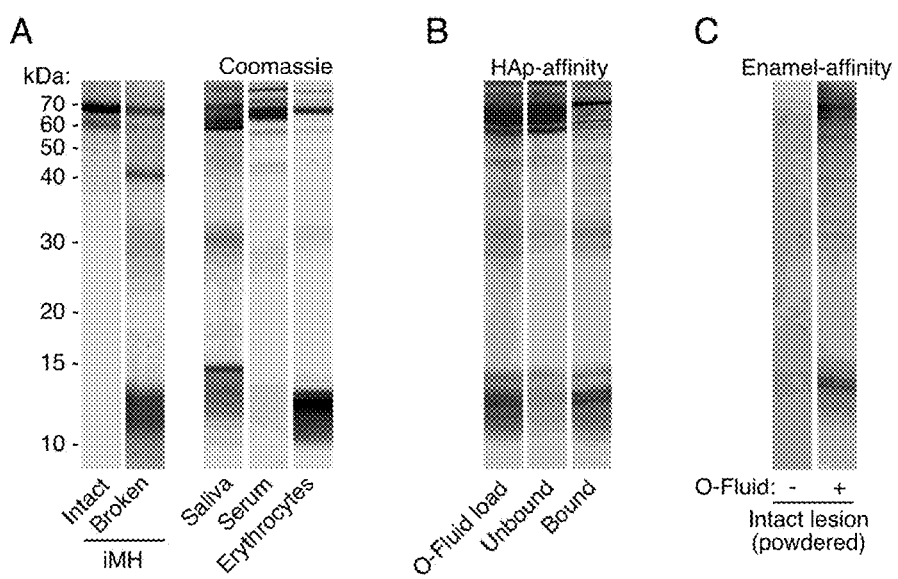
FIG. 4 depicts mineralisation assays revealing that surface integrity regulates the protein composition of MIH enamel. (A) Comparative profiling of MIH enamel and body fluids, showing similarities for intact lesions vs. serum and for broken lesions vs. saliva and erythrocytes. (B) Hydroxyapatite-binding (HAp-affinity) assay, showing that a subset of proteins from mock oral fluid (O-Fluid) were preferentially retained (cf. differences between the Load, Bound and Unbound fractions). Note a strong resemblance between the Bound profile and the broken lesion in panel A (specimen 7). (C) An equivalent mineral-binding assay to B, but with powdered MIH enamel in place of hydroxyapatite. The profiles show enamel from an intact lesion, before and after exposure to mock oral fluid (+/−O-Fluid). Note a resemblance of the protein-bound profile (+) to those of broken lesions and hydroxyapatite in panels A and B. This result indicates that loss of gross structure (including intact surface) leads to a marked change in the protein-binding capability of intact lesions. To legitimise these comparisons, both affinity matrices (particulate hydroxyapatite, MIH enamel) were mortar-ground to equal consistencies (coarse powder) before assay.

Mock oral fluid was prepared by empirically spiking saliva with serum and erythrocyte lysate so that major proteins from all three components were similarly abundant (FIG. 4B). To assay protein binding, oral fluid was incubated with 0.1 volumes hydroxyapatite (from Sigma, St Louis, Mo., USA) or MIH enamel for 60 min at 20° C. then centrifuged (2,000 g, 2 min). After washing in 3 volumes 20 mM Tris-HCl (pH 8.0), the pellet was extracted with trifluoroacetic acid and SDS as described above for enamel.

Results

MIH Enamel is Enriched with Non-Amelogenin Proteins

Profiling of enamel proteins has provided useful insights to the pathogenesis of fluorosis and amelogenesis imperfecta, particularly by linking amelogenin levels with clinical properties. Accordingly, unfixed MIH enamel specimens were investigated using an SDS-PAGE approach. Unlike normal enamel, MIH enamel gave visible precipitates when dissolved in acid, suggesting a relatively high protein content. As shown in FIG. 1, quantification of acid-insoluble protein from five severe lesions yielded values 3- to 15-fold higher than normal (0.3-1.5% protein w/w). Similarly, SDS-PAGE with Coomassie staining revealed numerous protein bands in MIH enamel contrasting with barely detectable banding in normal enamel (FIG. 2A). Since amelogenins were undetected (FIG. 2A, 20-25 kDa region), immunoblotting was used for higher sensitivity. Anti-amelogenin also failed to detect intact amelogenins in MIH enamel, but degradative fragments were observed in some specimens (FIG. 2B, specimen 11). Amelogenins were undetectable in normal enamel under these conditions (not shown). Quantitative comparison with secretion-phase enamel matrix showed that MIH enamel contained only 0.12%±0.06% (±SE, n=6) the amount of total detectable amelogenins (FIG. 2B, 8- to 25-kDa region). It was concluded that MIH enamel is protein-enriched, and for pathogenic reasons other than amelogenin retention.

Body Fluid Proteins Predominate in MIH Enamel

Figure 3:
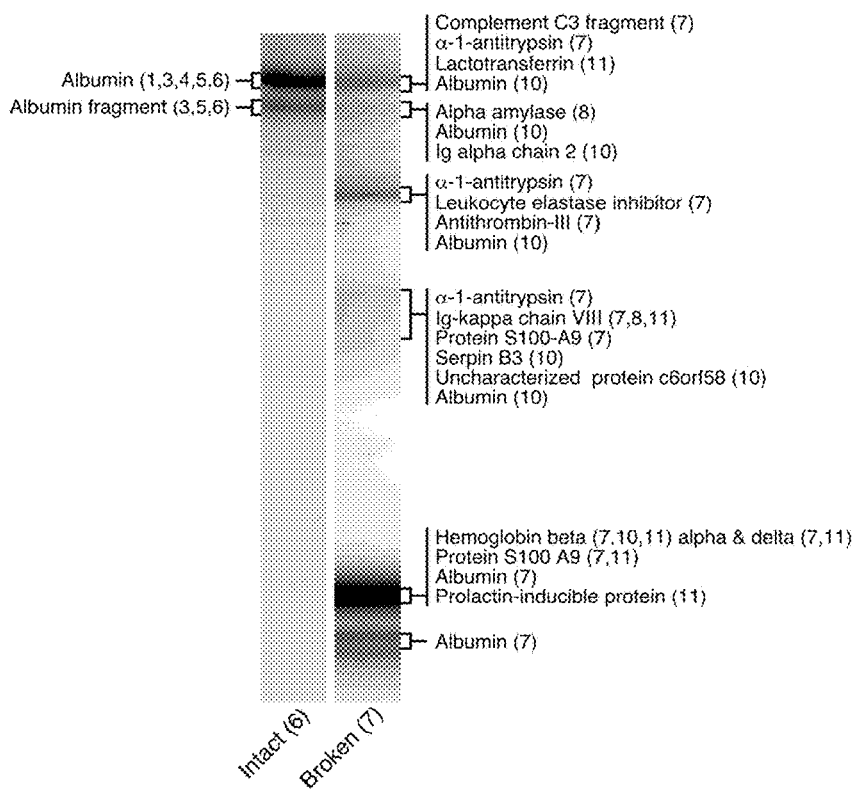
FIG. 3 lists the results of proteomic analysis of intact and broken MIH lesions, which reveals numerous body fluid proteins in MIH enamel. The indicated major gel bands from intact and broken lesions (FIG. 2A, specimens 1-11) were subjected to proteomic identification, as documented more fully in Table 1. The figure depicts the proteins identified in each band, and the specimens in which these identifications were made (specimen numbers in parentheses). Gel lanes for specimens 6 and 7 are reproduced from FIG. 2A to illustrate intact and broken lesions, respectively.

To identify the major protein constituents of MIH enamel, SDS-PAGE bands were subjected to proteomic analysis. As shown in FIG. 3 and Table 1, a variety of proteins were identified (16 distinct gene products), 13 of which are found in saliva and crevicular fluid. The three others (haemoglobin, albumin, complement C3) are major components of blood. Consequently all major proteins identified in MIH enamel are normally associated with body fluids found intraorally.

TABLE I

Proteins identified in MIH enamel with intact surface (specimens 1 to 6) and with post-eruptive breakdown (specimens 7 to 11).

| Name (UniProt acc.) | Body fluid localization | Mass (kDa) Observed | Mass (kDa) Theoretical | Specimens identified in | Peptides (n) | Coverage (%) | MASCOT Score |
|---|---|---|---|---|---|---|---|
| Serum albumin (P02768) | Serum, saliva, GCF | 70 | 69 | 1 | 16 | 21 | 426 |
| | | | | 3 | 2 | 4 | 89 |
| | | | | 4 | 15 | 26 | 471 |
| | | | | 5 | 10 | 21 | 197 |
| | | | | 6 | 9 | 15 | 389 |
| | | | | 10 | 7 | 14 | 212 |
| | | 60 | | 3 | 3 | 8 | 87 |
| | | | | 5 | 7 | 18 | 323 |
| | | | | 6 | 12 | 15 | 389 |
| | | | | 10 | 14 | 24 | 461 |
| | | 40 | | 10 | 2 | 5 | 47 |
| | | 32 | | 10 | 3 | 2 | 50 |
| | | 10 | | 7 | 5 | 8 | 136 |
| Complement C3 beta chain (P01024) | Serum | 70 | 71 | 7 | 2 | 1 | 165 |
| Alpha-1-antitrypsin (P01009) | Serum, saliva, GCF | 40 | 44 | 7 | 14 | 33 | 308 |
| | | 25-30 | | 7 | 3 | 16 | 122 |
| Protein S100-A9 (P06702) | Saliva, GCF | 25-30 | 13 | 7 | 3 | 24 | 54 |
| | | 13 | | 7 | 5 | 37 | 212 |
| | | 13 | | 11 | 6 | 56 | 158 |
| Lactotransferrin (P02788) | Saliva, GCF | 70 | 78 | 11 | 2 | 4 | 155 |
| Leukocyte elastase inhibitor (P30740) | Blood, saliva | 40 | 43 | 7 | 4 | 9 | 172 |
| Antithrombin-III (P01008) | Serum, saliva | 40 | 53 | 7 | 2 | 4 | 121 |
| Hemoglobin subunit alpha (P69905) | Blood, saliva | 13 | 15 | 7 | 6 | 38 | 117 |
| | | 13 | | 11 | 5 | 23 | 115 |
| Hemoglobin subunit beta (P68871) | Blood, saliva, GCF | 13 | 16 | 7 | 12 | 63 | 374 |
| | | 13 | | 10 | 2 | 12 | 51 |
| | | 13 | | 11 | 11 | 63 | 207 |
| Hemoglobin subunit delta (P02042) | Blood, saliva | 13 | 16 | 7 | 8 | 40 | 190 |
| | | 13 | | 11 | 6 | 50 | 145 |
| Prolactin-inducible protein (P12273) | Saliva | 13 | 17 | 11 | 2 | 15 | 85 |
| Alpha amylase I (P04745) | Saliva | 60 | 57 | 8 | 2 | 7 | 131 |
| Ig kappa chain V-III region SIE (P01620) | Blood, saliva | 25-30 | 12 | 7 | 2 | 16 | 130 |
| | | 25-30 | | 8 | 2 | 16 | 67 |
| | | 25-30 | | 11 | 2 | 16 | 91 |
| Ig alpha-2 chain C region (P01877) | Blood, saliva | 60 | 37 | 10 | 3 | 7 | 109 |
| Uncharacterized protein c6orf58 (Q6P5S2) | Saliva | 32 | 38 | 10 | 4 | 14 | 68 |
| Serpin B3 (P29508) | Blood, saliva | 27 | 45 | 10 | 2 | 4 | 48 |

Intact and Broken MIH Lesions have Distinct Protein Profiles

Given the clinical diversity of MIH lesions (colour, consistency, size, surface integrity), it was investigated whether the different presentations have distinct protein compositions. Appraisal of the protein profiles (FIG. 2A) led to the hypothesis that integrity of the enamel surface had a major influence. Notably, when lesions were grouped as "intact" and "broken", the protein-banding patterns appeared qualitatively similar within each group, but two striking differences were apparent between the groups (FIG. 2A, 12-kDa & 66-kDa regions). The 12-kDa band, which was obvious in broken but not intact lesions, routinely contained haemoglobin as a major component (FIG. 3). Conversely, in intact lesions the 66-kDa band routinely contained albumin only, unlike broken lesions where albumin was found infrequently at lower levels.

Figure 2:
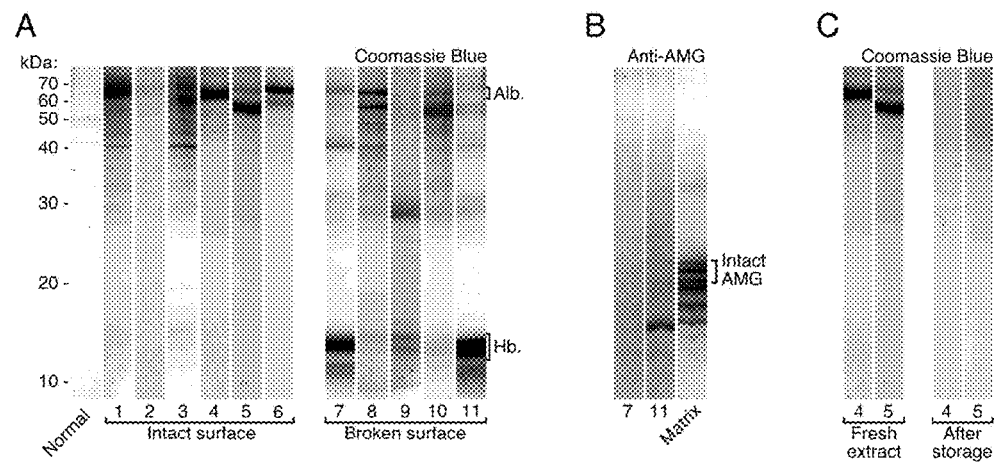
FIG. 2 illustrates that intact and broken MIH lesions have distinct protein profiles. Acid-insoluble proteins from MIH lesions and normal enamel (normal) were subjected to SDS-PAGE and stained with Coomassie Blue or immunoblotted with amelogenin antibodies (anti-AMG) as indicated. (A) Comparison of intact-surface and broken-surface lesions (specimens 1-6 and 7-11, respectively), showing distinct patterns for the major protein bands. The positions of albumin and haemoglobin are indicated (Alb, Hb). (B) Comparison of MIH specimens with secretion-phase enamel matrix from rat, which served as a control for predominantly intact amelogenins (AMG). Specimens 7 and 11 are representative of lesions with low or appreciable amounts of amelogenin fragments respectively. For quantification, cross-immunoreactivity between rat and human amelogenins was normalized using a human amelogenin standard (from Abnova, Taipei City, Taiwan). (C) Profiles for two intact lesions, comparing the first gel run using fresh extracts with a second run after storage of the same SDS-extracts for 16 wk at −20° C. Note disappearance of the major bands at 66 kDa (albumin).

The stability of the protein profiles was also queried, noting evidence of protein degradation (FIG. 3: albumin, complement C3) and the key role of proteolysis in enamel maturation. Indeed, when SDS-solubilized samples from FIG. 2A were reanalysed after frozen storage, the albumin bands had completely disappeared from intact specimens (FIG. 2C). Broken specimens were largely unaffected however (not shown). Protease inhibitors had little effect on the profiles of fresh MIH samples when added during the initial SDS-solubilisation step (not shown). These results highlighted the risk of artefactual proteolysis and hence only first-run samples are reported (FIGS. 1 to 3). It was concluded that intact and broken lesions consistently have distinct protein profiles, supporting the hypothesis that surface integrity influences the protein composition of MIH enamel.

Protein Composition of MIH Enamel Varies with Surface Integrity

It is known that MIH lesions exhibit sub-surface porosity and that albumin and haemoglobin bind avidly to hydroxyapatite. Accordingly, it was posited that oral-fluid proteins permeate MIH enamel and selectively bind to hydroxyapatite crystals, subject to absence of an intact surface layer. When broken lesions were compared with saliva, serum and erythrocytes, collective similarities in the protein-banding patterns were found (FIG. 4A). In contrast, intact lesions bore an intriguing resemblance to serum alone. These results accorded with oral-fluid proteins being excluded from intact but not broken lesions. Next, a broken lesion was modelled by exposing hydroxyapatite powder to mock oral fluid (combination of saliva, serum and erythrocyte extract). Profiling of the hydroxyapatite-bound fraction (FIG. 4B) revealed remarkable similarity to broken lesions (FIGS. 2A, 4A). When hydroxyapatite was substituted with powdered enamel made from an intact lesion (i.e. to model breakage of the surface layer), the profile was again similar to broken lesions (FIG. 4C). These results indicated that the protein composition of MIH enamel is strongly influenced by integrity of the enamel surface.

Figure 5:
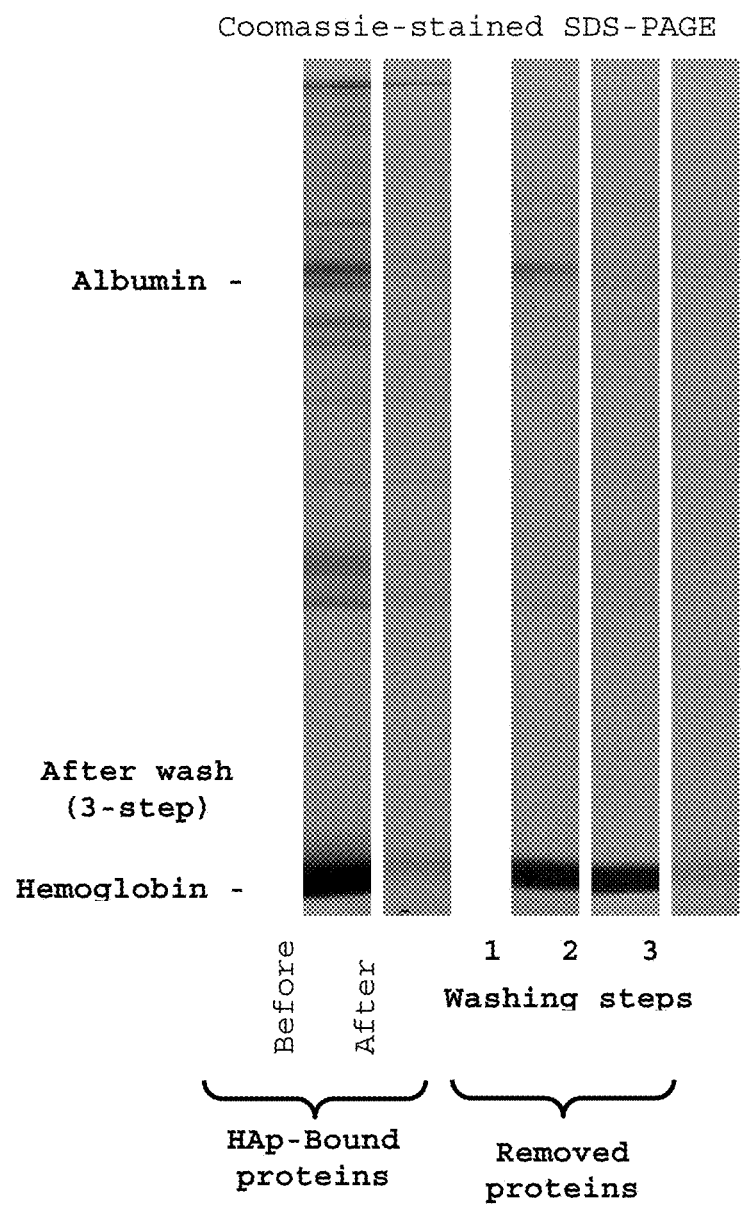
FIG. 5 depicts a hydroxyapatite-binding assay (Coomassie-stained SDS-PAGE) showing that hemoglobin and albumin from mock oral fluid are bound by hydroxyapatite. A three-step washing procedure comprising washing sequentially in each of 5 mM $MgCl_2$, 1 M $MgCl_2$, and 0.4 M $NaH_2PO_4$ each for 5 min removed >90% of protein from hydroxyapatite.

When mock oral fluid comprising albumin and hemoglobin was applied to hydroxyapatite, albumin and hemoglobin bound to the hydroxyapatite (FIG. 5). Washing sequentially in each of 5 mM $MgCl_2$, 1 M $MgCl_2$, and 0.4 M $NaH_2PO_4$ each for 5 min removed >90% of protein from hydroxyapatite (FIG. 5).

Discussion

Given growing concerns about MIH worldwide, a pressing need exists to elucidate the protein composition of hypomineralized enamel. It is disclosed herein that MIH enamel has substantially higher protein content than normal, but a near-normal level of residual amelogenins. This characteristic distinguishes MIH from hypomaturation defects that contain high residual amelogenins (amelogenesis imperfecta, fluorosis) and in turn typifies MIH as a hypocalcification defect. Secondly, MIH enamel was found to have accumulated various proteins from oral fluid and blood, with differential incorporation depending on integrity of the enamel surface. Pathogenically, these results point to a pre-eruptive disturbance of mineralisation involving albumin and, in cases with post-eruptive breakdown, subsequent protein adsorption to the exposed hydroxyapatite matrix. These insights to the pathogenesis and properties of MIH enamel hold significance for the prevention, diagnosis and treatment of MIH.

The present results help to explain the clinical and biophysical properties of MIH enamel. The observed 3-fold to 15-fold elevation in protein content is similar to reports for amelogenesis imperfecta and fluorosis (2.5-fold to 30-fold) and appears sufficient to account for the characteristic mechanical weakness of MIH enamel. The low residual content of amelogenins likens MIH enamel to hypocalcified types of amelogenesis imperfecta. Enamel from the latter disorders is described clinically as markedly softer than normal and friable or cheesy, which coincides with descriptions of MIH enamel. At the protein level, MIH enamel appears distinguishable from hypocalcified types of amelogenesis imperfecta and fluorosis, particularly based on its uniquely high content of albumin. However, all conditions are characterised by porous hydroxyapatite.

These results also elucidate the pathogenesis of MIH, pointing to pre- and post-eruptive steps that are mechanistically distinct. Pre-eruptively, the normal thickness and low amelogenin content of MIH enamel (<0.2% of secretion-phase level) indicates that amelogenins are secreted and then removed effectively. It follows that MIH is not a maturation defect primarily. By analogy to hypocalcified amelogenesis imperfecta, attention therefore turns to defective initiation of mineralisation. Protein profiling indicated that albumin accumulates in MIH enamel despite near-complete removal of amelogenins.

In other words, hypocalcification is a subtype of hypomineralisation, the other subtype being hypomaturation. As shown herein, MIH and some types of amelogenesis imperfecta, and probably some types of fluorosis too, are distinguished as hypocalcification defects in that they have low amounts of amelogenin. That is, the normal process of amelogenin removal (enamel maturation) has occurred, but calcification has not occurred. In hypomaturation defects, however, (immature types of amelogenesis imperfecta and fluorosis), amelogenin removal (enamel maturation) has not occurred to a major degree and it is the continued presence of amelogenin that impedes calcification.

Amelogenin levels are relatively low in hypocalcification types of DDD/hypomineralisation, but closer to normal levels in hypomaturation types of DDD/hypomineralisation (such as some types of amelogenesis imperfecta and dental fluorosis). Therefore, variations in levels both of amelogenin and the remaining proteins disclosed herein bound to porous dental hydroxyapatite could be informative (e.g. diagnostic) individually or in combination, for example as a ratio.

For the first time, these results demonstrate extravasated albumin being accumulated in malforming human enamel. Notably, intact lesions were found to contain albumin but not numerous oral-fluid proteins with demonstrated hydroxyapatite-binding potential. That albumin but not haemoglobin was prominent may be attributed either to a minor vascular leak of serum rather than whole blood, or to high proteolytic stability of albumin relative to haemoglobin and other blood proteins during enamel maturation. Indeed, albumin is resistant to kallikrein-related peptidase 4, the major protease implicated in amelogenin removal.

These results also imply that another pathogenetic step follows post-eruptive breakdown of the enamel surface. This second step involves relatively promiscuous binding of oral-fluid proteins to the exposed hydroxyapatite matrix.

The proteins identified herein have potential utility as biomarkers for characterizing MIH lesions clinically.

Example 2—Production and Testing of a Probe for Porous Hydroxyapatite

Materials and Methods

SMCC (succinimidyl 4-[N-maleimidomethyl] cyclohexanecarboxylic acid N-hydroxysuccinimide ester; CAS#: 64987-85-5) is a non-cleavable heterobifunctional cross-linker with amine and sulfhydryl reactivity separated by a spacer arm of 8.3 Å. Amido black (CAS#: 1064-48-8) is a common blue/black stain used here as a coloured reporter which contains a primary amine group. Hemoglobin from cow (CAS#: 9008-02-0) is a heterotetramer consisting of 2 pairs of polypeptide chains (α and β; SEQ ID NOs: 20 and 21, respectively). The β-chain has a single solvent-exposed sulfhydryl-containing cysteine residue, while the α-chain has no cysteines.

SMCC (75 mM in dimethyl sulfoxide) was added to 9-volumes of amido black (37.5 mM in phosphate-buffered saline (PBS, 137 mM NaCl, 2.7 mM KCl, 10 mM sodium phosphate dibasic, pH 7.4)) and incubated 30 minutes at 21° C. The 5-fold molar excess of Amido black ensured maximal labelling of SMCC (creating a maleimide-activated coloured reporter, FIG. 27). After conjugation, the solution was desiccated by vacuum centrifugation and stored at −80° C.

Hemoglobin (20 mg/ml; 0.65 µmole cysteine-thiol/ml) was prepared by dissolving in PBS that contained 10 mM TCEP (tris(2-carboxyethyl)phosphine, a non-thiol reducing agent used to maintain cystine-sulfhydryl state) and 5 mM EDTA (ethylenediaminetetraacetic acid, a metal chelator used to reduce potential for oxidant/radical catalysis and subsequent thiol oxidation). After a 30 minute incubation at 21° C., reduced hemoglobin was dialysed against 1,000-volumes of PBS for 2 hours to deplete TCEP and EDTA (this step may be optional). The hemoglobin was taken to the next step immediately to minimise cysteine-thiol oxidation.

The desiccated maleimide-activated Amido black was dissolved in Hemoglobin at a Amido black:thiol molar ratio of 10:1 to ensure maximal labelling of hemoglobin. After incubating for 2 hours at 21° C., Amido black-conjugated hemoglobin was dialysed extensively against PBS (until dialysate remained uncoloured, for 1 ml this took 24 to 48 hours) to remove non-covalently bound amido black. After dialysis, the probe was ready for use.

Results

Figure 29:
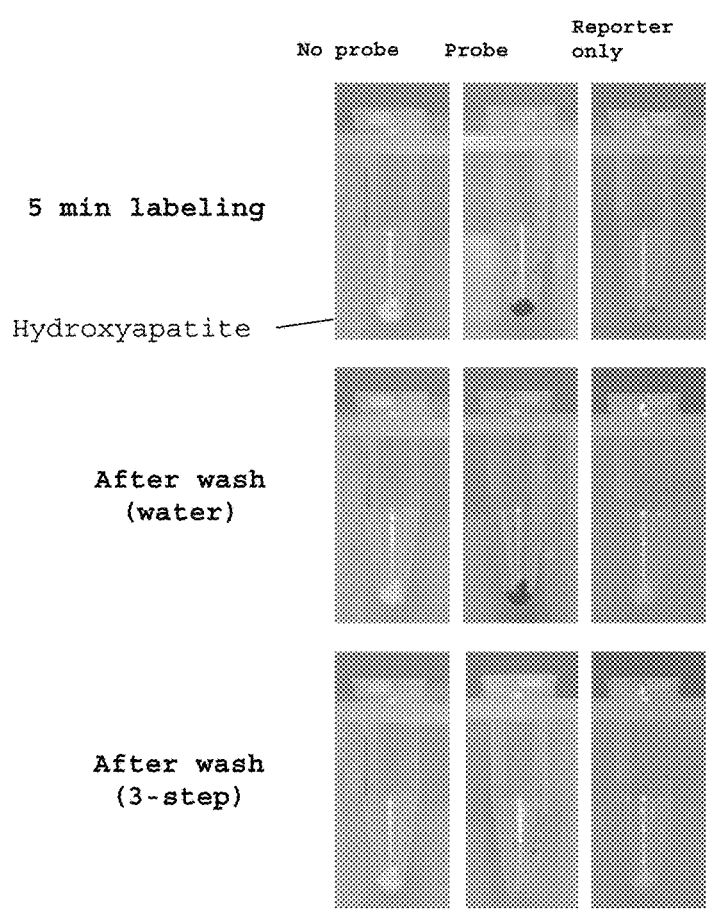
FIG. 29 depicts the in vitro binding to hydroxyapatite of a probe produced according to FIGS. 27 and 28 and Example 2. The probe comprised hemoglobin (Hb), a black-blue coloured reporter (amido black) and a linker. Within 5 min of applying the probe, hydroxyapatite changed to dark blue. The probe withstood washing in water, whereas coloured reporter only (i.e. not linked to Hb) was removed by washing in water. The probe was removed from hydroxyapatite by a three-step washing procedure comprising washing sequentially in each of 5 mM $MgCl_2$, 1 M $MgCl_2$, and 0.4 M $NaH_2PO_4$ each for 5 min.

Within 5 min of applying the probe, hydroxyapatite changed in colour from white to dark blue (FIG. 29). The probe withstood washing in water, whereas Amido black alone (i.e. not linked to Hb) was removed by washing in water. The probe was removed from hydroxyapatite with a three-step washing procedure that comprised washing sequentially in each of 5 mM $MgCl_2$, 1 M $MgCl_2$, and 0.4 M $NaH_2PO_4$ for 5 min (FIG. 29).

Discussion

A key design requirement was the preservation of hemoglobin's hydroxyapatite-binding function after conjugation to the coloured reporter. Hemoglobin's cysteine-thiols were targeted because two of the four protein subunits carry a single cysteine (not at binding interfaces); the other two subunits lack cysteine. The resulting tetramer probe therefore contains two unmodified protein subunits, thereby maintaining at least half the native hydroxyapatite-binding sites per functional unit. A 2-step method was exemplified: the first produced a coloured reporter-SMCC conjugate (FIG. 27); the second used the coloured reporter-SMCC conjugate to label hemoglobin (FIG. 28). Here proof-of-principle has been established for design, production and testing of a novel probe that detects porous hydroxyapatite.

Figure 30:
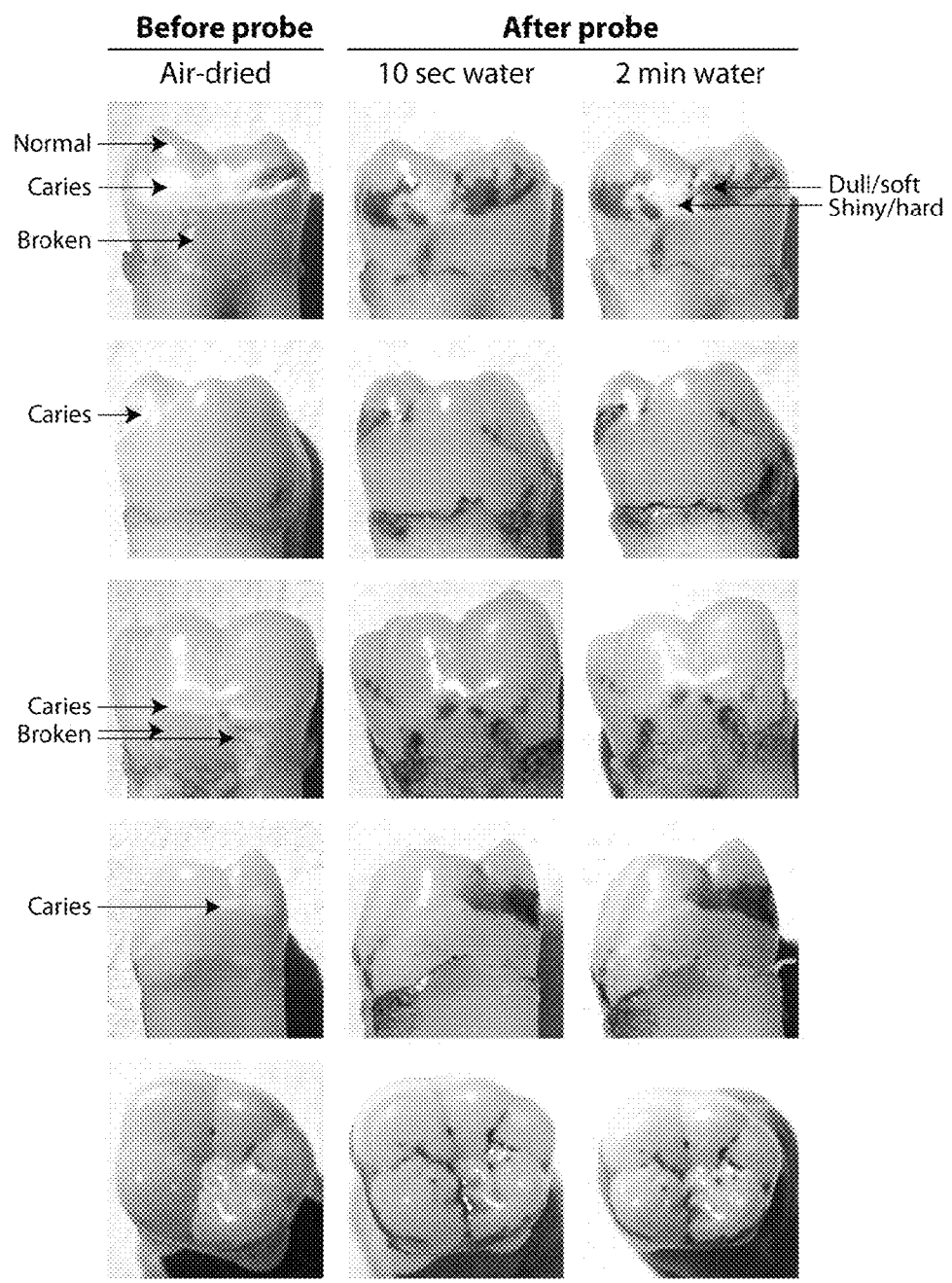
FIG. 30 depicts the results of Example 3 that demonstrate specific binding of a probe produced according to Example 2 to porous dental enamel.

Example 3—the Probe Binds to Porous Dental Enamel Specifically (FIG. 30)

Methods

To test whether the probe of Example 2 binds to porous enamel specifically, a complex carious lesion was coated with the probe then washed thoroughly.

A human first molar that had a large region of caries (porous enamel, white opaque region) was photographed before and after application of the probe (FIG. 30). The probe was applied to the whole crown region using a brush for a period of one minute. After application of the probe, the tooth was rinsed under running water for 10 seconds, photographed, then the tooth was washed again for a further two minutes and photographed.

Results

Normal enamel was not labelled.

Regions of overt caries were labelled strongly and specifically, but labelling was patchy in some places. The unlabelled carious regions exhibited a shiny surface that was resistant to scratching, whereas labelled regions had a dull surface that could be scratched readily. This indicates that the areas of patchy unlabelled caries may be due to remineralisation of the surface layer. Thus, the probe is capable of discriminating between active and inactive caries.

Regions of enamel broken during extraction of the tooth (forceps imprints) were also labelled indicating that the probe can detect regions of enamel that have a breached surface.

The probe provided a stable level of labelling, independent of water-rinsing time.

Figure 31:
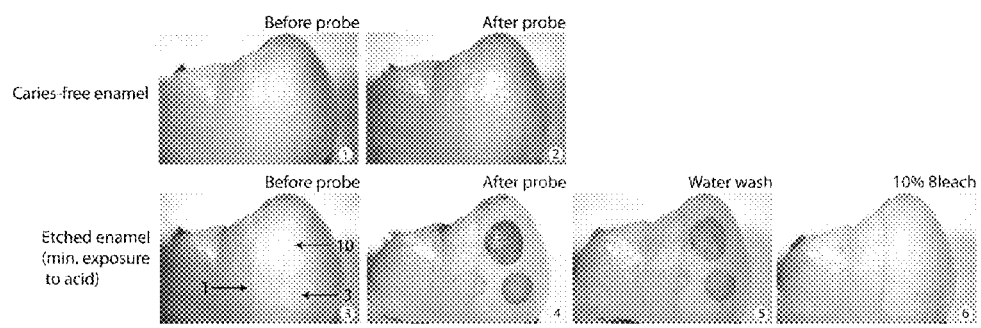
FIG. 31 depicts the results of Example 4 that demonstrate that a probe produced according to Example 2 can specifically detect early demineralisation of surface enamel (model of incipient caries).

Example 4—the Probe can Specifically Detect Early Demineralisation of Surface Enamel (Model of Incipient Caries) (FIG. 31)

Methods

To test whether the probe of Example 2 can specifically detect early caries, artificial carious lesions were produced on normal surface enamel using spots of strong acid (before application of probe).

A human first molar was shown by photography before and after application of the probe to be caries-free prior to acid-treatment (FIG. 31). Three regions of enamel were then exposed to acid (0.5 µl 85% $H_3PO_4$) for 1, 3 or 10 minutes to introduce artificial carious lesions before washing in 100 ml TBS (25 mM Tris pH 7.2, 160 mM NaCl) for two minutes, then under running water for another two minutes. The tooth was air-dried and the probe was applied to the whole area for three minutes using a brush. After application, unbound probe was removed by first wiping with absorbent paper, then by rinsing under running water for 10 seconds. To remove bound probe, 10% bleach (0.4% NaClO) was applied with a brush for 10 seconds.

Results

The probe did not bind to any regions of the caries-free enamel.

Acid etch treatment yielded three regions of slightly opaque/dull enamel, which followed a dose-dependent severity profile (10>3>1 min). The three etched regions were all detected by the probe, in a severity-dependent manner; un-etched enamel was not labelled.

Probe binding resisted washing in water, although signal intensity diminished slightly. The probe could be quantitatively removed by application of 10% bleach for 10 seconds.

Figure 32:
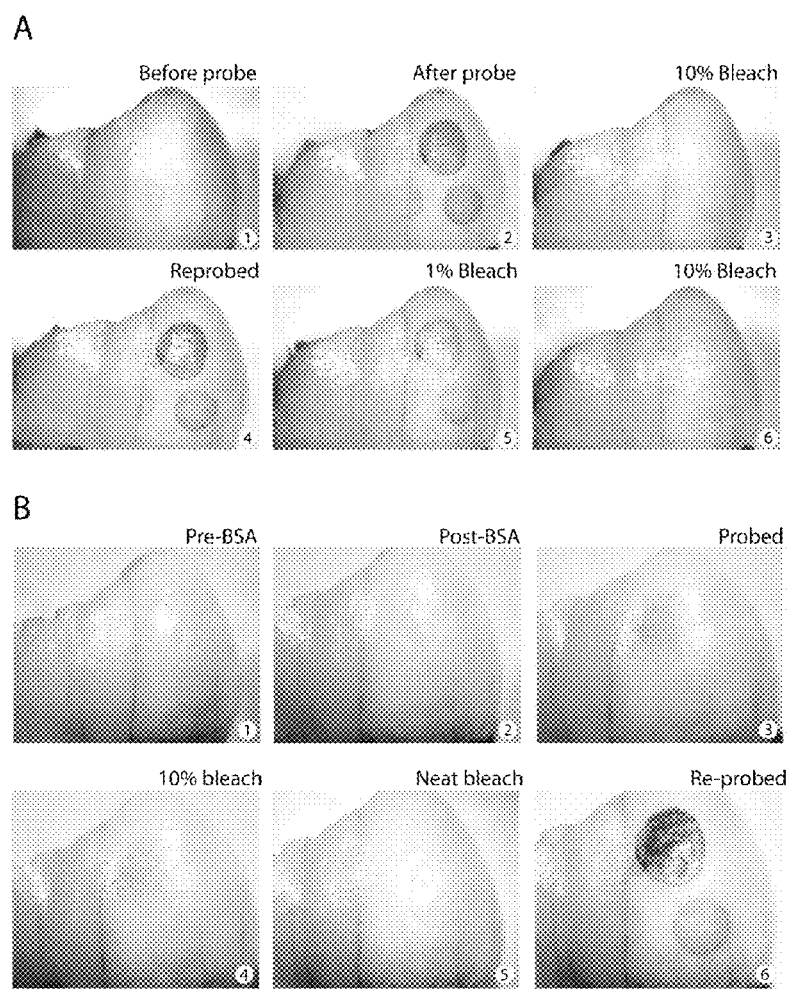
FIG. 32 depicts the results of Example 5 that demonstrate that the mechanism of action of a probe produced according to Example 2 is hydroxyapatite affinity.

Example 5—Probe's Mechanism of Action is Hydroxyapatite Affinity (FIG. 32)

Enamel from Example 4 (FIG. 31) was re-treated with probe of Example 2 to verify a hydroxyapatite-binding mechanism.

Methods (A)

To rule out a protein-staining mechanism, the probe was applied to etched enamel that had been bleach-treated (i.e. protein stripped).

Results (A)

Bleached enamel was labelled by the probe similarly to unbleached (FIG. 32, compare Panels A2 and A4). This finding rules out a protein-staining mechanism for the probe's labelling of etched enamel.

Methods (B)

It was proposed that, if the probe's mechanism of action is hydroxyapatite-binding, then BSA pre-treatment should block probe binding (competitive inhibition).

Enamel from Panel A was exposed to a known hydroxyapatite-binding protein (10% bovine serum albumin, BSA) by applying with a brush for one minute, followed by water rinsing for one minute. After BSA treatment, the probe was applied as before. BSA was stripped by bleach treatment, and the probe re-applied.

Results (B)

Application of BSA did not alter appearance of the enamel (FIG. 32, Panel B2). BSA blocked binding of the probe (FIG. 32, Panel B3). Probe binding was restored after stripping BSA (FIG. 32, Panel B6). Together, these results demonstrate that the probe's mechanism of action is hydroxyapatite-binding, not protein-binding. Given the possibility of competitive inhibition by other hydroxyapatite-binding proteins, pre-treatment to strip proteins could improve probe sensitivity and so minimise false-negative results.

Figure 33:
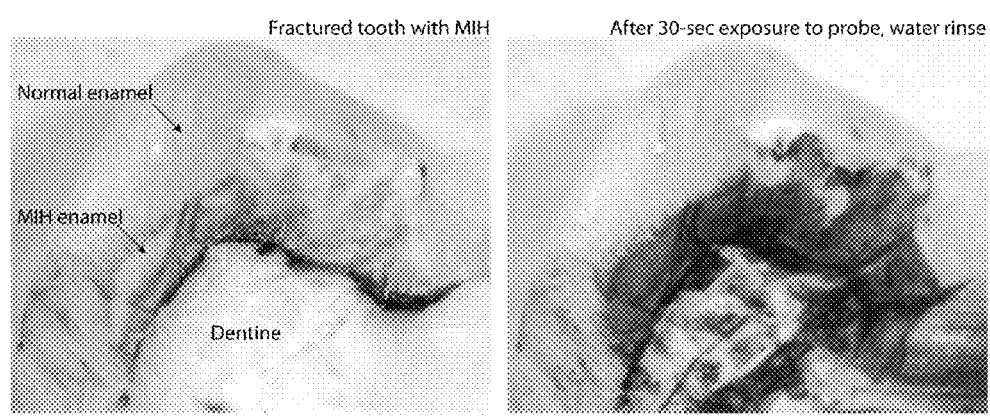
FIG. 33 depicts the results of Example 6 that demonstrate that a probe produced according to Example 2 specifically labels hypomineralised enamel and abnormal dentine. Normal enamel and dentine were unlabelled. Hypomineralised enamel was specifically and uniformly labelled an intense violet colour. Abnormal dentine was specifically and uniformly labelled a deep green colour.

Example 6—the Probe Specifically Labels Hypomineralised Enamel and Abnormal Dentine (FIG. 33)

Methods

To test whether the probe of Example 2 could be used to delineate abnormal dental tissues, a portion of tooth that contained normal and abnormal enamel & dentine was treated with the probe.

A fractured tooth that displayed a region of sub-surface hypomineralisation was chosen to mimic a clinically difficult case where lesion boundaries are obscure and complex. A brief pre-exposure to the probe led to demarcation of the enamel-dentine boundary. The specimen was then photographed before (left) and after (right) the probe was applied with a brush for 30 seconds (FIG. 33). After application, unbound probe was removed by rinsing in water for 30 seconds.

Results

Before application of the probe, several structures could be identified: (1) normal enamel which overlaid (2) hypomineralised enamel (pink in colour with a red border in some regions), (3) apparently normal dentine (hard) and (4) abnormal dentine (soft/leathery). After application of the probe, all four types of tissue could be readily discerned.

Normal enamel and dentine were unlabelled. Hypomineralised enamel was uniformly and specifically labelled an intense violet colour, which appeared to trace a very complex border throughout the subsurface region. Abnormal dentine (potentially due to caries and/or developmental defects) was specifically and uniformly labelled a deep green colour, which appeared to trace complex borders against normal dentine. Together, these data confirm that the probe can specifically label hypomineralised enamel and abnormal dentine.

Figure 34:
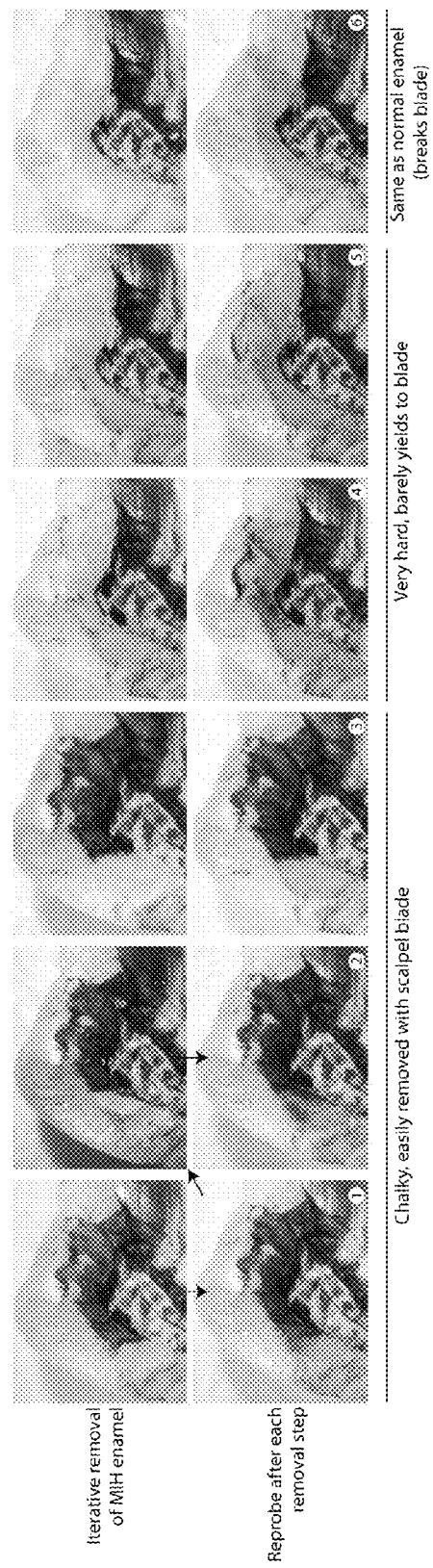
FIG. 34 depicts the results of Example 7 that demonstrate that a probe produced according to Example 2 can be used to guide removal of hypomineralised enamel.

Example 7—the Probe can be Used to Guide Removal of Hypomineralised Enamel (FIG. 34)

Methods

Hypomineralised enamel from Example 6 (FIG. 33) was removed using a scalpel blade and repeatedly re-probed with the probe of Example 2 to monitor progress. Physical characteristics of the enamel were noted at each step (FIG. 34, see description beneath panels).

Results

The upper panels of FIG. 34 show the specimen after removal of hypomineralised enamel, whereas the lower panels show the same specimen after application of the probe. Panels 1 to 3 show gradual removal of small regions of hypomineralised enamel. Panels 4 to 6 show attempted removal of the whole region, and regions of incomplete removal (compare upper and lower panels). Note that as hypomineralised enamel was removed, the physical characteristics changed markedly in parallel with degree of labelling, to the end-point where remaining enamel was physically uniform and unstained by the probe (Panel 6).

Abnormal dentine was not addressed in this example.

Figure 35:
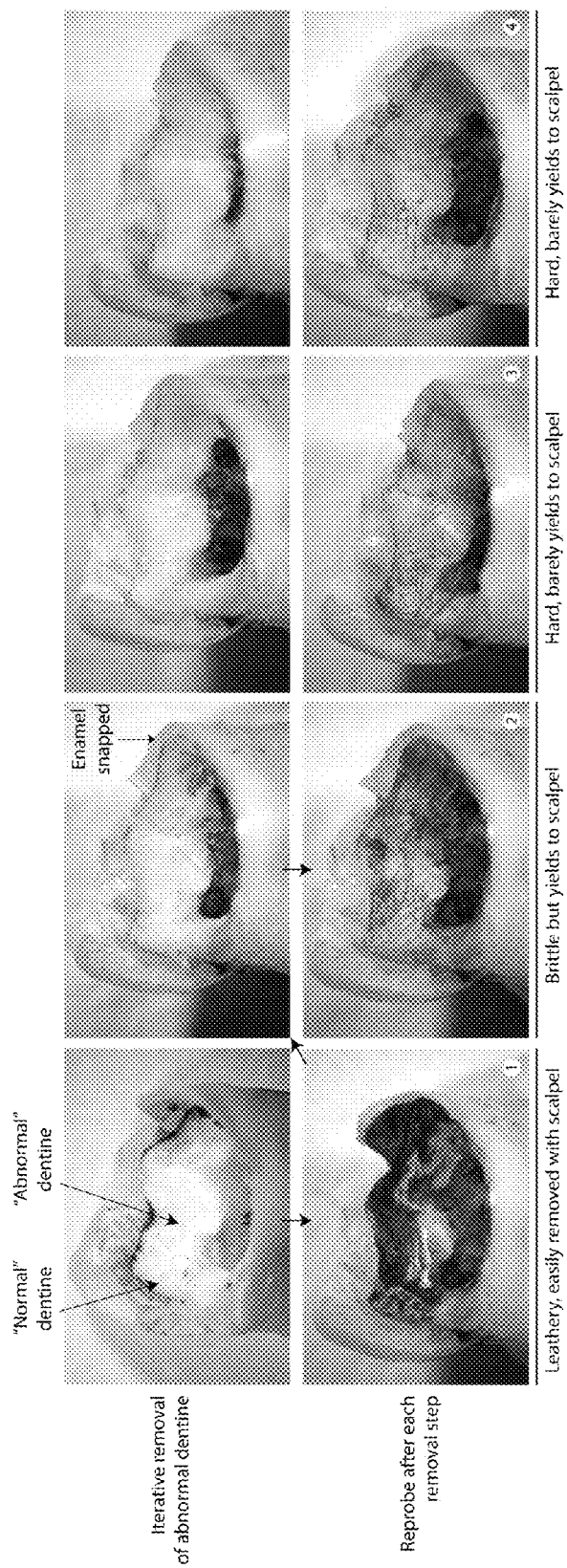
FIG. 35 depicts the results of Example 8 that demonstrate that a probe produced according to Example 2 can be used to guide removal of abnormal dentine.

Example 8—the Probe can be Used to Guide Removal of Abnormal Dentine (FIG. 35)

Methods

Abnormal dentine from Example 6 (FIG. 33) was removed using a scalpel blade and iteratively re-probed with the probe of Example 2 to monitor progress of removal. Physical characteristics of the dentine were noted at each step (FIG. 35, see description beneath panels).

Results

The upper panels of FIG. 35 show the specimen after removal of abnormal dentine, whereas the lower panels show the same specimen after application of the probe. Panel 1 shows intense staining of abnormal dentine, which is reduced sharply with removal and reprobing (e.g. compare lower panels 1 and 2). Reduced levels of labelling by the probe correlate with improved physical character of the dentine (e.g. in Panel 4, the dentine hardness was uniformly normal by physical assessment and largely unstained after application of the probe). Note that even after complete removal of abnormal dentine, a low level of background staining is apparent (presumably due to dentine's higher porosity relative to enamel).

Figure 36:
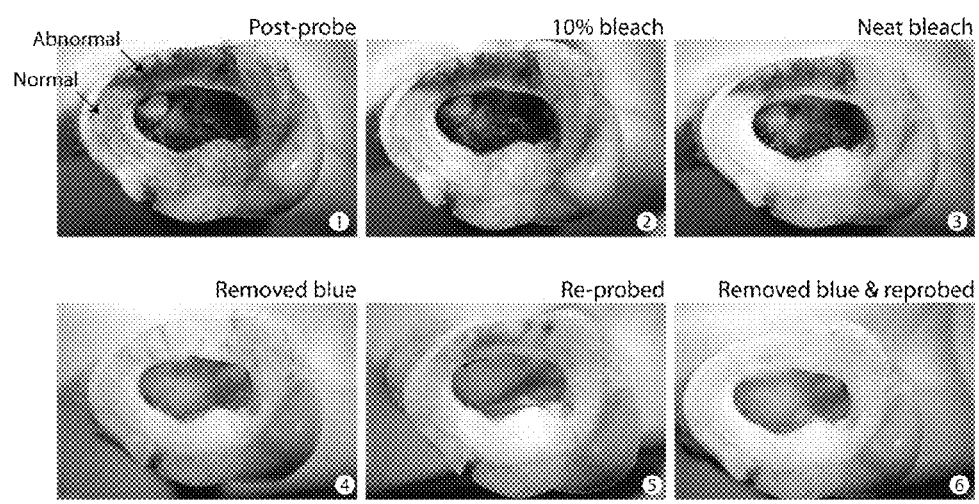
FIG. 36 depicts the results of Example 9 that demonstrate that detection of abnormal dentine according to Example 8 can be improved using a bleach wash.

Example 9—Detection of Abnormal Dentine by the Probe can be Improved by a Bleach Wash (FIG. 36)

Methods

To test whether the probe's specificity for dentine, as shown in Example 8, could be improved, a bleach wash was used to reduce staining of normal dentine.

A human molar with exposed normal and abnormal dentine was exposed to the probe of Example 2 (brush application for one minute followed by water rinse for one minute) and subsequently exposed to a bleach wash (applied with brush for 10 seconds, then water rinsed for one minute). Following probe/bleach application, labelled regions were removed with a scalpel blade then re-probed/bleached to monitor progress (FIG. 36).

Results

Abnormal dentine was preferentially detected by the probe, however background staining of normal dentine decreased confidence in border demarcation. Application of 10% bleach (0.4% NaOCl) for 10 seconds improved resolution by reducing labelling in normal dentine, but not in abnormal. Application of neat bleach (4% NaOCl) for 10 seconds completely removed labelling from normal dentine, without affecting labelling of abnormal dentine, resulting in much clearer delineation of abnormal dentine.

After neat bleach, abnormal dentine was removed (Panel 4) then re-probed/bleached (Panel 5), showing that most, but not all, abnormal dentine was removed. Another removal/re-probe/bleach step showed that abnormal dentine was completely removed. The remaining dentine was physically indistinguishable from normal dentine.

Together, these results suggest that a protein-stripping step after application of the probe can help reduce background labelling of normal dentine, reducing potential false-positive readouts.

Figure 37:
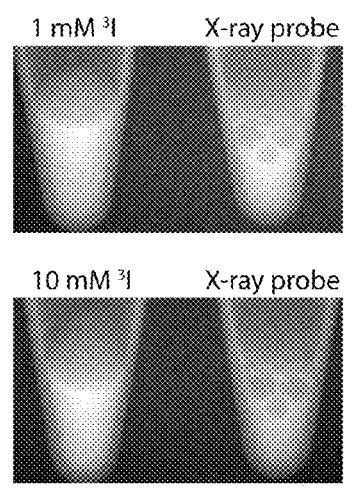
FIG. 37 depicts the results of Example 10 that demonstrate that the probe can be radio-opaque, which can be achieved by substituting the blue chromophore (amido black) of Example 2 for amino-2,4,6-triiodoisophthalic acid ($^3$I).

Example 10—the Probe can be Opaque to X-rays (FIG. 37)

Methods

The probe was made radio-opaque by substituting the blue chromophore (amido black) of Example 2 for 5-amino-2,4,6-triiodoisophthalic acid ($^3$I), a precursor compound used in medical radiography (e.g. for cerebral angiography). This compound was chosen due to the availability of a single primary amine that could be used for coupling with the same cross-linker used in the blue probe.

To couple $^3$I to hemoglobin, the following procedure was used:

1. 1.25 mg of SMCC (cross-linker) was dissolved in 50 μl DMSO (75 mM SMCC).
2. $^3$I was prepared as follows: 30 mg was dissolve in 1 ml 0.1 M NaOH (50 mM $^3$I), 250 μl 0.1 M HEPES pH 7.0 was added, then pH was adjusted to 7 with 1 μl additions of 5 M NaOH; such that the final solution was 40 mM $^3$I, 20 mM HEPES pH 7.
3. 400 μl of $^3$I solution was added to 50 μl 75 mM SMCC in DMSO and incubated at room temperature for 30 minutes to generate $^3$I-activated SMCC.
4. The $^3$I-SMCC was then lyophilised by vacuum centrifugation.
5. The resultant pellet was taken up in 20 μl of DMSO and 100 μl of 20 mg/ml hemoglobin was added, then the solution was incubated at room temperature for 60 min to couple $^3$I to cysteine thiols in hemoglobin.
6. The resultant $^3$I-Hb was then centrifuged (20,000×g for 5 minutes) before dialysis (10-kDa MWCO) overnight against 25 mM Tris pH 7.2, 160 mM NaCl.
7. The resulting dialysate was collected and stored at −20° C.

To assess the degree of radio-opacity conferred on the probe, it was subjected to X-ray radiography (65 kV, 8 mA, 0.5 second exposure) alongside radio-opaque standards (1 and 10 mM $^3$I).

Results

The X-ray probe was radio-opaque to a degree between 1 and 10 mM $^3$I (FIG. 37). Density analysis suggested radio-opacity was equivalent to a 1.5-2.5 mM solution of $^3$I. These results confirm that the probe can be made opaque to X-rays.

Figure 38:
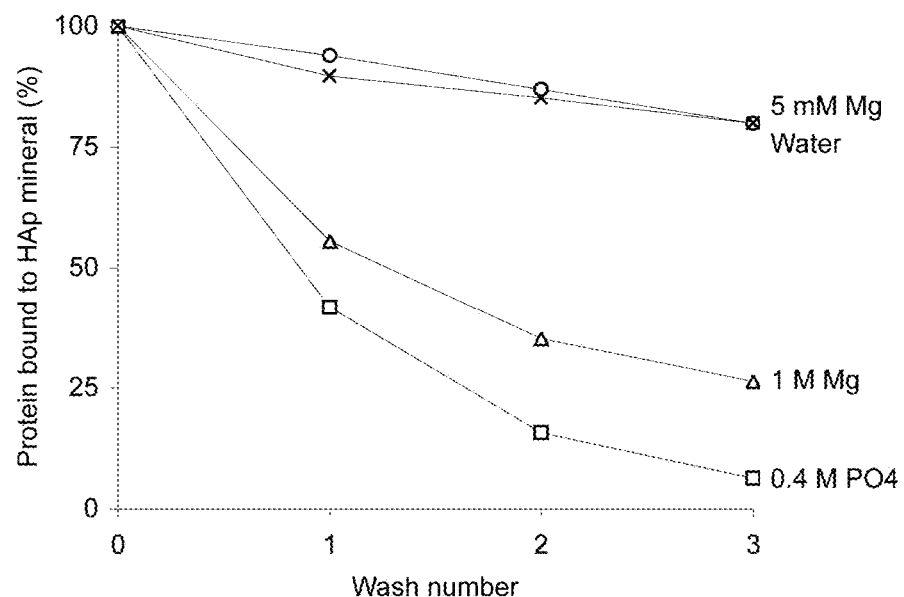
FIG. 38 depicts the results of Example 11 that demonstrate the relative effectiveness of washing solutions comprising $Mg^{2+}$ or $PO_4$ in removing proteins bound to pure hydroxyapatite.

Example 11—Analysis of Washing Solutions Using Pure Hydroxyapatite (FIG. 38)

Methods

To examine the relative effectiveness of each wash solution, they were individually tested using an in vitro model system (FIG. 38).

Pure hydroxyapatite (5 mg) was loaded with proteins from rat blood (100 μl of 10 mM Tris pH 7.2 which contained 10 μl Hb extract and 2 μl neat serum) for 10 minutes at room temperature with constant shaking. Protein-loaded hydroxyapatite was sedimented by centrifugation at 2,000×g for 30 seconds, the supernatant was discarded then the pellet was washed with 300 μl 10 mM Tris pH 7.2 for 30 seconds to remove unbound interstitial components.

Protein-hydroxyapatite was then exposed to 100 μl of various wash components (water, 5 mM $MgCl_2$, 1 M $MgCl_2$ or 0.4 M $NaH_2PO_4$) for 2 minutes at room temperature with mixing before centrifugation. Washes were collected and Protein-hydroxyapatite was washed another two times with the same washing solution. After three wash steps, the Protein-hydroxyapatite was dissolved in 100 μl 10% trifluoroacetic acid (TFA), and precipitated proteins collected by centrifugation (2,000×g for 2 minutes), and pellets were dissolved in 100 μl of 2× SoB (0.125M Tris-HCl pH 6.8, 4% SDS, 20% Glycerol). Protein content in all fractions was assessed by densitometry of dot-blots stained with Amido Black.

Results

The relative capabilities of the washing solutions to remove protein from hydroxyapatite were:

0.4 M $PO_4$>1M $Mg^{2+}$>5 mM $Mg^{2+}$(no more effective than water).

Although $PO_4$ appeared to provide the best protein-removal, is was noted that the hydroxyapatite remained a pink colour even after 3 washes, whereas the 1M $Mg^{2+}$-treated hydroxyapatite became white after a single wash. This being the case, it appears 1M $MgCl_2$ and 0.4M $NaH_2PO_4$ are most effective at removing protein, and they have complementary activities (likely removing different classes of proteins).

Figure 39:
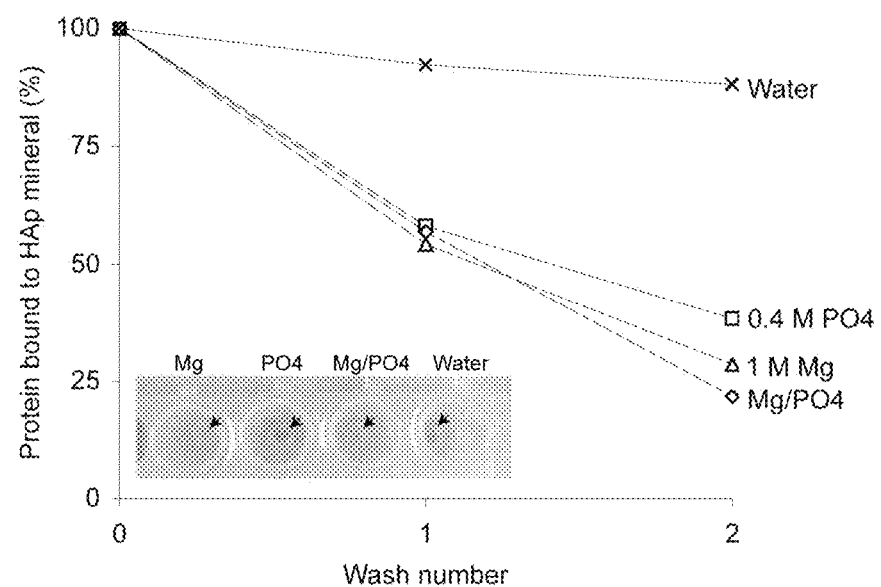
FIG. 39 depicts the results of Example 12 that demonstrate the relative effectiveness of separate or sequential application of washing solutions comprising $Mg^{2+}$ or $PO_4$ in removing proteins bound to pure hydroxyapatite.

Example 12—Analysis of $Mg^{2+}$ and $PO_4$ Separately or Sequentially Using Pure Hydroxyapatite (FIG. 39)

Methods

Pure hydroxyapatite was loaded with proteins, then subjected to 100 μl of various wash components (water, 1 M $MgCl_2$ or 0.4 M $NaH_2PO_4$) as for Example 11, except with two washes (instead of three) and 5 mM $MgCl_2$ was omitted. One tube received 1M $Mg^{2+}$ followed by 0.4 M $PO_4$. After the washes, hydroxyapatite pellets were photographed to record the colour (see inset), then protein content was assessed as for Example 11.

Results

All three washing solutions performed similarly, removing the majority of proteins after two washes, unlike water (FIG. 39).

Sequential washing with $Mg^{2+}$ then $PO_4$ produced the best result as assessed by protein removal and colour removal (inset: arrows indicate hydroxyapatite pellets after washing). It may be concluded that sequential washing with $Mg^{2+}$ and $PO_4$ provide optimal protein removal, in this hydroxyapatite model.

Figure 40:
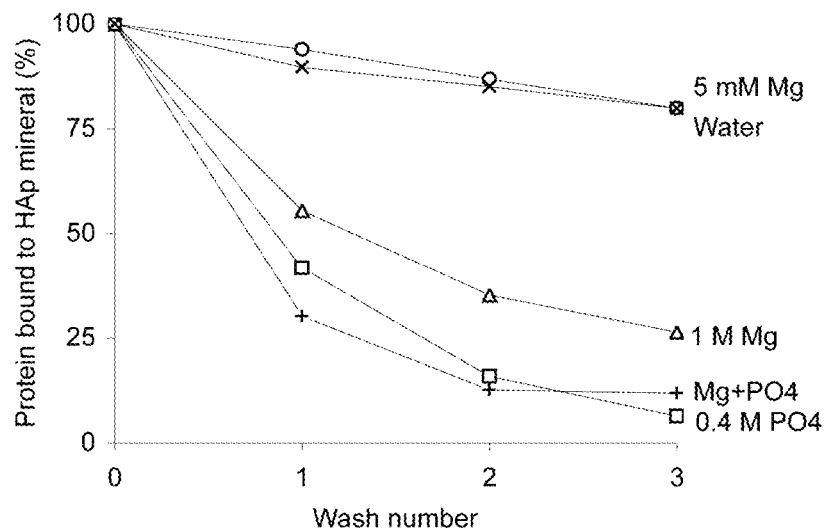
FIG. 40 depicts the results of Example 13 that demonstrate the relative effectiveness of combined application of a washing solution comprising $Mg^{2+}$ and $PO_4$ in removing proteins bound to pure hydroxyapatite.

Example 13—Analysis of Combined $Mg^{2+}$ Plus $PO_4$ Wash Using Pure Hydroxyapatite (FIG. 40)

Methods

Pure hydroxyapatite was loaded with protein, then subjected to 100 μl of combined wash (1 M $MgCl_2$, 0.4 M $NaH_2PO_4$) three times as for Example 11. Protein content was assessed as for Example 11. Note that results from Example 13 (FIG. 40) are charted alongside data from Example 12 for comparison.

Results

The combination wash performed similarly to $PO_4$ alone, however the hydroxyapatite turned white after the first wash (similar to 1M $Mg^{2+}$ alone), indicating the activity of each wash component was retained. It may be concluded that a combined wash may be more effective in terms of the time required to achieve protein removal.

Figure 41:
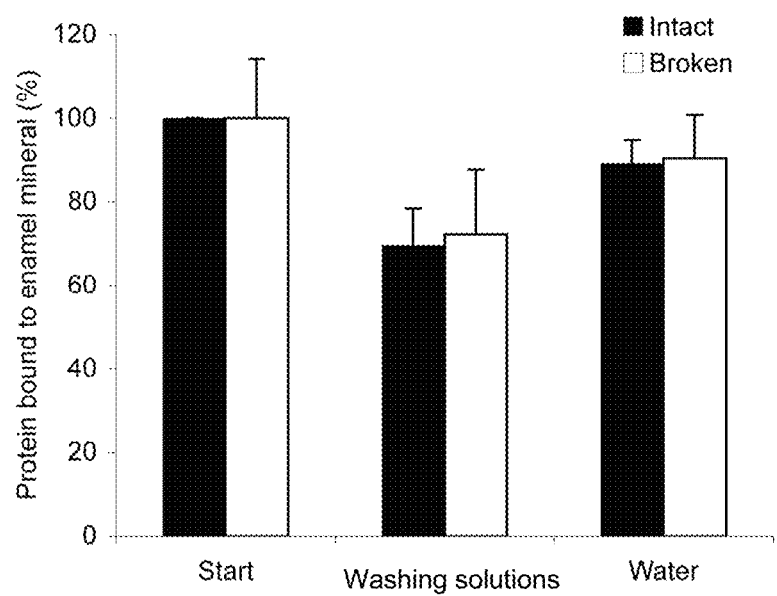
FIG. 41 depicts the results of Example 14 that demonstrate that application of washing solutions comprising $Mg^{2+}$ or $PO_4$ removes proteins from hypomineralised enamel, although with reduced efficacy compared with the hydroxyapatite model of Examples 11 to 13.

Example 14—Washing Solutions Work on Hypomineralised Enamel, Although with Reduced Efficacy Compared with the Hydroxyapatite Model (FIG. 41)

Methods

Hypomineralised enamel from intact and broken lesions was collected separately such that 3 tubes of 5 mg powder were available for each type of lesion. Enamel was exposed to 100 µl of 5 mM $Mg^{2+}$, 1 M $Mg^{2+}$, then 0.4 M $PO_4$, each for 5 minutes. Samples were then treated as for the pure hydroxyapatite of Examples 11 to 13.

Results

Treatment of hypomineralised enamel with washing solutions removed a substantial amount of protein (~¼-⅓), whereas water was barely effective (FIG. 41). The amount of protein removed was less that that seen for the hydroxyapatite model, possibly due to slower off-rates.

Figure 42:
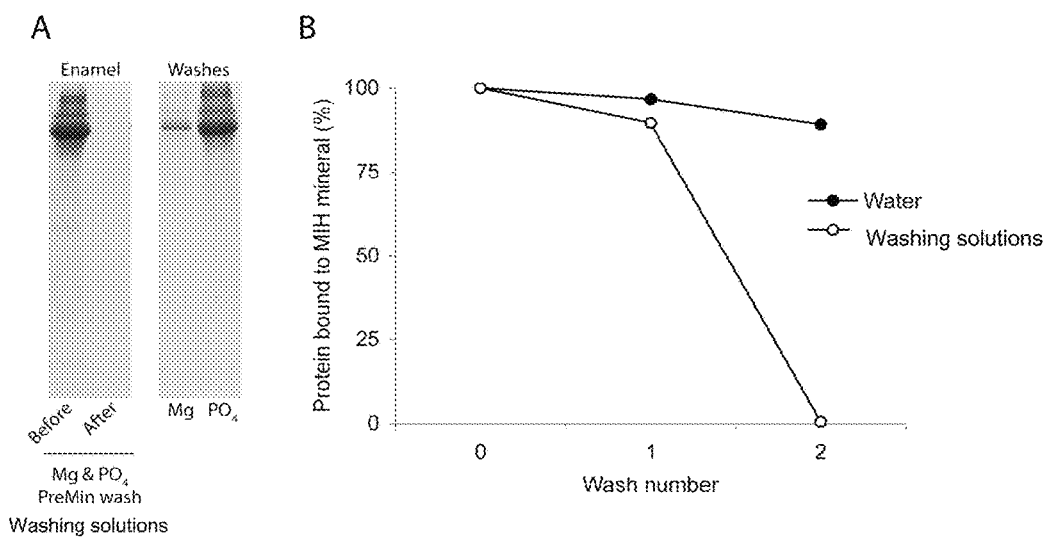
FIG. 42 depicts the results of Example 15 that demonstrate that the efficacy of washing solutions comprising $Mg^{2+}$ or $PO_4$ in removing proteins from hypomineralised enamel can be improved compared with Example 14 by extending the application period such that the proteins can be removed quantitatively.

Example 15—Washing Solutions can Quantitatively Remove Proteins from Hypomineralised Enamel (FIG. 42)

Methods

Hypomineralised enamel from an intact lesion was collected such that 3 tubes of 5 mg was available. Enamel was exposed to 1 ml of 1 M $Mg^{2+}$ for 7 hours, then 1 ml 0.4 M $PO_4$ for a further 16 hours. Samples were then treated as for the pure hydroxyapatite of Examples 11 to 13.

Results

Proteins were quantitatively removed from hypomineralised enamel after two extended washes with washing solutions (FIG. 42B), whereas water treatment over the same timeframe had little effect. The $PO_4$ wash had greatest effect, likely due to the protein profile of this particular lesion (predominantly albumin, FIG. 42A). While the timeframe may be longer than desirable, the washing solutions are capable of removing all protein from clinical specimens.

REFERENCES

Hubbard M J (1995). Calbindin 28 kDa and calmodulin are hyperabundant in rat dental enamel cells. Identification of the protein phosphatase calcineurin as a principal calmodulin target and of a secretion-related role for calbindin28 kDa. *Eur J Biochem* 230:68-79.

Hubbard M J (1996). Abundant calcium homeostasis machinery in rat dental enamel cells. Up-regulation of calcium store proteins during enamel mineralisation implicates the endoplasmic reticulum in calcium transcytosis. *Eur J Biochem* 239:611-623.

Mangum J E, Veith P D, Reynolds E C, Hubbard M J (2006). Towards second-generation proteome analysis of murine enamel-forming cells. *Eur J Oral Sci* 114 Suppl 1:259-265.

Weerheijm K L (2003). Molar incisor hypomineralisation (MIH). *Eur J Paediatr Dent* 4:114-120.

The invention claimed is:

1. A method for detecting porous dental hydroxyapatite, the method comprising:
   (a) contacting a tooth of a subject with a probe comprising a protein covalently linked to a colored reporter, wherein the protein is selected from the group consisting of Serum albumin; Complement C3 beta chain; Alpha-1-antitrypsin; Protein S100-A9; Lactotransferrin; Leukocyte elastase inhibitor; Antithrombin-III; Hemoglobin subunit alpha; Hemoglobin subunit beta; Hemoglobin subunit delta; Prolactin-inducible protein; Alpha amylase 1; Ig kappa chain V-III region SIE; Ig alpha-2 chain C region; Uncharacterized protein c6orf58; Serpin B3; osteocalcin; decorin; and Amelogenin, wherein the protein specifically binds to porous dental hydroxyapatite; and
   (b) detecting the probe specifically bound to the porous dental hydroxyapatite, thereby locating the porous dental hydroxyapatite, wherein the porous dental hydroxyapatite is a condition selected from incipient dental caries, dental caries, Molar/Incisor Hypomineralization, amelogenesis imperfecta, dental fluorosis, or other developmental dental defect; and
   (c) remineralizing or remediating the tooth using a remineralization agent or remedial mineralization agent wherein the remineralization agent or remedial mineralization agent comprises fluoride, soluble calcium phosphate or amorphous calcium phosphate.

2. The method of claim 1, wherein the protein is Hemoglobin subunit alpha, Hemoglobin subunit beta, or Hemoglobin subunit delta.

3. The method of claim 1, wherein the protein is covalently linked to the colored reporter via a cysteine thiol.

4. The method of claim 1, wherein the protein is Hemoglobin subunit alpha, Hemoglobin subunit beta, or Hemoglobin subunit delta, the coloured reporter is amido black, and the protein and colored reporter are covalently linked by SMCC.

5. The method of claim 1, wherein detecting comprises visual inspection.

6. The method of claim 1, wherein the subject is a human.

7. The method of claim 1, further comprising permeabilizing the tooth before contacting the tooth with the probe.

8. The method of claim 1, comprising contacting the tooth of the subject with the probe for a period of time no longer than 20 minutes.

9. The method of claim 1, comprising contacting the tooth of the subject with the probe for a period of time no longer than 10 minutes.

10. The method of claim 1, comprising contacting the tooth of the subject with the probe for a period of time no longer than 5 minutes.

11. The method of claim 1, comprising contacting the tooth of the subject with the probe for a period of time no longer than 3 minutes.

12. The method of claim 1, wherein the probe further comprises a linker linking the protein to the reporter.

13. The method of claim 12, wherein the linker is a cross-linker.

14. The method of claim 13, wherein the cross-linker is a heterobifunctional cross-linker.

15. The method of claim 14, wherein the heterobifunctional cross-linker is succinimidyl 4-[N-maleimidomethyl] cyclohexanecarboxylic acid N-hydroxysuccinimide ester (SMCC) or succinimidyl-6[β-maleimidopropionamido] hexanoate (SMPH).

16. The method of claim 1, wherein the colored reporter is selected from the group consisting of an amido black, a naphthalene blue black, a Sudan black, an acid blue, an alcian blue, an alizarin blue, an alizarol cyanin, an alkali blue, an aniline blue, an anthracine blue, an azure A-C, a basic blue, a celestine blue, a Chicago blue, a chromoxane cyanin, a direct blue, a Durazol blue, a fast blue, a gallamine blue, a hematein, a hematoxylin, an indigo carmine, a mauveine, a methylene blue, a nitro blue, a toluidine blue, a trypan blue, a night blue, a nile blue, a pontamine blue, a Victoria blue, a water blue, an acid green, a basic green, a brilliant green, an ethyl/methyl green, a fast green, a gallein, a guinee green, an iodine green, a malachite green, a naphthol green, a magenta, a fuchsin, an acid violet, an aniline purple, a chrome violet, an ethyl/methyl violet, an Hoffman's violet, a Lauff's violet, and a primuline.

17. The method of claim 16, wherein the colored reporter is amido black.

18. The method of claim 1, further comprising removing the probe or a protein bound to porous dental hydroxyapatite by washing the tooth with one or more washing solutions.

19. The method of claim 18, wherein the one or more washing solutions comprise magnesium ions, dihydrogen phosphate ions, hydrogen phosphate ions, phosphate ions, hypochlorite ions, or a mixture thereof.

20. The method of claim 19, wherein the one or more washing solutions comprise magnesium chloride and/or sodium dihydrogen phosphate.

21. The method of claim 20, wherein the one or more washing solutions comprise about 1M magnesium chloride and/or about 0.4M sodium dihydrogen phosphate.

* * * * *